United States Patent [19]

Takehana et al.

[11] Patent Number: 5,269,289
[45] Date of Patent: Dec. 14, 1993

[54] CAVITY INSERT DEVICE USING FUZZY THEORY

[75] Inventors: Sakae Takehana, Machida; Shouichi Ieoka, Takahama; Kazuo Sonobe, Hachioji; Hiroki Hibino, Hachioji; Tomohisa Sakurai, Hachioji; Yutaka Takahashi, Hachioji; Akira Murata, Hachioji; Nobuyuki Sakamoto, Hachioji; Yoshihiro Kosaka, Hachioji; Koichi Matsui, Tokyo; Akihiro Miyashita, Hachioji; Masakazu Gotanda, Tsukui; Kazutada Kobayashi, Hachioji; Koji Koda, Hachioji; Masao Uehara, Hachioji; Katsuyuki Saito, Kokubunji; Akinobu Uchikubo, Hachioji; Shinji Yamashita, Hachioji; Takehiro Nakagawa, Hachioji; Koji Tanikawa, Hachioji, all of Japan

[73] Assignee: Olympus Optical Co., Ltd., Tokyo, Japan

[21] Appl. No.: 683,360

[22] Filed: Apr. 9, 1991

[30] Foreign Application Priority Data

Dec. 25, 1990 [JP] Japan ................................. 2-406113

[51] Int. Cl.[5] ............................................. A61B 1/00
[52] U.S. Cl. ........................................................ 128/4
[58] Field of Search ............................ 128/662.06, 4-9

[56] References Cited

U.S. PATENT DOCUMENTS

| 4,676,228 | 1/1987 | Krasner et al. | 128/4 |
| 4,690,131 | 9/1987 | Lyddy, Jr. et al. | 128/4 |
| 4,727,417 | 2/1988 | Kanno et al. | 128/4 X |
| 4,740,837 | 4/1988 | Yanagisawa et al. | 128/4 X |
| 4,977,886 | 12/1990 | Takahara et al. | 128/4 |
| 4,996,975 | 3/1991 | Nakamura | 128/4 X |
| 5,018,509 | 5/1991 | Suzuki et al. | 358/98 X |

Primary Examiner—Francis Jaworski
Attorney, Agent, or Firm—Armstrong, Westerman, Hattori, McLeland & Naughton

[57] ABSTRACT

A cavity insert device comprising an insert section capable of being inserted into tracts and cavities, a detection circuit for detecting conditions of components making up the device, such as an observation device formed at the distal end side of the insert section, and a fuzzy inference section for synthetically determining a plurality of information signals outputted from the detection circuit and producing control signals to control the components. The fuzzy inference section employs inference rules which are empirically considered to be desirable, and control is made by the control signals obtained with the fuzzy inference. The device is thus operated in a nearly optimum state.

87 Claims, 55 Drawing Sheets

FIG. 4(a)
RULE 1
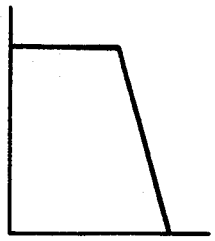
AVERAGE VALUE OF SKIN COLOR
LOW   HIGH
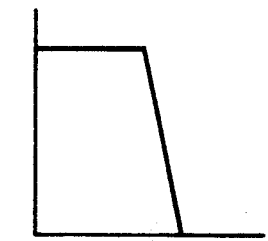
AVERAGE VALUE OF LUMINANCE
DARK   LIGHT
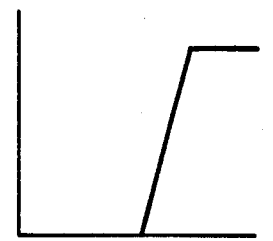
GAIN CONTROL
SMALL GAIN   LARGE GAIN
FIG. 4(b)
RULE 2
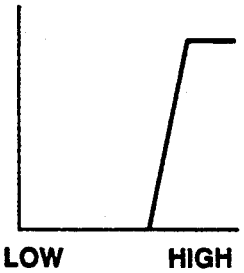
AVERAGE VALUE OF SKIN COLOR
LOW   HIGH
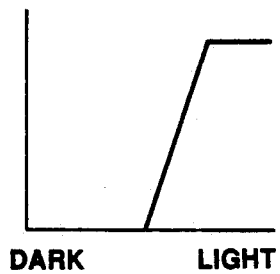
AVERAGE VALUE OF LUMINANCE
DARK   LIGHT
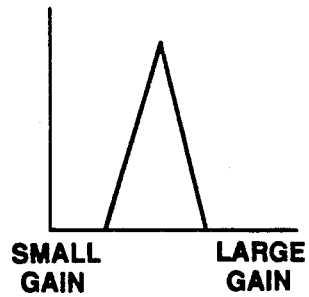
GAIN CONTROL
SMALL GAIN   LARGE GAIN
FIG. 5(a)
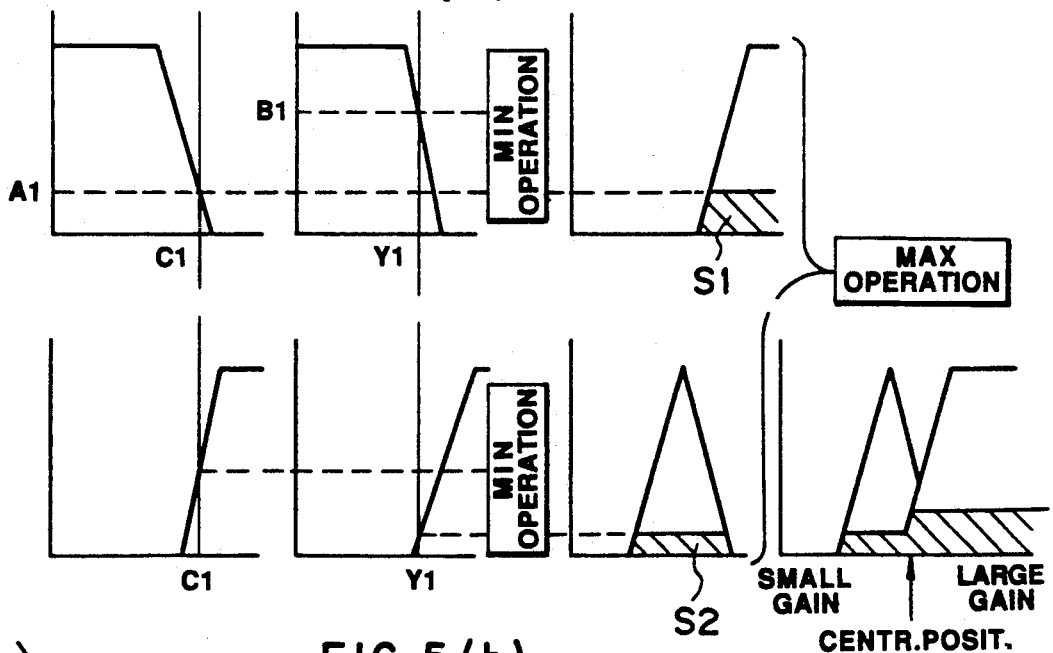
FIG. 5(b)

FIG.7(a)
RULE 1
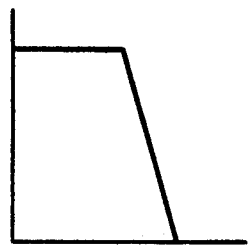
AVERAGE VALUE OF SKIN COLOR
LOW — HIGH
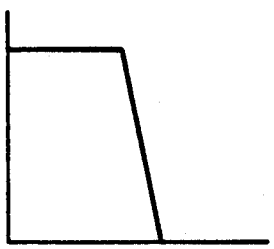
AVERAGE VALUE OF LUMINANCE
DARK — LIGHT
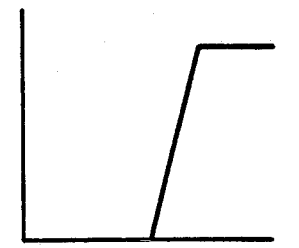
DIAPHRAGM CONTROL
LARGE DIAPHR. QUAN. — SMALL DIAPHR. QUAN.
FIG.7(b)
RULE 2
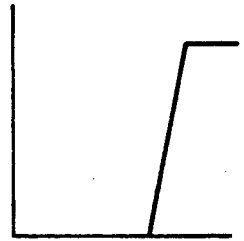
AVERAGE VALUE OF SKIN COLOR
LOW — HIGH
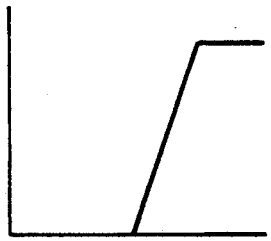
AVERAGE VALUE OF LUMINANCE
DARK — LIGHT
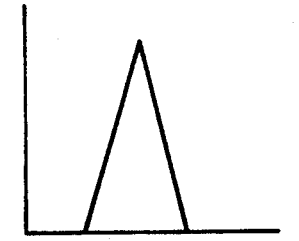
DIAPHRAGM CONTROL
LARGE DIAPHR. QUAN. — SMALL DIAPHR. QUAN.
FIG.8(a)
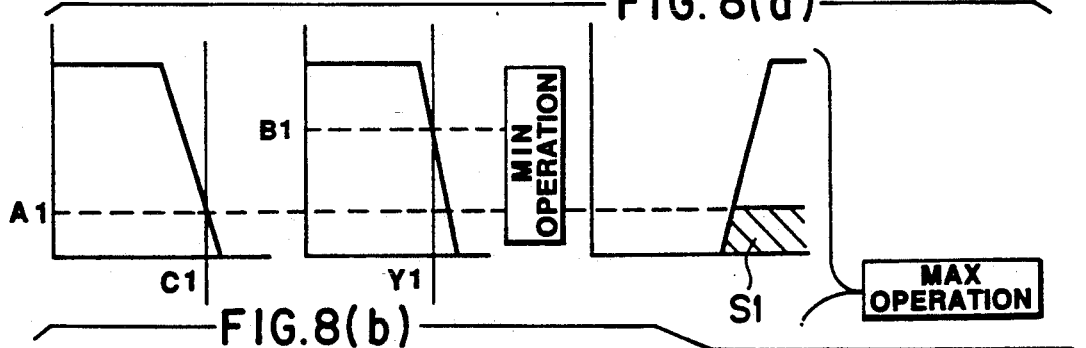
FIG.8(b)
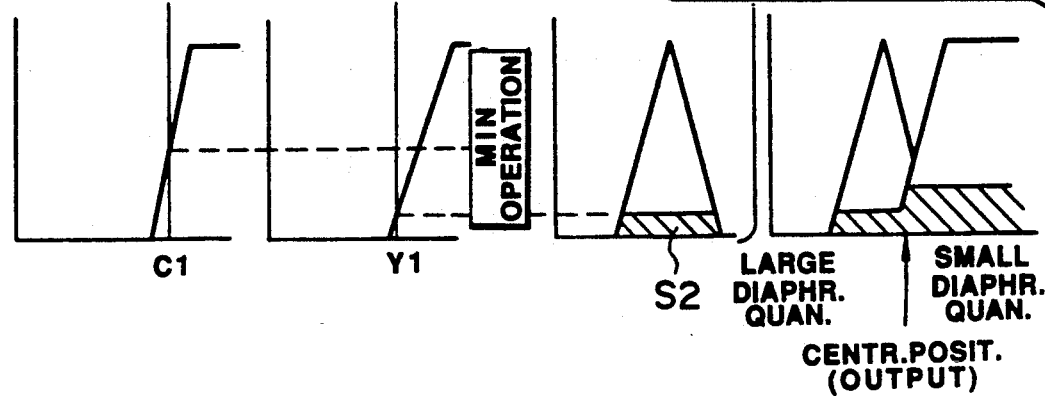

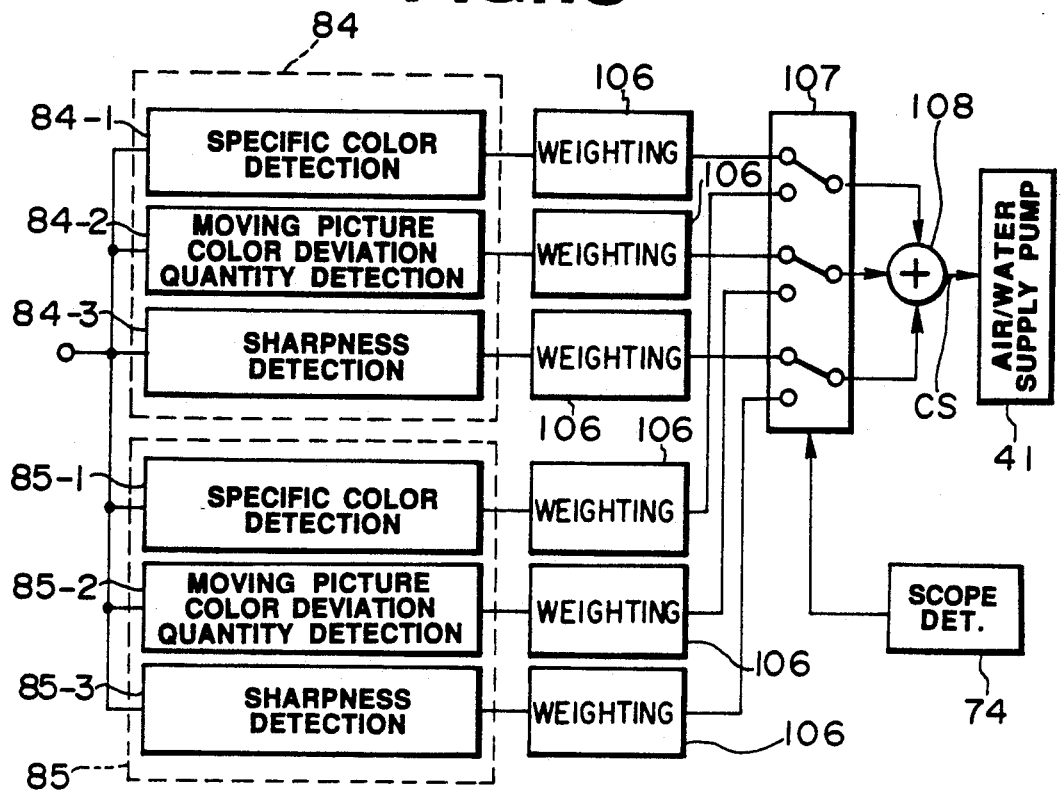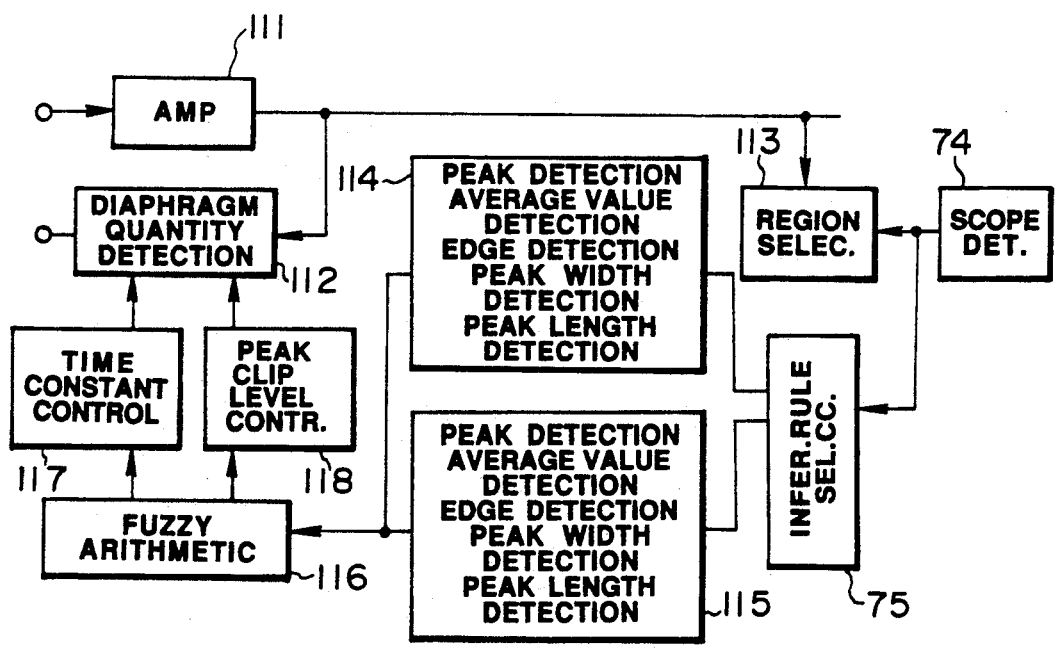

FIG. 18(a)　　FIG. 18(b)
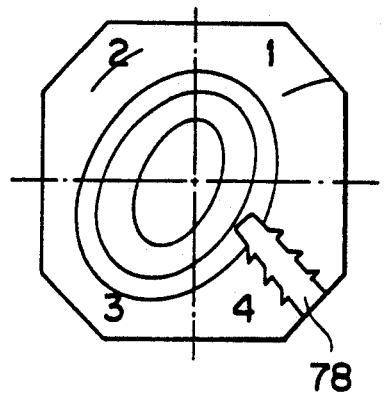
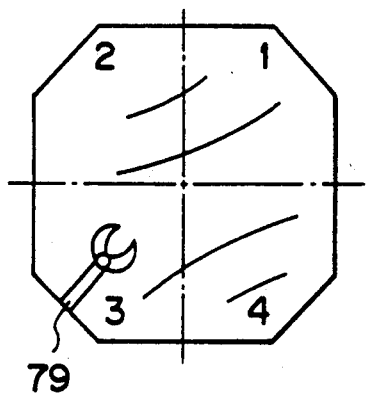
FIG. 19
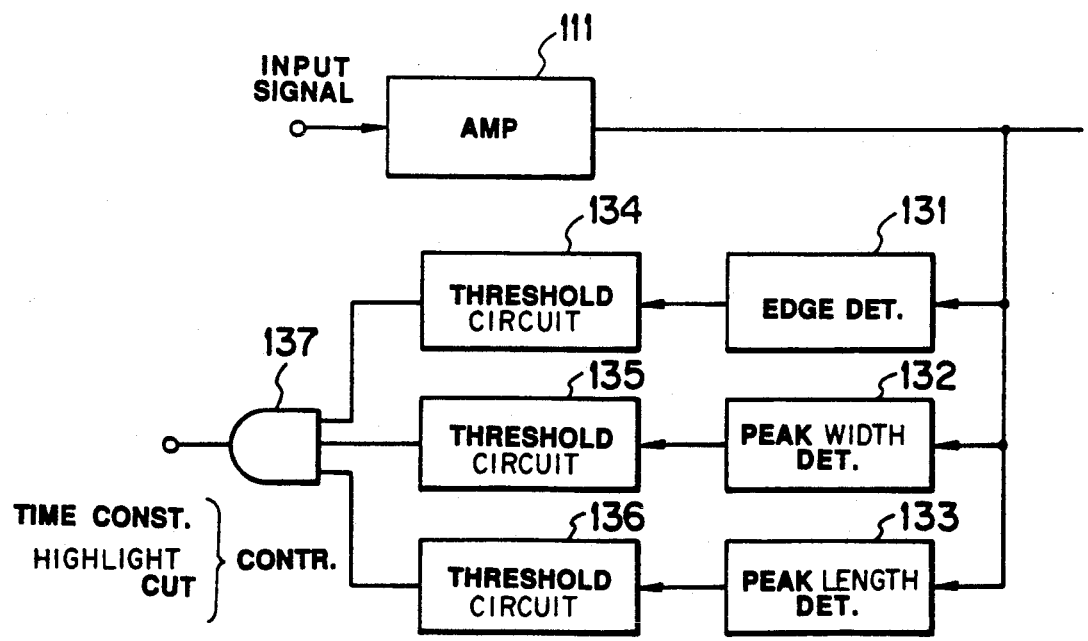

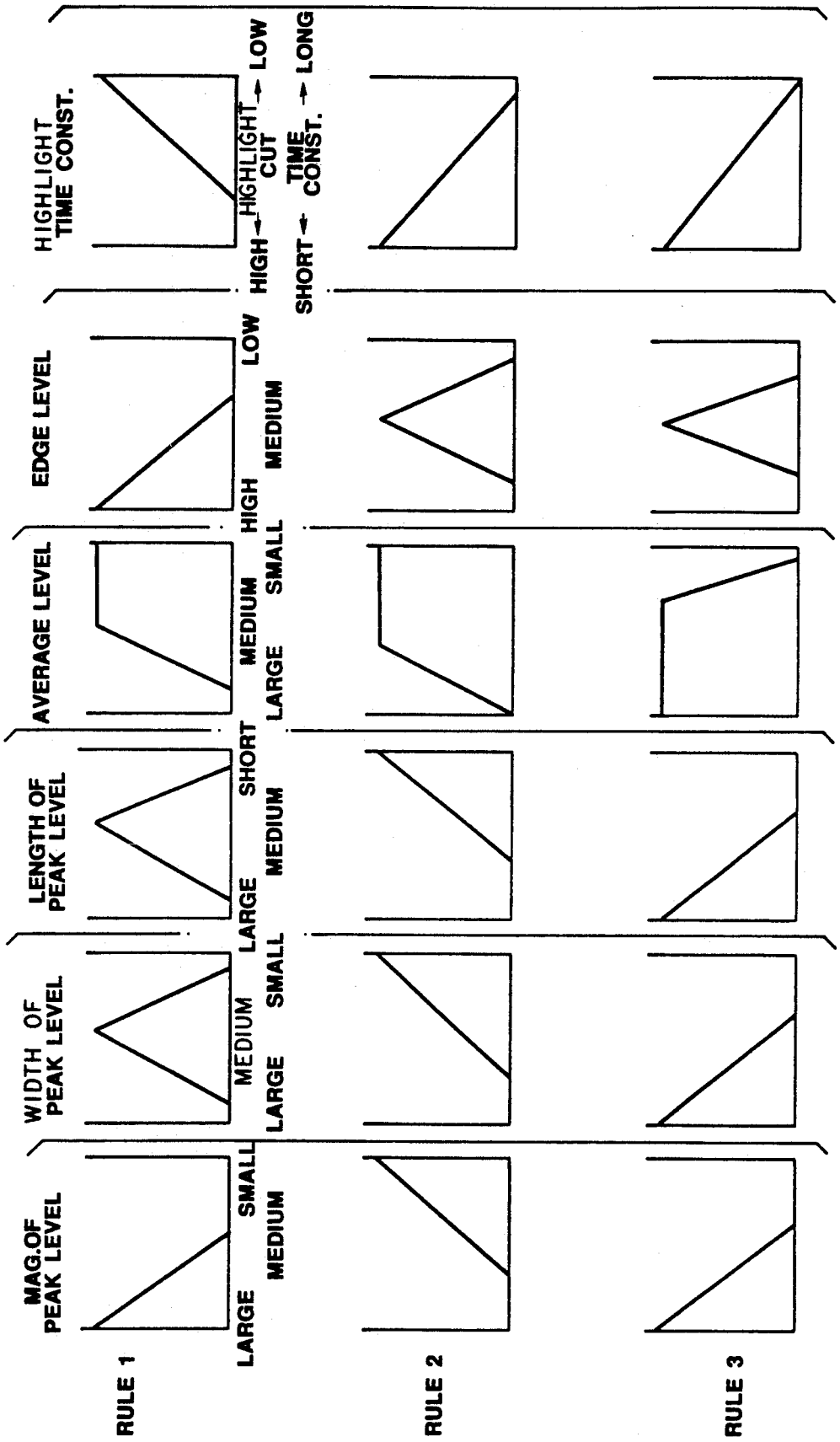

OUTPUT
(INFERENCE RESULT)

FIG.29
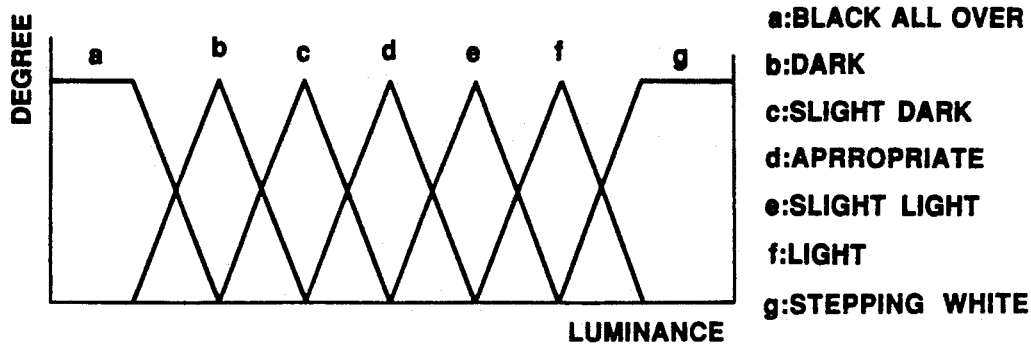
a: BLACK ALL OVER
b: DARK
c: SLIGHT DARK
d: APRROPRIATE
e: SLIGHT LIGHT
f: LIGHT
g: STEPPING WHITE
FIG.30
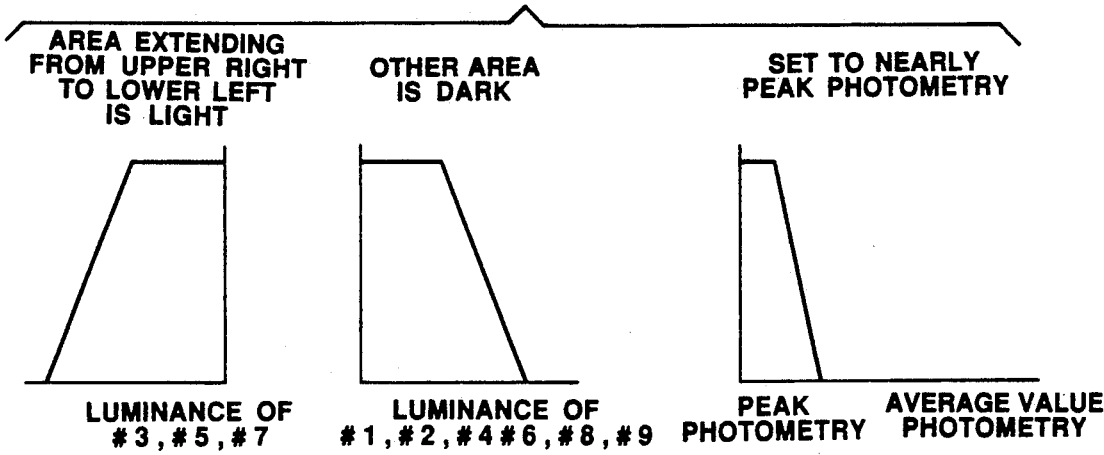
FIG.31(a)    FIG.31(b)
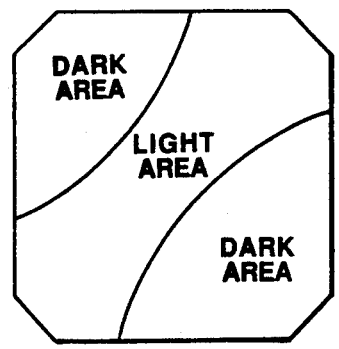  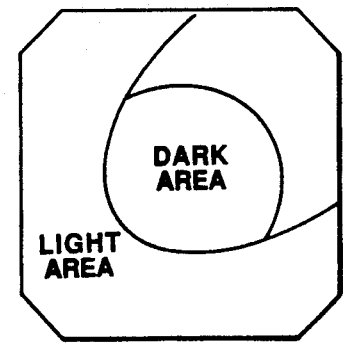

FIG. 36A FIG. 36B
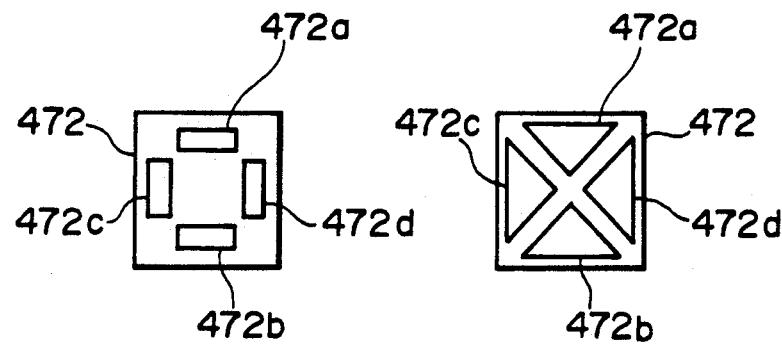
FIG. 38
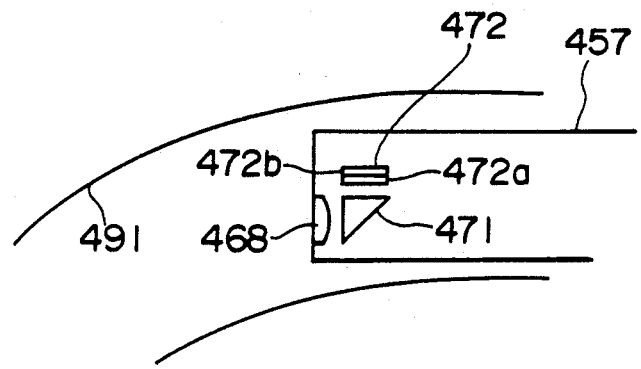
FIG. 40a
FIG. 40b CONTACT Sc
FIG. 40c CONTACT Sa
FIG. 40d CONTACT Sd
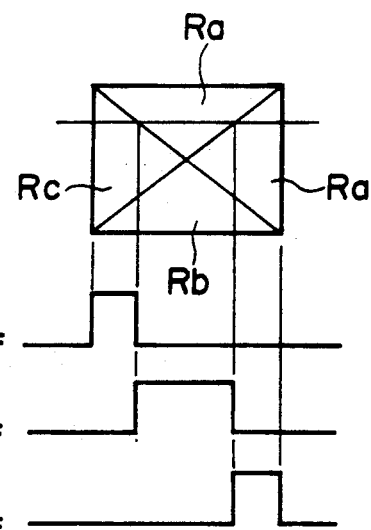

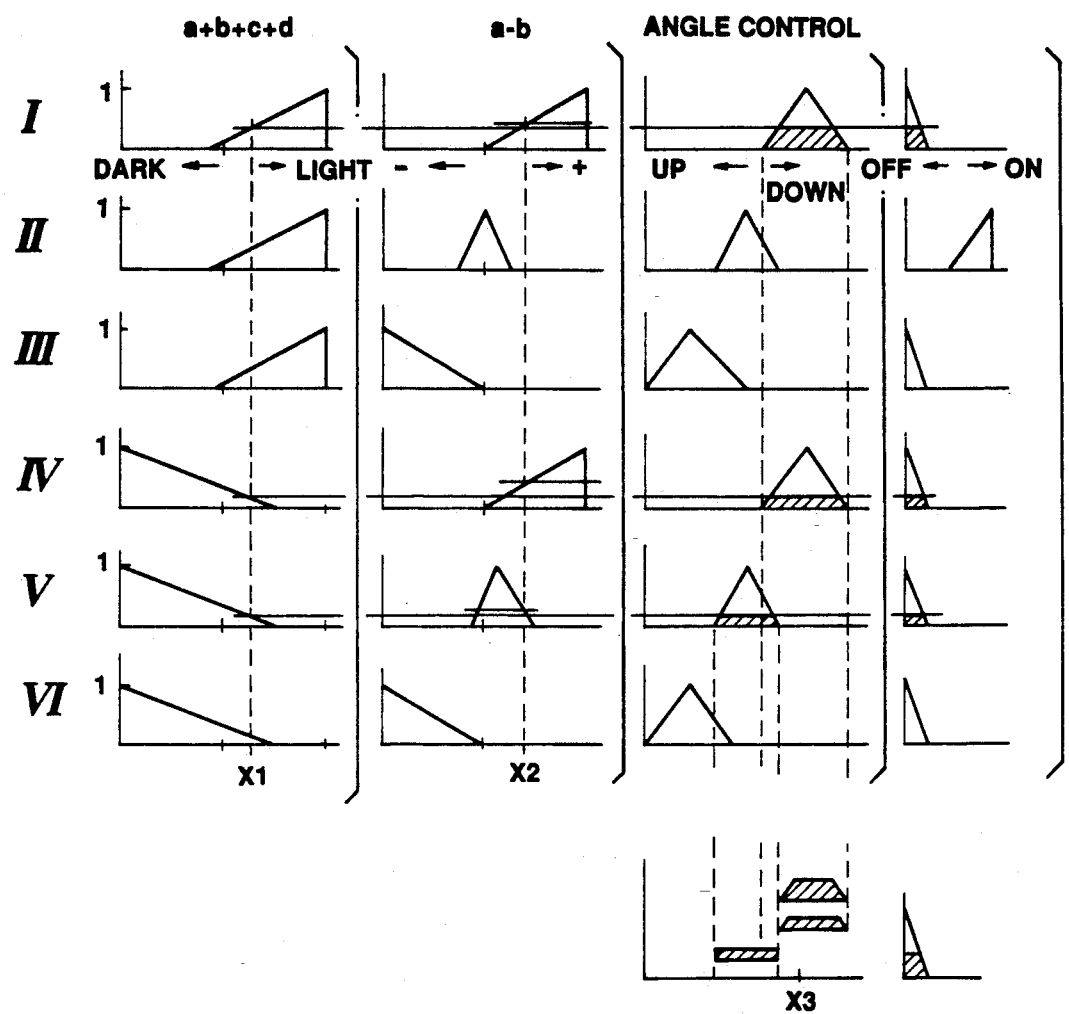

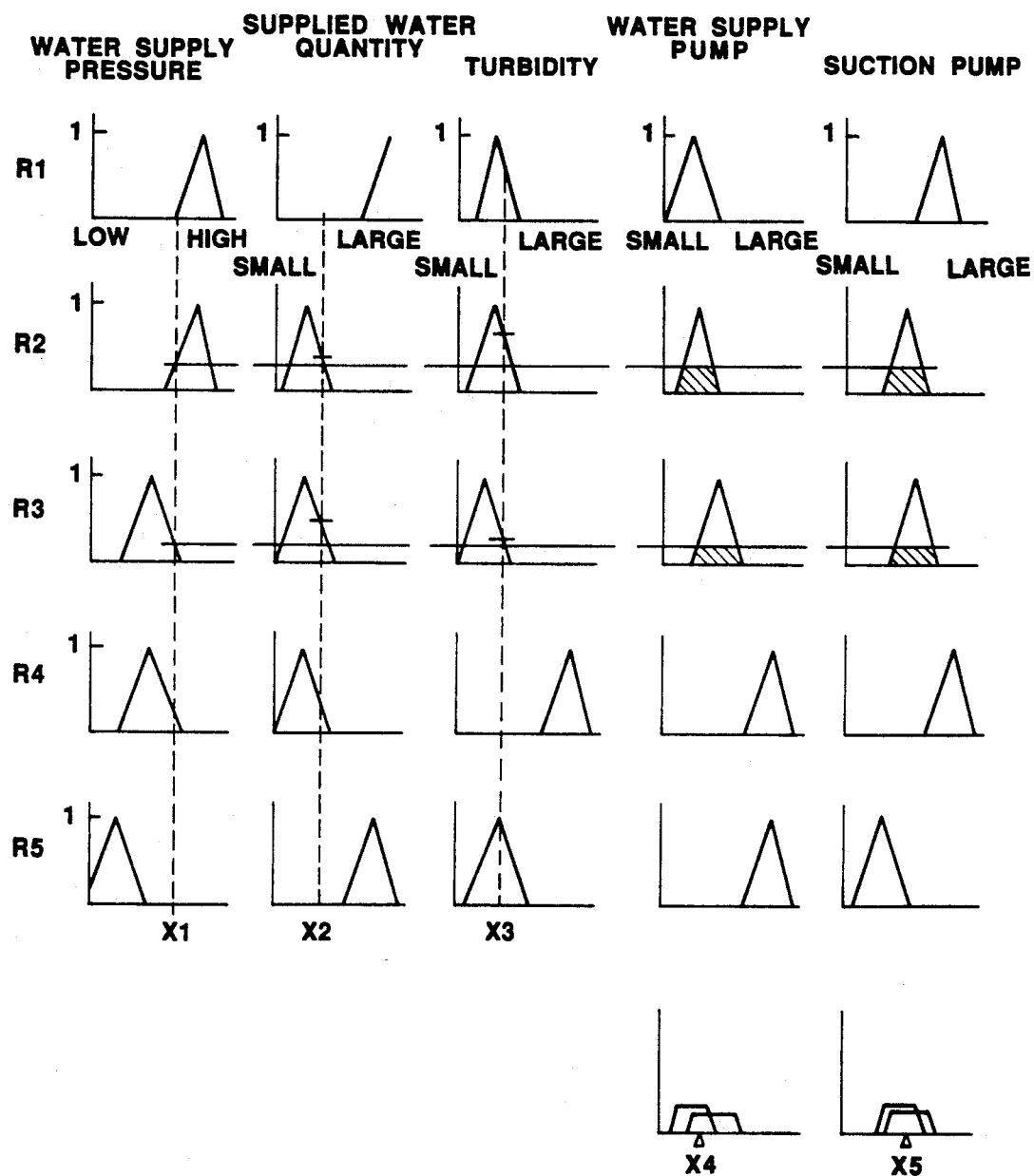

FIG.59(a)  FIG.59(b)  FIG.59(c)
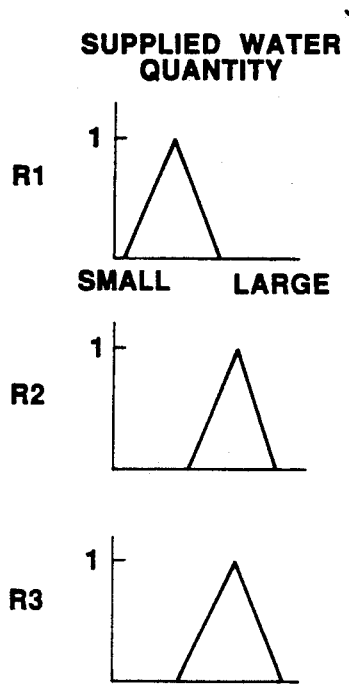
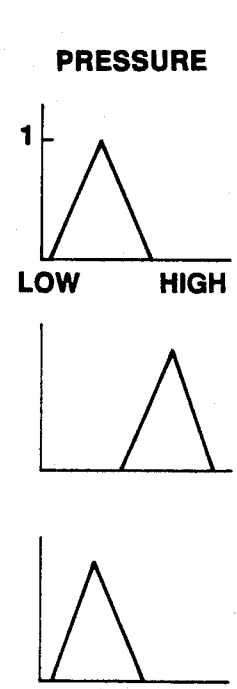
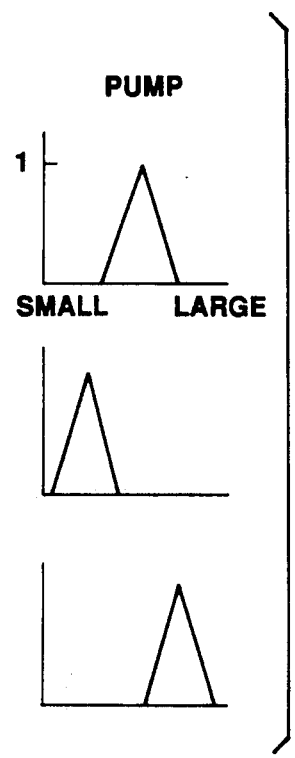
FIG.61
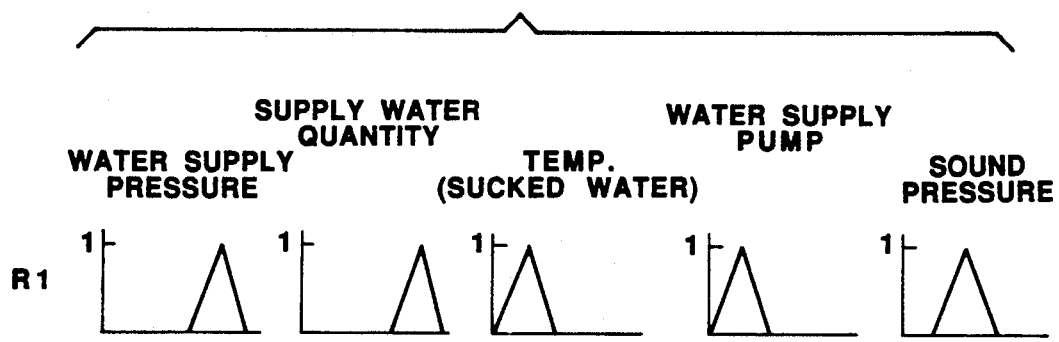

FIG. 60
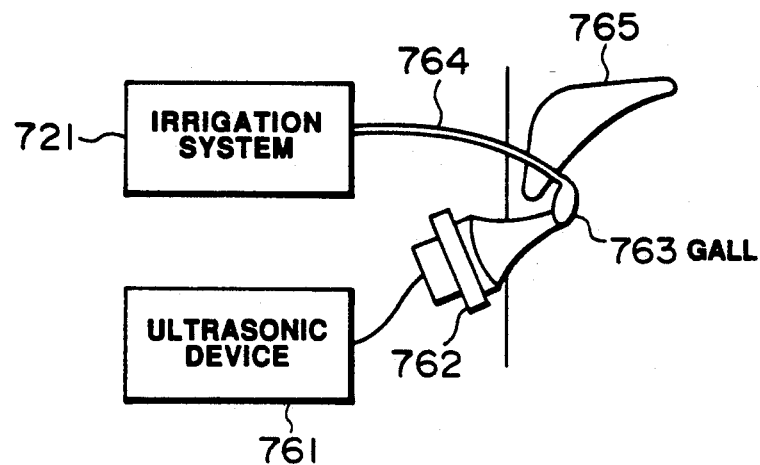
FIG. 62(a)
SUPPLIED WATER QUANTITY
R1 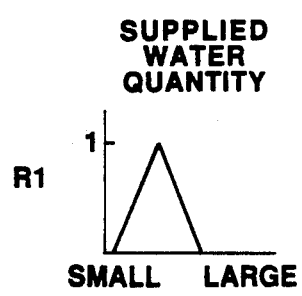
SMALL    LARGE
R2
R3 X2 X2
FIG. 62(b)
PRESSURE
R1 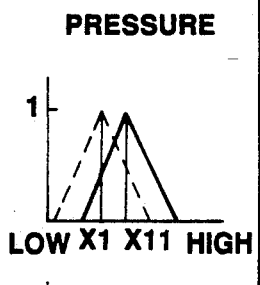
LOW X1 X11 HIGH
R2
R3
FIG. 62(c)
PUMP
R1
SMALL    LARGE
R2 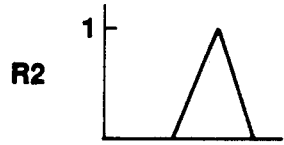
R3 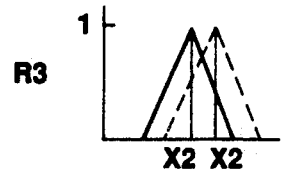
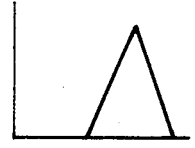
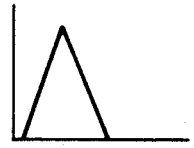
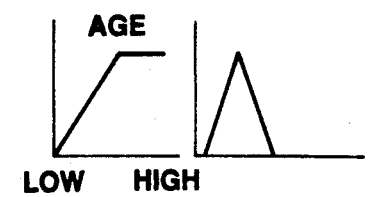
AGE
LOW    HIGH
FIG. 62(b")

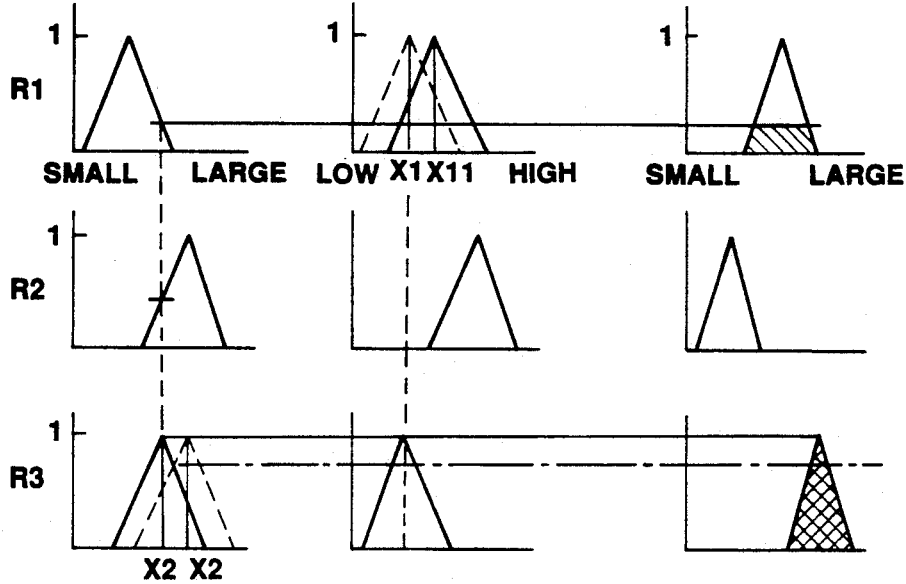
FIG.63(a) SUPPLIED WATER QUANTITY
FIG.63(b) PRESSURE
FIG.63(c) PUMP
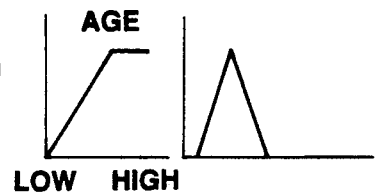
FIG.63(b')
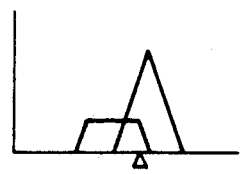
FIG.63(d") AFTER CORRECTION (USING R1,R2,R3)
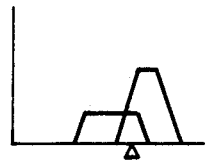
FIG.63(e") BEFORE CORRECTION (USING R1,R2,R3)

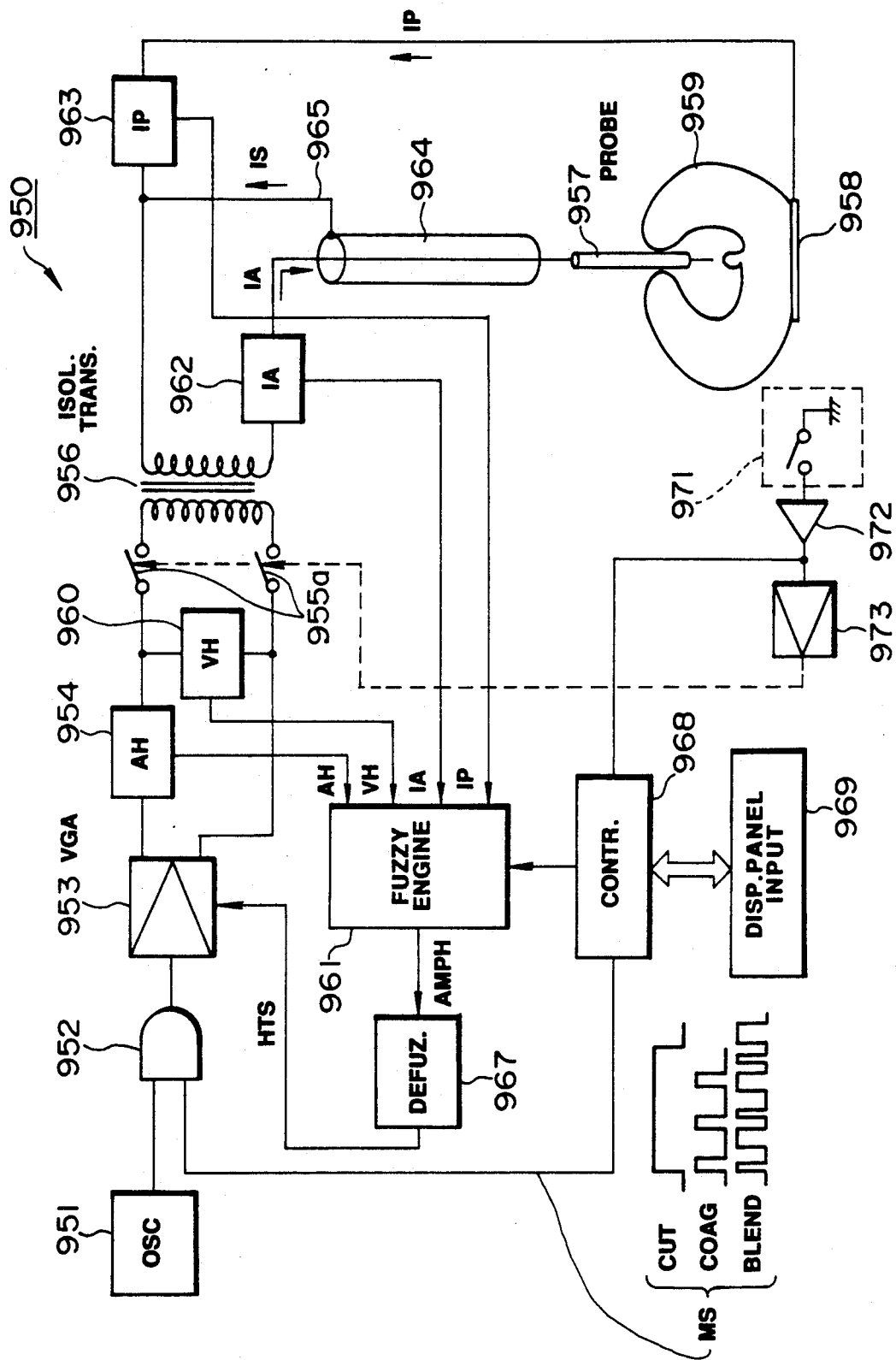

$\theta = \dfrac{IP}{IA}$ (CURRENT FEEDBACK FACTOR)

CAVITY INSERT DEVICE USING FUZZY THEORY

BACKGROUND OF THE INVENTION

1. Field of the Invention

The present invention relates to a cavity insert device which is inserted into a cavity such as the body cavity while performing fuzzy inference.

2. Description of Related Art

As well known, an endoscope to be inserted into the body cavity enables a user to observe the interior of a living body which cannot be directly seen visually, and is widely used for observation and treatment primarily in the field of medical service. Recently, an electronic endoscope has become widespread in which an image of an object (or subject) is converted into an electric signal by an image sensing means such as a CCD, enabling the object image to be observed by a monitor. For the purpose of making the user always observe the image from the endoscope easily and clearly, there are needed adjustment of AGC for an image pickup signal, highlighting of profiles, adjustment of an iris diaphragm, air/water supply operation for cleaning an objective lens at a distal end face of the endoscope, as well as control of a device shutter for a freeze shot in endoscopes of synchronous imaging type. Thus, an endoscope is required to judge situations and carry out proper control depending on the place and state where it is used, that is, into which location the endoscope is inserted, whether it is used under a spread condition of chemicals or a bleeding condition, or whether an object is moving quickly. In a conventional endoscope device, the user determines the state of an endoscope by seeing an observation image, and then controls the endoscope device to be fit for the determined state based on his or her own knowledge and experience.

The aforesaid endoscope device has suffered from the problem that because various control elements of the endoscope device, such as AGC adjustment, profile highlighting, adjustment of the iris diaphragm and air/water supply operation, rely on an ability of individuals using the endoscope device, a good image could not be obtained unless the user has a some degree of skill or experience in the use of endoscopes. Also, when inserting the endoscope into a location of the body cavity where observation is to be carried out, it is difficult to smoothly insert the endoscope, i.e., to insert it while making patients feel little pain, unless the user is well experienced.

Such a problem of smooth insertion is not limited to endoscopes to be inserted into living bodies, and similarly arises in any other type cavity insert devices to be inserted into general tracts and cavities. Thus, the cavity insert device also requires some experience to sufficiently accomplish its function. This leads to the problem that a less-experienced operator cannot achieve as satisfactory an operating state of the device as is obtainable by an experienced operator, thereby developing a difference between the results observed by both the operators. In other words, there is a problem that even with the same device being used, a less-experienced operator may adequately operate and control the device making it difficult to obtain the desired result.

SUMMARY OF THE INVENTION

An object of the present invention is to provide a cavity insert device which can work in a proper state with simple operation without needing skilled experience.

Another object of the present invention is to provide a cavity insert device which can be inserted into a target location with simple operation without needing skilled experience.

A still other object of the present invention is to provide an endoscope device which can easily produce a good image without needing skilled experience.

The cavity insert device comprises an insert section inserted into tracts and cavities, observation means or treatment means provided on the insert section, detection means for detecting a plurality of status signals related to an environmental condition of the device, and fuzzy inference means for synthetically determining the plurality of status signals from the detection means and controlling the insert section, the observation means and the treatment means. With such an arrangement, it is possible in the cavity insert device inserted into the tracts and cavities for purpose of observation or treatment that the fuzzy inference means automatically sets, based on the plurality of status signals, the device to a control state which can bring forth the same inference result as obtained by a well-experienced operator, thus allowing even a less-experienced operator to operate the device in a nearly optimum state.

BRIEF DESCRIPTION OF THE DRAWINGS

FIGS. 1 through 6 relate to a first embodiment of the present invention in which; FIG. 1 is an arrangement view of an electronic endoscope device according to the first embodiment of the present invention, FIG. 2 is a block diagram showing an arrangement of primary components of the first embodiment, FIG. 3 is block diagram of a luminance/color arithmetic circuit in FIG. 2, FIGS. 4(a) and 4(b) are a set of explanatory charts showing membership functions in the first embodiment, FIGS. 5(a) and 5(b) are a set of charts for explaining a manner to obtain an inference result based on fuzzy rules, FIG. 6 is a representation for explaining general fuzzy inference, FIGS. 7(a) and 7(b) are set of explanatory charts showing fuzzy rules in a modification of the first embodiment of the present invention, and FIGS. 8(a) and 8(b) are a set of charts for explaining a manner to obtain an inference result based on the fuzzy rules in the modification of FIG. 7;

FIGS. 9 through 16 relate to a second embodiment of the present invention in which; FIG. 9 is an arrangement view of an electronic endoscope device according to the second embodiment of the present invention, FIG. 10 is a circuit diagram showing the circuit configuration of a scope detection circuit and so on in FIG. 9, FIG. 11 is a block diagram of primary components of the second embodiment, FIG. 13 is a block diagram showing a practical example of a specified color detection circuit, FIG. 14 is a circuit diagram showing a practical example of a moving picture color deviation quantity detecting circuit, FIG. 15 is a set of explanatory charts showing fuzzy rules in the second embodiment, and FIG. 16 is a block diagram for air/water supply control without using fuzzy inference;

FIGS. 17 through 21 relate to a third embodiment of the present invention in which; FIG. 17 is a block diagram of the third embodiment, FIGS. 18(a) and 18(b) are explanatory representations showing that treatment appliances appear at different positions depending on the scopes, FIG. 19 is a block diagram showing an arrangement to perform diaphragm control without using fuzzy inference, FIG. 20 is a block diagram of primary components in a modification of the third embodiment of the present invention, FIGS. 21(a), 21(b), 21(c), 21(d), 21(e) and 21(f) are a set of explanatory charts showing typical examples of fuzzy rules in the third embodiment.

FIGS. 23 through 25 relate to a fourth embodiment of the present invention in which; FIG. 23 is an arrangement view of the third embodiment, FIG. 24 is a set of explanatory charts showing fuzzy rules in the fourth embodiment, and FIG. 25 is a chart showing an inference result based on FIG. 24;

FIGS. 26 through 33 relate to a fifth embodiment of the present invention in which; FIG. 26 is a conceptual arrangement view of the fifth embodiment, FIG. 27 is an arrangement view of primary components of the fifth embodiment, FIG. 28 is an explanatory view showing a manner to divide an endoscope into plural regions, FIG. 29 is a chart showing membership functions for an antecedent portion in the fifth embodiment, FIG. 30 is a set of charts showing fuzzy rules applied to observation of the stomach corner, FIGS. 31(a) and 31(b) are a set of representations showing distribution of light and dark areas resulted from observing the stomach corner and the gullet, FIG. 32 is a set of charts showing fuzzy rules applied to observation of the gullet, and FIG. 33 is a representation for explaining a manner to obtain an inference result based on the fuzzy rules;

FIGS. 35 through 38 relate to a seventh embodiment of the present invention in which; FIG. 35 is an arrangement view of an automatic insertion device of the seventh embodiment, FIGS. 36(a) and 36(b) are a front view showing a light receiving section, FIGS. 37(a), 37(b), 37(c), 37(d), 37(e) and 37(f) are a set of explanatory charts showing control rules, and FIG. 38 is an explanatory view showing a condition that an endoscope is inserted into a body cavity;

FIGS. 39 and 40(a), 40(b), 40(c) and 40(d) relate to an eighth embodiment of the present invention in which; FIG. 39 is an arrangement view of an automatic insertion device of the eighth embodiment, and FIGS. 40(a), 40(b), 40(c) and 40(d) are a set of charts for explaining the timing at which switches are changed over, FIGS. 41 through 45 relate to a ninth embodiment of the present invention in which.

FIGS. 46 and 47(a), 47(b), 47(c), 47(d) and 47(e) relate to a tenth embodiment of the present invention in which; FIG. 46 is an arrangement view of an endoscope device of the tenth embodiment, and FIGS. 47(a), 47(b), 47(c), 47(d) and 47(e) are a set of explanatory charts showing membership functions;

FIGS. 48 through 51 relate to an eleventh embodiment of the present invention in which; FIG. 48 is a block diagram showing an arrangement of an active endoscope device of the eleventh embodiment, FIG. 49 is a set of explanatory charts showing fuzzy rules and membership functions, FIG. 50 is a set of explanatory charts showing one example of inputs and an inference result in the fuzzy inference, and FIG. 51 is a set of explanatory charts showing another example of inputs and an inference result in the fuzzy inference;

FIGS. 53 through 63 relate to an thirteenth embodiment of the present invention in which; FIG. 53 is a basic block diagram of the thirteenth embodiment, FIG. 54 is an entire block diagram of the thirteenth embodiment, FIG. 55 is an explanatory view showing a manner of excision by an electric scalpel device, FIG. 56 is a block diagram showing a practical example of a membership switching/inputting means, FIGS. 59(a), 59(b), and 59(c) are a set of explanatory charts showing typical examples of control rules made up by membership functions in the case of including no suction control, FIG. 60 is an explanatory view showing a manner to use the thirteenth embodiment for dissolving a gallstone, FIG. 61 is a set of explanatory charts showing one example of control rules made up by membership functions in the case of FIG. 60, FIGS. 62(a), 62(b), 62(b'') and 62(c) are a set of explanatory charts showing control rules resulted from modifying the controls rules in FIG. 59, and FIGS. 63(a), 63(b), 63(b'), 63(c), 63(d'') and 63(e'') are a set of explanatory charts showing output values in the respective cases using the control rules in FIGS. 59 and 62;

FIGS. 64 and 65(a), 65(b), 65(c) and 65(d) relate to a fourteenth embodiment of the present invention in which; FIG. 64 is a block diagram of the fourteenth embodiment, and FIGS. 65(a), 65(b), 65(c) and 65(d) are a set of explanatory charts showing fuzzy rules and membership functions;

FIGS. 66 through 69 relate to a fifteenth embodiment of the present invention in which; FIG. 66 is an arrangement view of an entire system of the fifteenth embodiment, FIG. 67 is a block diagram showing an arrangement of a fuzzy inference means, and FIGS. 68(a), 68(b), 68(c), 68(d) and 69 are each a set of explanatory charts showing membership functions representative of fuzzy rules used for fuzzy inference;

FIGS. 70 through 73 relate to a sixteenth embodiment of the present invention in which; FIG. 70 is an arrangement view of primary components of the sixteenth embodiment, FIG. 71 is a block diagram showing an arrangement of an image processing unit, FIG. 72 is an explanatory view showing a manner to determine the size of a flaw, etc. on a monitor screen, and FIG. 73 is a block diagram showing an arrangement of a fuzzy inference means;

FIGS. 76 through 79(a), 79(b) and 79(c) relate to an eighteenth embodiment of the present invention in which; FIG. 76 is a block diagram showing an arrangement of a ultrasonic diagnosis apparatus including a data interpolation device, FIG. 77 is an explanatory view showing positions and sizes of raw data and interpolation data, FIG. 78 is a set of explanatory charts showing fuzzy rules and membership functions, FIG. 79a is an explanatory view showing raw data, FIG. 79b is an explanatory view showing raw data and interpolation data according to a conventional interpolation method, and FIG. 79c is an explanatory view showing raw data and interpolation data according to an interpolation method of this embodiment; and FIGS. 80 through 82 relate to a nineteenth embodiment of the present invention in which; FIG. 80 is an arrangement view of an electric scalpel device including an output control unit of an electric scalpel, and FIGS. 81 and 82 are graphs for explaining operation.

DETAILED DESCRIPTION OF PREFERRED EMBODIMENTS

Hereinafter, the present invention will be described in detail with reference to the drawings.

Figure 6:
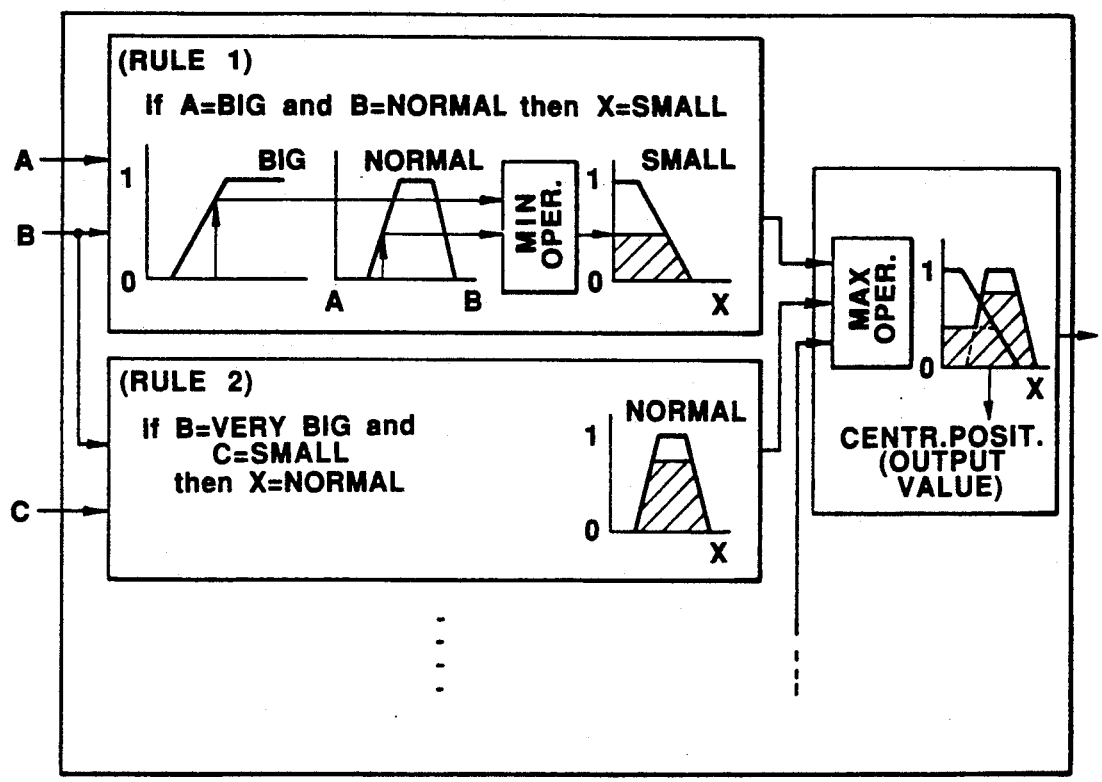

Prior to describiing embodiments of the present invention, fuzzy inference will be summarized by referring to FIG. 6. The term "fuzzy inference" implies inference that employs fuzzy rules (fuzzy inference rules) expressed by ambiguous words daily spoken by people. A fuzzy rule can be described as "if A=BIG and B=NORMAL then X=SMALL". In FIG. 6, A, B are input variables and X is an output variable. The portion "if A=BIG and B=NORMAL" describing conditions for establishment of the rule is called an antecedent portion, while the conclusion portion "then X=SMALL" is called a consequent portion. In the fuzzy inference, each input variable is converted into a value in a range of 0 to 1 for arithmetic operation, and this conversion is defined by a membership function (antecedent membership function). The membership function is defined for each of propositions (BIG, NORMAL, SMALL, etc.) handled by fuzzy rules. The degree at which the input variable satisfies the corresponding proposition is calculated while referring to the membership function. When the antecedent portion has a plurality of propositions, the minimum value among the resulting degrees is obtained. This step is called a minimum value (MIN) operation. Then, membership values for every rule is synthesized. The synthesis is performed by comparing the consequent portions of respective rules with each other, taking a maximum value among them, and producing a new membership function. This step is called a maximum value (MAX) operation. The position of center of gravity (the centroid) of the membership function thus synthesized becomes an inference result (output value), based on which subsequent control is carried out.

While the inference technique of FIG. 6 is a typical example, there are also proposed other several ones. The following embodiments will be explained in accordance with the inference technique of FIG. 6, but the present invention is applicable to the cases of adopting other inference techniques as well.

A first embodiment equipped with a means for carrying out the above fuzzy inference will be explained below.

Figure 1:
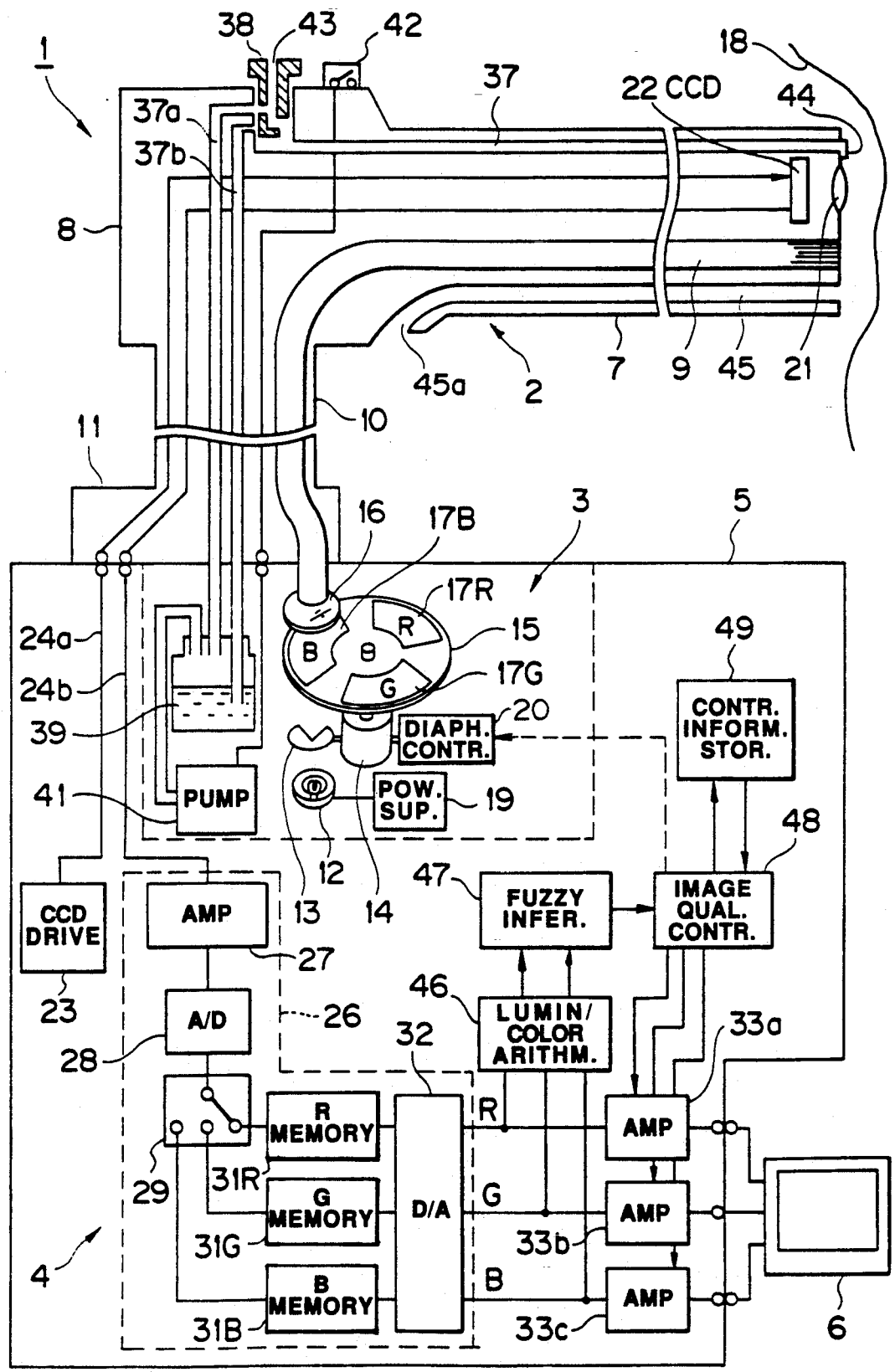

As shown in FIG. 1, an electronic endoscope device 1 of the first embodiment comprises a frame sequential electronic scope 2, a video processor 5 incorporating both a frame sequential light source unit 3 to supply frame sequentially illuminating light to the electronic scope 2 and. an image processing (signal processing) circuit 4, and a display 6 for displaying video signals outputted from the video processor 5 in colors.

The electronic scope 2 has an slender insert section 7 and a thicker operating section 8 formed at a rear end of the insert section 7.

A light guide 9 for transmitting the illumination light therethrough is penetrated through the insert section 7 and then further penetrated through a universal cord 10 extending from the operating section 8. A connector 11 at an end of the universal cord 10 can be fitted to the video processor 5. Fitting the connector 11 permits the illumination light from the light source unit 3 to be supplied to an incident end face of the light guide 9.

White light from a lamp 12 passes through a diaphragm 13, a rotatable color filter 15 rotated by a motor 14, and further a condenser lens 16, followed by entering the incident end face of the light guide 9.

In the rotatable color filter 15, there are formed three sector-like openings equally spaced in the circumferential direction and provided with filters 17R, 17G and 17B for transmitting rays of red, green and blue light therethrough, respectively. Thus, light rays corresponding to wavelengths of red, green and blue, namely, beams of frame sequential light, are successively supplied to the light guide 9. The beams of frame sequential light are transmitted through the light guide 9 and irradiated from an emergent end face attached to the distal end of the insert section 7 toward an object 18 in front of the emergent end face. Electric power is supplied from a lamp power supply 19 to the lamp 12. The diaphragm 13 is controlled by a diaphragm control circuit 20 comprising a motor, etc. so as to come into or out of an optical path for variably controlling the intensity of illumination light.

An optical image of the object 18, illuminated by the illumination light emitted from the emergent end face of the light guide 9, is focused by an objective lens 21 attached to the distal end of the insert section 7 on a light receiving surface (photoelectric conversion surface) of a CCD 22 disposed in the focal plane of the objective lens 21.

The optical image is subjected to photoelectric conversion by the CCD 22 and stored therein in the form of electric charges.

When a drive signal outputted from a CCD drive circuit 23 in the video processor 5 is applied to the CCD 22 via a signal line 24a, the optical image is read out and inputted via a signal line 24b to a video signal producing circuit 26 in the video processor 5. The video signal producing circuit 26 carries out signal processing to produce standard video signals, for example, three primary color signals R, G, B, which are issued from respective output terminals of the video signal producing circuit 26.

In the video signal producing circuit 26, a CCD output signal is amplified by an amplifier 27 and converted into a digital signal by an A/D converter 28. The digital signal is successively written into R, G, B memories 31R, 31G, 31B via a multiplexer 29. For instance, the image signal picked up under the red illumination light is temporarily written into the R memory 31R. When a component image for one frame is written into each of the R, G, B memories 31R, 31G, 31B, the component images in the R, G, B memories 31R, 31G, 31B are read out at the same time and converted into analog signals by a D/A converter 32. Thus, the standard three primary color signals R, G, B are outputted from the video signal producing circuit 26. These three primary color signals R, G, B are then outputted from the video processor 5 via respective amplifiers 33a, 33b, 33c each variable in its gain, so that the image of the object is displayed on the display 6 in colors.

An air/water supply tube 37 for supplying air or water therethrough is also penetrated through the insert section 7 and branched into two tubes 37a, 37b on the upstream side of an air/water supply switching button 38 in the operating section 8. These tubes 37a, 37b are penetrated through the universal cord 10 and connected to an air/water supply tank 39 when the connector 11 is coupled to the video processor 5. The air/water supply tank 39 is connected to a pump 41 via a tube so that the interior of the tank 39 is pressurized by turning on a switch 42 to energize/de-energize the pump 41, thereby supplying air or water.

Because the button 38 has an opening 43 normally communicating the tube 37a with the exterior, even if the switch 42 is turned on, the air supplied from the tank 39 via the tube 37a is discharged to the exterior through the opening 43. When the opening 43 is closed by a finger, the supplied air is jetted from a nozzle 44 at the distal end of the insert section 7 via the tube 37 toward an outer surface of the objective lens 21 located in opposite relation to the nozzle 44.

When the button 38 is pushed downwards, the tube 37b is brought into communication with the tube 37 so that the water in the tank 39 may be jetted from the nozzle 44 via the tubes 37b, 37 to flush away mucus or the like deposited on the outer surface of the objective lens 21.

Further, a channel 45 is defined in the insert section 7, allowing a treatment appliance to be inserted through the channel 45 from a channel insertion port 45a so that a distal end of the treatment appliance may be projected out of an opening at the distal end of the insert section 7 for proper treatment or remedy.

Figure 2:
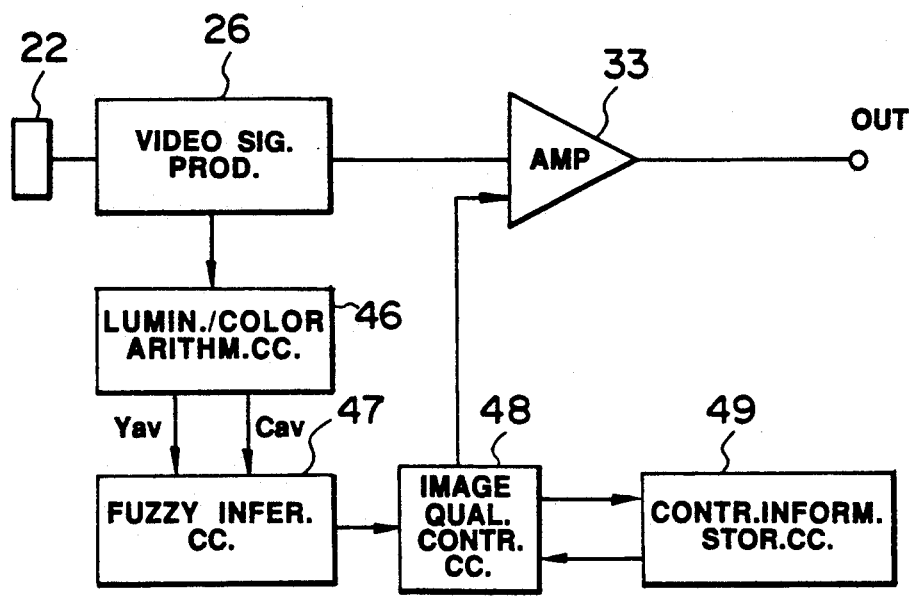

In this first embodiment, the three primary color signals R, G, B outputted from the video signal producing circuit 26 are, as shown in FIG. 2, applied to a luminance/color arithmetic circuit 46 to produce an average luminance signal Yav and an average specific color signal Cav which are then applied to a fuzzy inference circuit 47 as a means for inferring an image state of the object. The fuzzy inference circuit 47 determines whether the image state of the object is normal or not, and outputs an inference result signal depending on the determination to an image quality control circuit 48. Based on the inference result signal applied, the image quality control circuit 48 obtains weighting information, as control information, read out of a control information storage circuit 49 and outputs control signals for controlling levels of the respective image pickup signals, etc.

The control signals are respectively applied to gain control terminals of the amplifiers 33a through 33c for controlling levels of the three primary color signals R, G, B to become proper level values.

Figure 3:
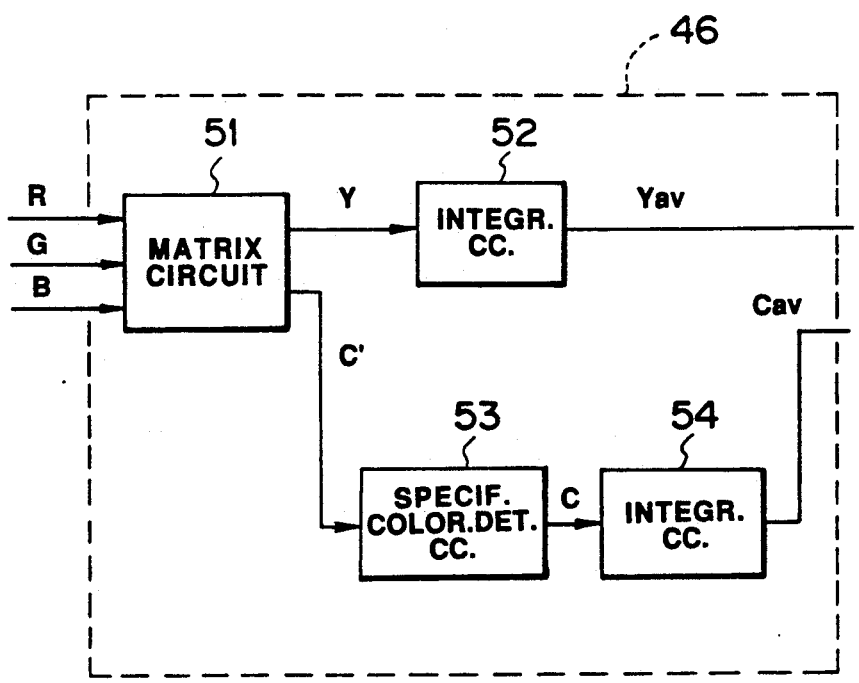

The configuration of the luminance/color arithmetic circuit 46 is shown in FIG. 3.

The three primary color signals R, G, B are subjected to a matrix operation in a matrix circuit 51 to produce a luminance signal Y and a color signal C'. The luminance signal Y is inputted to an integrating circuit 52 where it is integrated for a period of one frame, for example, to produce an average luminance signal Yav. The color signal C' is inputted to a specific color detecting circuit 53 for producing, with a matrix operation or the like, a specific color signal C corresponding to a component of skin color as a particular color (specific color). Afterward, the specific color signal C is integrated by an integrating circuit 54 to produce an average specific color signal Cav. Those average signals Yav, Cav are inputted to the fuzzy inference circuit 47 which determines whether the observed image of the object is normal or not, using those average signals Yav, Cav as image determining information of the object. The control signal resulting from this determination is outputted for image quality control (luminance level control in this case).

In general endoscope inspection, there is often employed a dye endoscope method of spraying a dye over the diseased part and thereabout to clearly discriminate the normal part and the diseased part.

Table 1 lists various dyes used in that method.

TABLE 1

| Dye name | Color |
|---|---|
| Congo red | red |
| Indigo carmine | dark blue |
| Methylene blue | dark blue |
| Toluidine blue | blue-violet |
| Iodine | brown |

Since those dyes have low luminance (reflectance), the use of those dyes would make the entire picture darker than the normal image (unless an automatic light adjustment is carried out). Also, during remedy using a treatment appliance, blood frequently discharges at the time of inspection of living bodies, etc. and the entire picture becomes red totally due to the bleeding. In this case, too, the entire picture becomes darker than the case of normally observing the endoscope image, thus rendering it hard to make a correct diagnosis.

In this embodoment, the normal image and other special image (caused by a dye or bleeding) are inferred with fuzzy inference using information effective in determining those images, to thereby correct the image quality into a state expedient for diagnosis.

For that purpose, membership functions and inference rules are set as shown in FIG. 4, by way of example, to carry out the fuzzy inference using the average luminance signal Yav and the average specific color signal Cav obtained above.

The rule 1 shown in FIG. 4(a) is set so as to perform gain control for increasing gain when the average value of skin color is low and the average value of luminance is also low.

The rule 2 shown in FIG. 4(b) is set so as to perform gain control for decreasing a gain when the average value of skin color is high and the average value of luminance is also high.

FIG. 5 shows a manner to implement the fuzzy inference by a centroid method from the rules shown in FIG. 4.

Specifically, for instance, output values A1, B1 are obtained form respective membership functions of the rule 1 for a given avarage value C1 of skin color and a given average value Y1 of luminance. The output values A1, B1 are then applied to a MIN operation circuit in the fuzzy inference circuit 47 for deriving a minimum value therebetween. The resulting minimum value, i.e., A1 in this case, is applied to the membership function for setting the gain control, whereby an output value indicated by hatched lines S1 in FIG. 5(a) is obtained.

Similar processing as above is also carried out on the rule 2 and an output value indicated by hatched lines S2 in FIG. 5(b) is obtained. Those output values S1, S2 are subjected to a maximum value operation by a MAX operation circuit for the hatched areas, following which a gain value corresponding to the centroid position is obtained. The gain value is inputted to the image quality control circuit 48. The image quality control circuit 48 carries out the gain control of the amplifiers 33a through 33c so that their gains become equal to the gain value.

The above gain control is effected by reading out control information stored in the control information storage circuit 49. The control information storage circuit 49 comprises, for example, a ROM. The control information storage circuit 49 stores a level value of the gain control signal for the amplifiers 33a through 33c with respect to the gain value, by way of example. Therefore, when the gain value to be set is applied, the level value of the gain control signal corresponding to the gain value is returned. By outputting the gain control signal of the returned level value to the amplifiers 33a through 33c, the video signals outputted to the display 6 are variably controlled in their levels so that the object image may be displayed on the screen of the display 6 with enough brightness to readily make a diagnosis.

For instance, when the luminance level of the object is lowered due to a spread dye or bleeding, the gains of the amplifiers 33a through 33c are increased to compensate for such a decrease in the luminance level, thereby displaying the endoscope image in such a manner as more expedient for diagnosis.

Accordingly, with this embodiment, the image quality is controlled with the fuzzy inference to automatically provide the object image expedient for diagnosis without requiring an operator to perform a gain adjustment or the like based on his or her own experience.

Since the above image quality control is carried out using information suitable to discriminate between the normal image and the special image, it is possible to effect the image quality control in nearly optimum fashion with the fuzzy inference even if high-accurate discrimination is not made.

Taking an example, the dye used is distinctly different from the skin color of normal internal organs. Therefore, the special image due to the dye can be easily discriminated from the normal image by using the information adapted to determine the skin color. In the case of bleeding, the image is turned to deep red and also fairly different from the normal skin color.

Further, because the images resulted in the cases of spreading a dye and bleeding are lowered in its luminance level as compared with the normal image, those images can be reliably discriminated using the information adapted to determine luminance level.

While the first embodiment employs only two types of inference rules for sake of simplicity, it may include three or more inference rules.

For instance, the inference rule may be prepared for each of dyes or each group of dyes adequately grouped. Furthermore, while in this embodiment the luminance/color arithmetic circuit 46 converts the three primary color signals R, G, B into the luminance signal Y and the color signal C' for producing signals used for inference, the present invention is not limited to this embodiment. The input signal for inference may be in the form of a composite signal, a color difference signal or the like. It is also apparent that while the specific color signal is extracted or produced from the color signal C', it may be instead produced from the color difference signal.

With this embodiment, any of the normal and special endoscope images can be set to an image expedient for diagnosis.

Next, a modification of the first embodiment of the present invention will be described. This modification has the same arrangement as the first embodiment except that the output of the image quality control circuit 48 is delivered to not the amplifiers 33a through 33c, but the diaphragm control circuit 20 as indicated by a dot line in FIG. 1.

In other words, the control signal variably controls the diaphragm quantity of the diaphragm 13 via the diaphragm control circuit 20 so that the intensity of illumination light is adjusted to correct the image quality.

Accordingly, the fuzzy inference in this embodiment is used to effect not gain control, but diaphragm control. Control of respective gains of the amplifiers 33a through 33c effected by the gain control functions in a substantially identical manner to control of the intensity of illumination light effected by the diaphragm control. For instance, increasing the gain is substantially identical to an increase in the intensity of illumination light.

The fuzzy inference rules in this modification include, as shown in FIG. 7, the consequent portion for the diaphragm control in place of the gain control in FIG. 4.

Operation of determining the diaphragm quantity with the modified inference rules is shown in FIG. 8.

FIGS. 7 and 8 are almost the same as FIGS. 4 and 5, respectively, and thus will not be described here.

The modification operates substantially like the first embodiment and provides substantially the same effect as the first embodiment. However, the diaphragm control is more advantageous in that in the case of increasing the intensity of illumination light to correct the image quality, the S/N ratio may become larger with an increase in the intensity of illumination light than the case of increasing the gain. Another advantage is in that when observing an object at a short distance, possible damages or the like due to the intensity of illumination light can be prevented more positively by reducing the intensity of illumination light so as to present the proper image quality.

Alternatively, both the gain control and the diaphragm control may be implemented using the control signal. This enables the device to cope with a wider range of conditions in which it is used.

Figure 9:
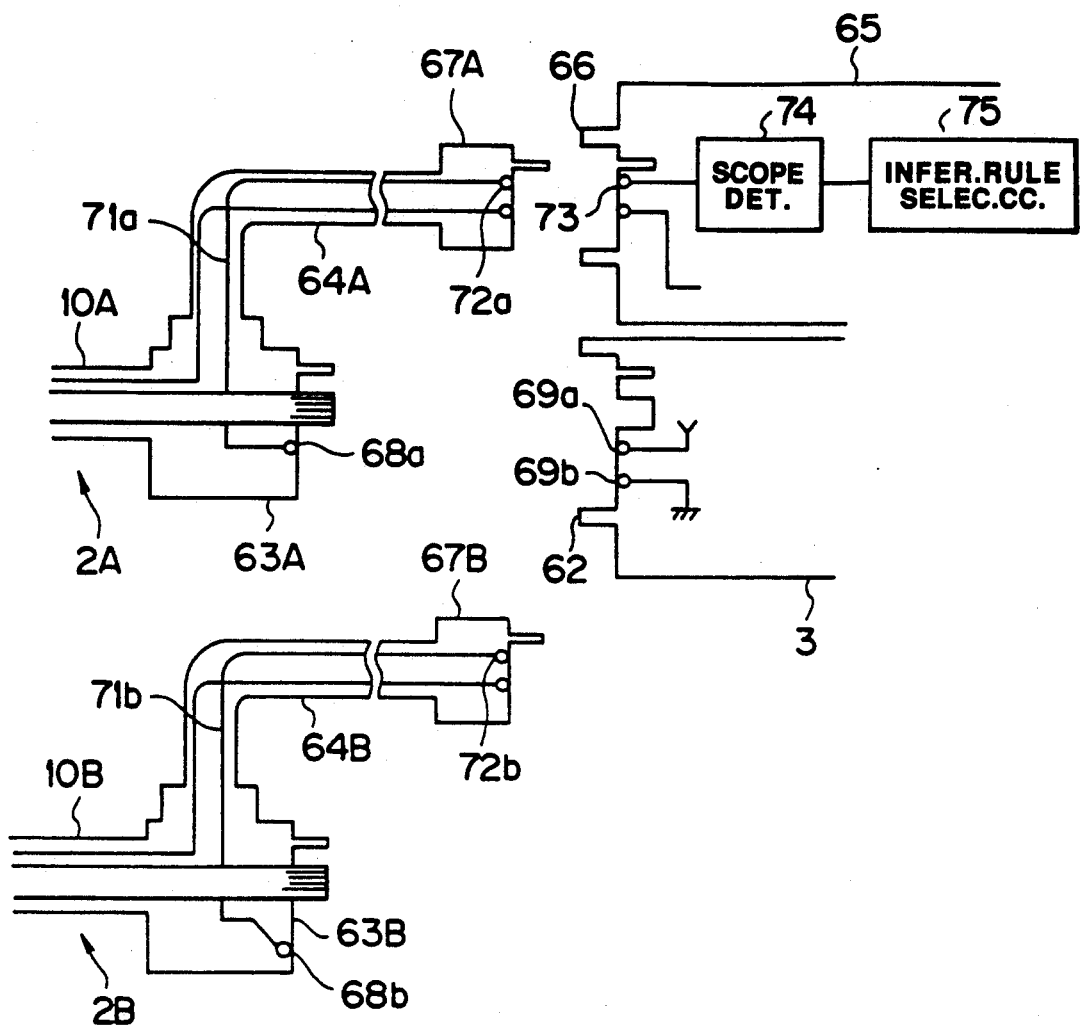

FIG. 9 shows part of an endoscope device of a second embodiment of the present invention. This second embodiment is designed to always provide the endoscope image expedient for diagnosis even if different types of endoscopes are employed.

Generally, depending on locations to be observed, an endoscope of the type fit for the location is used case by case. When observing upper and lower digestive tracts, for example, two types of endoscopes having the insert sections of differing thickness, etc. are used because of different inner diameters of paths through which the endoscopes are inserted. In general endoscopes, if the outer surface of the objective lens is stained, the operator must change the quantity of supplied water depending on a degree of stain of the lens surface.

If the quantity of supplied water is not properly changed, water is supplied in the excessive quantity and thus must be sucked later for a longer period of time. If the quantity of supplied water is too small, the stain cannot be removed sufficiently, or a longer period of time is required to remove the stain, resulting in an increase in pain perceived by patients and the burden imposed on the operator.

This embodiment is designed to properly supply air or water even if different types of endoscopes are used. To this end, as shown in FIG. 9, there is provided a scope detecting means to identify two scopes 2A, 2B for the upper and lower digestive tracts.

The scopes 2A, 2B have universal cables 10A, 10B respectively provided with light source connectors 63A, 63B which can be fitted to a connector socket 62 of the light source unit 3. Cables 64A, 64B are respectively extended from the connectors 63A, 63B and provided at their ends with electric connectors 67A, 67B which can be fitted to an electric connector socket 66 of a signal processing unit 65 separate from the light source unit 3.

The light source connector socket 62 includes contacts 69a, 69b conductively connected to contacts 68a, 68b provided in the light source connectors 63A, 63B, the contacts 69a, 69b being connected to a light source terminal and ground, respectively.

The contacts 68a, 68b are respectively conducted via signal lines 71a, 71b to contacts 72a, 72b provided in the electric connectors 67A, 67B. Those contacts 72a, 72b are each arranged to be conductively connected to a contact 73 provided in the electric connector socket 66 of the signal processing unit 65. The contact 73 is connected to a scope detecting circuit 74 which delivers a detection output depending on the type of connected scope to an inference rule selecting circuit 75 for switching groups of fuzzy inference rules in accordance with the connected scope.

Figure 10:
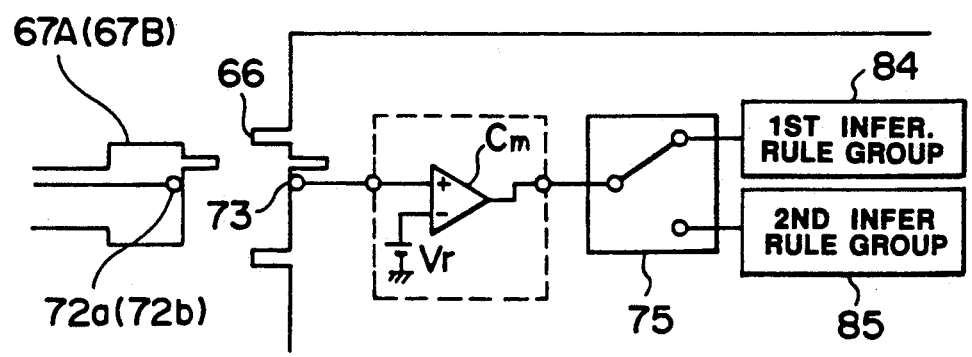

The scope detecting circuit 74 is formed by a comparator Cm as shown in FIG. 10, for example. Depending on whether the level of the contact 73 is "H" or "L", the comparator outputs a binary signal so that the inference rule selecting circuit 75 comprising a switch circuit, for example, thereby switching over between a first inference rule group 84 prepared corresponding to the scope 2A for the upper digestive tract and a second inference rule group 85 prepared corresponding to the scope 2B for the lower digestive tract. Note that, in FIG. 10, voltage Vr is set to a voltage value lower than a level of the power supply terminal.

Figure 11:
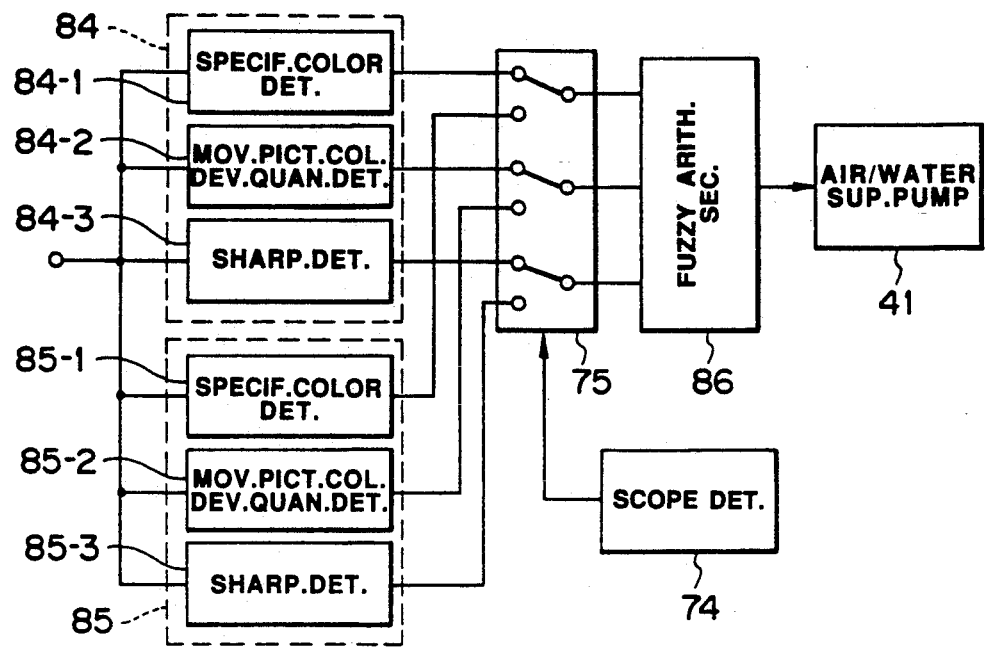

FIG. 11 shows a block diagram for air/water control using the inference rule group switchingly selected out of the inference rule groups 84, 85 by the scope detecting circuit 74. For instance, the three primary color signals R, G, B delivered from the D/A converter 32 in FIG. 1 are inputted to each of specific color detecting circuits 84-1, 85-1, moving picture color deviation quantity detecting circuits 84-2, 85-2 and sharpness detecting circuits 84-3, 85-3, which respectively constitute the first and second inference rule groups 84, 85 and, based on the input signals, detect quantities of specific color components, moving picture color deviations and sharpness set for the upper and lower digestive tracts.

Of two grouped output signals from those detecting circuits 84-1 through 85-3, only one group of detecting signals 84-1 through 84-3 or 85-1 through 85-3 are inputted to a fuzzy arithmetic section 86 and used as information signals for setting an appropriate value of the quantity of supplied air/water. Then, a control signal resulting from the fuzzy inference using those information signals is sent to the air/water supply pump 41 (see FIG. 1) to determine the quantity of supplied air/water. In short, the scope detecting circuit 74 detects whether the connected scope is for the upper or lower digestive tract, and the resulting detection signal is used to switch over the input information for the fuzzy inference.

The reason for switching over the input information will be explained below. In the case of using the scope 2A for the upper digestive tract, for example, the lens surface is stained with blood, dye or mucus. In this case, the blood is red, the dye is methylene blue or dark blue, and the mucus has a color nearly yellow. Meanwhile, in the case of using the scope 2B for the lower digestive tract, the lens surface is stained with red blood, feces or dyeing by methylene blue. Thus, because hues responsible for stains are different for both the cases, the lens stain can be certainly inferred by detecting the specific hue which accounts for the stain of each scope.

Figure 12A:
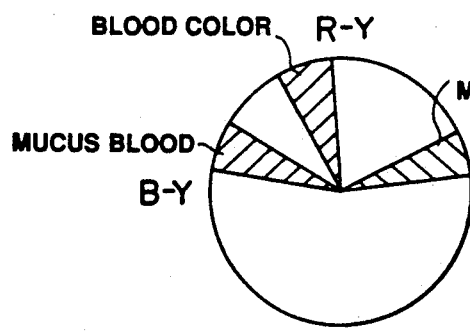
FIGS. 12(a) and 12(b) are explanatory representations showing that scopes for upper and lower digestive tracts have different specified colors.
Figure 12B:
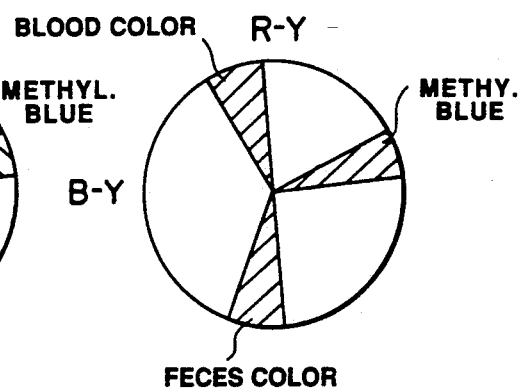

Therefore, this embodiment includes the specific color detecting circuits 84-1, 85-1 respectively provided for the scopes 2A, 2B for detecting the extent that deposits are deposited over the lens surfaces. To this end, the specific color detecting circuits 84-1, 85-1 are set to detect respective hues as shown in FIGS. 12(a) and 12(b). In practice, it is possible to extract signals of the respective hues by the matrix circuit as shown in FIG. 3, by way of example, and to add the extracted hues (or add them after weighting).

Figure 13:
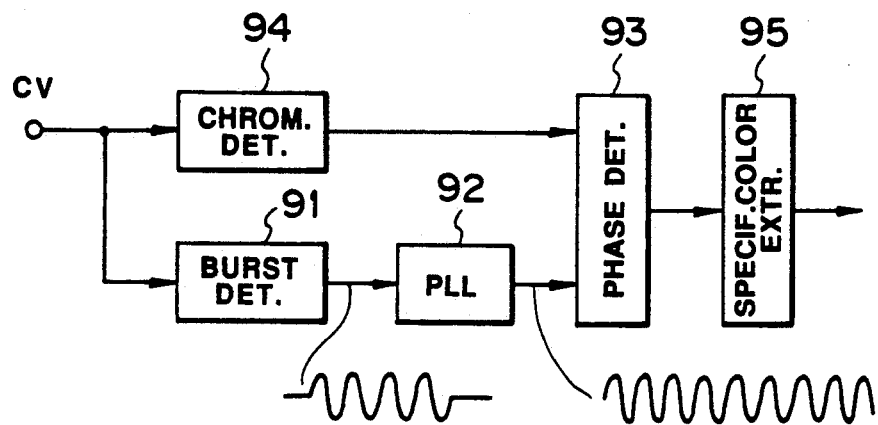
Figure 14:
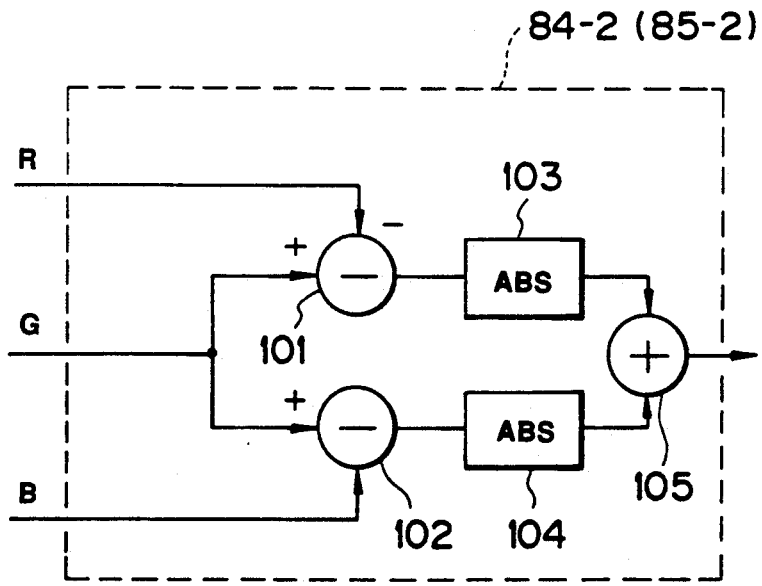

When the input signal is a composite video signal CV, the composite video signal CV is applied to a burst detecting circuit 91 to extract a burst signal, as shown in FIG. 13. The burst signal passes through a PLL circuit 92 for producing a sub-carrier signal in synchronism with the burst signal. The sub-carrier signal is compared in phase with a chroma signal of the object image extracted through a chroma detecting circuit 94, thereby detecting a phase difference between the chroma signal and the sub-carrier signal which difference is sent to a specific color extracting circuit 95. The specific color extracting circuit 95 extracts only the specific color components shown in FIG. 12 and sends specific color information to the fuzzy arithmetic section 86 shown in FIG. 11 depending on levels of the extracted components. At this time, the extracted phase regions are changed over corresponding to the scope type. One example of an arrangement of the moving picture color deviation quantity detecting circuit 84-2 or 85-2 is shown in FIG. 14.

The color signal G and the color signals R, B are inputted in pair to subtractors 101, 102, respectively, which produce difference signals after subtractions. Respective absolute values of the difference signals are obtained by absolute value circuits 103, 104 and then accumulated by an accumulator 105 for a period of one frame, for example, thereby detecting the moving picture color deviation quantity. As an alternative, the moving picture color deviation quantity may be detected using those signals which are shifted in time from each other by one frame.

The reason for using the detection of moving picture color deviation quantity as information (variable) for the inference rules is in that the color deviation of a moving picture distinctly appears when stains are removed with cleaning by the supplied air/water.

Also, the reason of switching over the inference rule groups for the moving picture color deviation quantity between the scopes for the upper and lower digestive tracts is in that the objective lens system, the number of pixels of CCD, etc. differ for each type of scope and, therefore, the detecting moving quantity becomes different even if deposits are deposited on the respective lens surfaces to the same extent. Thus, the inference rule groups are switched over so as to carry out the inference suitable for each scope. The sharpness detecting circuit 84-3 or 85-3 is further included as one of inference rules because the image becomes blurred if the lens surface is stained, and the sharp image can be provided if stains are removed.

Figure 15:
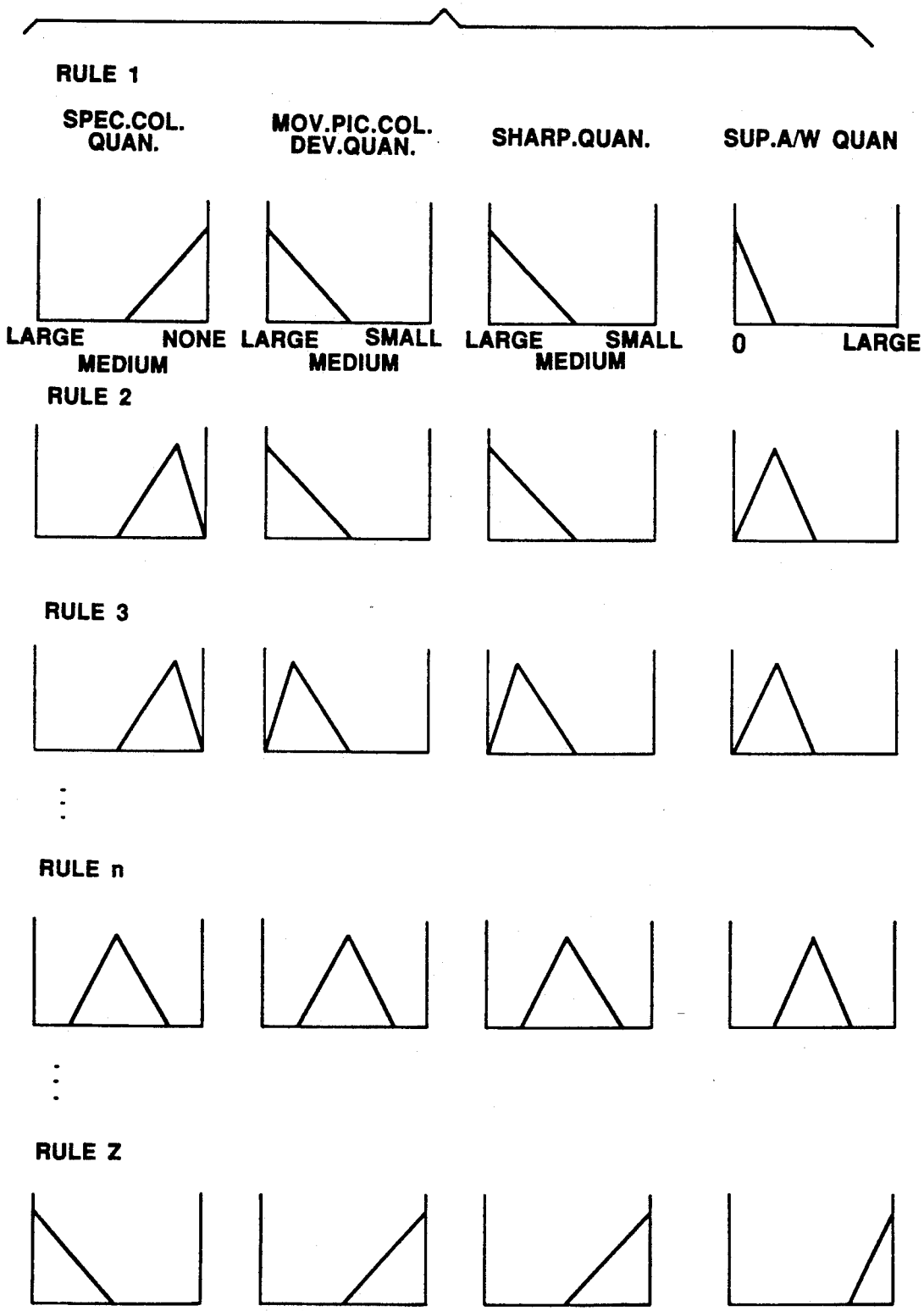

Next, FIG. 15 shows one example of membership functions and inference rules for controlling the supplied air/water quantity depending on the detected quantities of specific color, moving picture color deviation and sharpness. With the rule 1, for example, the supplied air/water quantity is set to zero if the specific color quantity is not present at all, the moving picture color deviation quantity is large, and the sharpness quantity is large. With the rule n, the supplied air/water quantity is set to medium if the specific color quantity is medium, the moving picture color deviation quantity is medium, and the sharpness quantity is medium. Practically, as to the scopes for the upper and lower digestive tracts, the setting of FIG. 15 is changed somewhat to effectively remove stains on the lens surface with the appropriate supplied air/water quantity for each scope.

With this second embodiment, even if either scope is used, the stains deposited on the lens surface can be removed with the supplied air/water quantity optimum to remove the stains without requiring skilled experience.

As shown in FIG. 16, without carrying out the inference, the air/water supply pump 41 may be alternatively controlled by a control signal CS resulted from weighting the respective outputs of the specific color detecting circuits 84-1, 85-1, the moving picture color deviation quantity detecting circuits 84-2, 85-2 and the sharpness detecting circuits 84-3, 85-3 through respective weighting circuits 106, selecting one group of the outputs through a switching circuit 107, and adding them by an adder 108. Note that the switching circuit 107 is controlled to be switched over depending on the output of the scope detecting circuit 74.

FIG. 17 shows an arrangement of primary components in a third embodiment of the present invention. In this embodiment, like the second embodiment, rule groups 114, 115 for fuzzy inference are switched over depending on the output of the scope detecting circuit 74. Moreover, in this embodiment, the scope detecting circuit 74 is also used to determine types of scopes in which treatment appliances appear at different positions in the field of view (the effective angle of field in the image sensed plane), and either the inference rule group 114 or 115 more effective in detecting the treatment appliance is used for a region including the position at which the treatment appliance appears.

The luminance signal produced by passing the signals R, G, B outputting from the D/A converter 32 in FIG. 1 through a matrix circuit, for example, is amplified by an amplifier 111, an output signal of which is applied to both a diaphragm quantity detecting circuit 112 for outputting a diaphragm control signal to control the diaphragm control circuit (20 in FIG. 1) and a region selecting circuit 113. Depending on the scope type detected by the scope detecting circuit 74, the region selecting circuit 113 produces only part of the output signal from the amplifier 111 corresponding to a particular region. Furthermore, in this embodiment, the scope detecting circuit 74 determines a scope for the duodenum and other type of scopes.

In the case of observing a drainage tube inserted through a channel of the duodenum scope, an endoscope image is presented such that an image 78 of the drainage tube appears in the fourth quadrant, as shown in FIG. 18(a). Meanwhile, in the case of observing a forceps adapted to inspect living bodies, for example, inserted through the channel using another type of scope, an endoscope image is presented such that an image 79 of the forceps appears in the third quadrant, as shown in FIG. 18(b).

When those treatment appliances appear in the endoscope image, the device operates as follows. For instance, when the drainage tube appears, because it is white and has high reflectance, the device equipped with a usual automatic light adjusting function adjusts the image to become dark. In the case of the forceps, because the forceps have luster peculiar to metal, the device is affected in a different manner from the case of the drainage tube.

For reliably detecting (determining) the type of treatment appliance, in this embodiment, if the duodenum scope is determined depending on the output of the scope detecting circuit 74, the region selecting circuit 113 is operated to use only the signal in the fourth quadrant, thereby detecting the drainage tube 78. If another type of scope is determined, the signal in the third quadrant is used to detect the treatment appliance.

The signal in the region selected by the region selecting circuit 113 is inputted to the inference rule selecting circuit 75 to select one of two inference rule groups 114, 115, the selected group being inputted to a fuzzy arithmetic section 116. The two inference rule groups 114, 115 each include a peak detecting circuit, an average value detecting circuit, an edge detecting circuit, a peak width detecting circuit and a peak length detecting circuit, for example. Respective outputs of those circuits are inputted to the fuzzy arithmetic section 116 where fuzzy inference is carried out using information outputted from those circuits to reliably detect the drainage tube or the usual treatment appliance.

In this way, the fuzzy arithmetic section 116 outputs an inferred result to a diaphragm quantity detecting circuit 112 so that a loop time constant and a highlight cut level of the diaphragm quantity detecting circuit 112 are controlled via a time constant control circuit 117 and a peak clip level control circuit 118, respectively. Thus, depending on the inferred result, i.e., the degree or probability of the treatment appliance detected with the inference, the loop time constant is set and the highlight level is cut in the process of diaphragm quantity control to thereby perform diaphragm control, that is, light adjustment, suitable for the treatment appliance inferred.

While the above third embodiment has been explained as controlling the diaphragm quantity with fuzzy inference, an alternative arrangement shown in FIG. 19 is also feasible. More specifically, the output signal of the amplifier 111 is passed through each of an edge detecting circuit 131, a peak width detecting circuit 132 and a peak length detecting circuit 133 to respectively detect an edge, a peak width and a peak length, by way of example, which are applied to threshold circuits 134, 135, 136 set to respective appropriate threshold levels. Three outputs of information exceeding the respective setting levels are ANDed by an AND circuit 137. An identification means for determining (identifying) the fact that the treatment appliance is a special one is thus hardware-implemented and, depending on a determined result, the light adjustment control is switched over in setting of the loop time constant and the highlight cut level for the diaphragm control to be suitable for the special treatment appliance identified.

A modification of the third embodiment of the present invention will now be described. In the above third embodiment, the scope detection is carried out and the resulting output signal is utilized to switch over not only the inference rule group, but also the image region to which the selected inference rule group is applied. However, this modification is designed to perform an appropriate light adjustment with fuzzy inference based on plural information derived from the image signal even if such a special treatment appliance as having high reflectance, in particular, is used.

Figure 20:
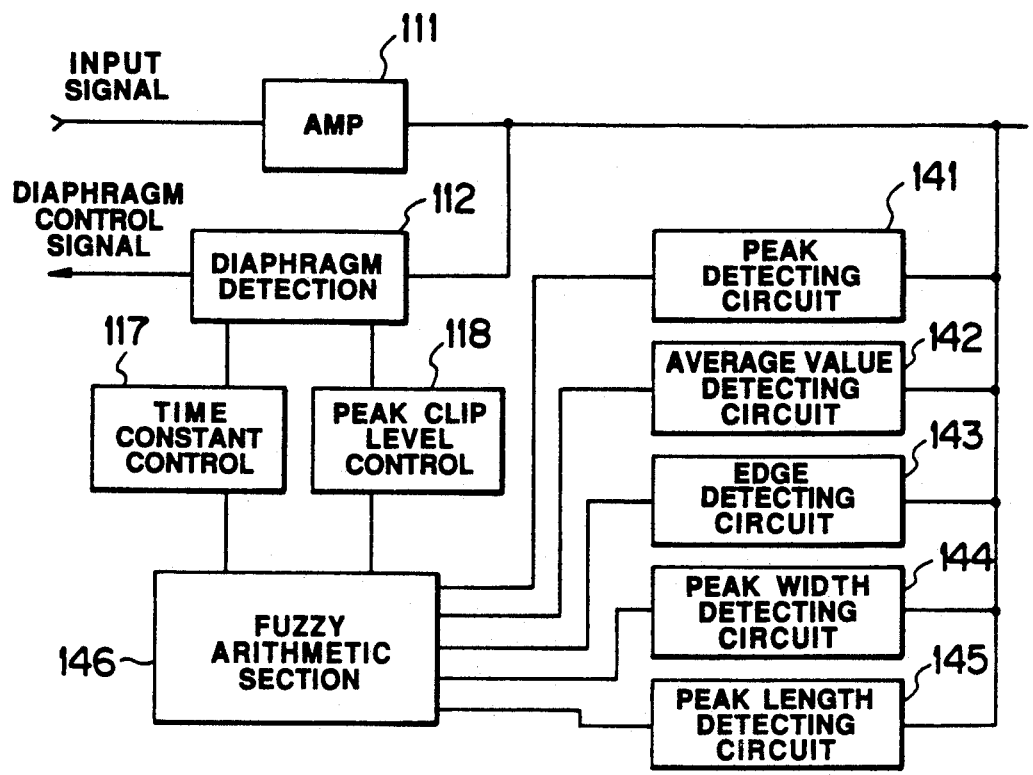

FIG. 20 shows an arrangement of primary components of this modification. The luminance signal in the CCD output signal is amplified by the amplifier 111 and then inputted to the diaphragm quantity detecting circuit 112, as well as each of a peak detecting circuit 141, an average value detecting circuit 142, an edge detecting circuit 143, a peak width detecting circuit 144 and a peak length detecting circuit 145 for detecting a peak value, average value, edge, peak width and peak length, respectively. Thus, in addition to usual detection of the diaphragm quantity, there is further provided a means for detecting features of a special treatment appliance.

Generally, features cited hereinafter occur when a special treatment appliance having high reflectance, such as a drainage tube for draining bile or a cannulation tube for injecting a contrast medium, enters the effective angle of field.

a. the bright spot has a level several or more times higher than that of a normal object; b. the bright spot has a width narrower than halation occurred in a normal object, but not so fine, while presenting the continuous form; and c. the position in the image where the special treatment appliance appears can be substantially located based on the function of the scope and the rational placement of its distal end.

In view of the above, this modification is designed such that (a) the peak detecting circuit 141 detects a peak level in the image, (b) the average value detecting circuit 142 detects an overall level of the image, (c) the edge detecting circuit 143 detects whether or not the edge is relatively sharp in its profile, (d) the peak width detecting circuit 144 detects a peak width, and (e) the peak length detecting circuit 145 detects a peak length.

Respective output signals of the above detecting circuits 141 through 145 are applied to a fuzzy arithmetic section 146 to determine whether the special treatment appliance is present or absent in the effective angle of field, by using those signals as information for fuzzy inference. Depending on the resulting inference, the fuzzy arithmetic section 146 controls a loop time constant and a highlight cut level of the diaphragm quantity detecting circuit 112, which outputs the diaphragm control signal, via the time constant control circuit 117 and the peak clip level control circuit 118, respectively, so that an appropriate light adjustment may be carried out even if the special treatment appliance is present in the effective angle of field.

The fuzzy arithmetic section 146 implements the fuzzy inference by a sequence of "MIN"-"MAX"-"centroid" process explained above in connection with FIG. 6, by way of example. In this modification, inference rules for use in the fuzzy inference are set based on membership functions as shown in FIG. 21. In FIG. 21, the rule 1 shows one typical example of an inference rule in the control suitable for the special treatment appliance such as a drainage tube.

Further, the rule 2 shows a typical example of an inference rule in a standard image condition corresponding to the normal image. The rule 3 shows one typical example of an inference rule adapted for the case that halation occurs in part of the normal image. In each rule, former five items from (a) to (e) represent membership functions of the antecedent portion, and the last (f) represents a membership function of the consequent portion, thereby setting optimum control of the highlight cut level and the loop time constant.

With the rule 1, if the width of the peak level is medium, the length of the peak level is medium and the edge level is relatively high, the special treatment appliance is determined to be present in the effective angle of field, whereupon the highlight cut level is lowered and the time constant is prolonged to make control such that the diaphragm quantity will not be changed under an influence of the bright point.

Conversely, in the case of an image where halation occurs in part of the normal object image as represented by the rule 3, the peak level has a relatively wide width and a long length. Also, in the case like this, since the edge is not so sharp, the highlight cut is not performed the time constant is set to be short for ensuring appropriate brightness at a prompt response.

With this modification, if the special treatment appliance is present in the effective angle of field, the signals corresponding to its features are detected by the respective detecting circuits 141 through 145. Therefore, by causing the fuzzy arithmetic section 146 to carry out the fuzzy inference using those signals as input information, the presence of the special treatment appliance can be detected reliably. Also, the appropriate light adjusted condition can be maintained with like the diaphragm control of effecting the highlight cut or setting the longer time constant. In other cases, too, the appropriate light adjusted condition can also be maintained based on the fuzzy inference.

This modification can be practiced through software implementation, not to speak of hardware implementation, because a prompt determination is not required. In addition, the above arithmetic operations may be processed using an ordinary computer, but this raises a problem below. If such a computer is used to execute the above arithmetic operations in agreement with conditions of the antecedent portion, a great deal of operation quantity would be required, the size of scale of the device itself would be increased, and a very high-speed computer would be needed. In contrast, the use of fuzzy operation has advantages of making the device size smaller and the process complete in a shorter period of time.

Figure 22:
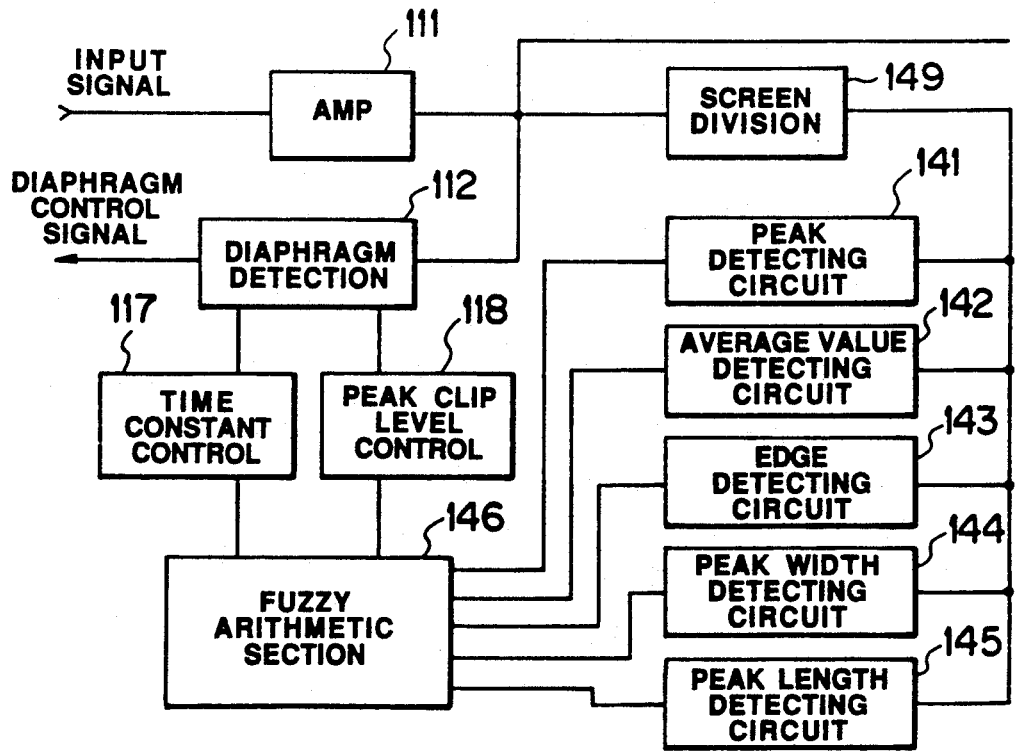
FIG. 22 is a block diagram of primary components in another modification of the third embodiment.

FIG. 22 shows another modification of the third embodiment. In this modification, the output signal of the amplifier 111 is passed through an image dividing circuit 149 and then inputted to the peak detecting circuit 141, etc. When the treatment appliance appears in a certain determined quadrant of the angle of field as shown in FIG. 18, the image dividing circuit 149 serves to cause the fuzzy operation to be carried out using only the image signal of that quadrant, with an expectation of improving the detection accuracy. The remainder of this modification is the same as FIG. 20.

In the above case, for instance, if the fuzzy inference is made on the image signal of the fourth quadrant to detect the presence or absence of the special treatment appliance, and the appliance is decided to be absent, the fuzzy inference may be further made on the image signal of the third quadrant.

As an alternative, the fuzzy inference may be carried out on both the signals of the third and fourth quadrants. It is also possible to provide a scope detecting means as in the third embodiment and, depending on the scope detection, to perform the fuzzy inference on the image signal of the fourth or third quadrant.

Incidentally, the diaphragm control may be performed through hardware implementation as shown in FIG. 19, by way of example, without resorting to the fuzzy inference. In this case, however, because the decision reference is set to "0" or "1" and intermediate decision enabled by the fuzzy inference is not allowed, the accuracy of control itself is decreased. The control using the fuzzy inference is also superior on this point.

Figure 23:
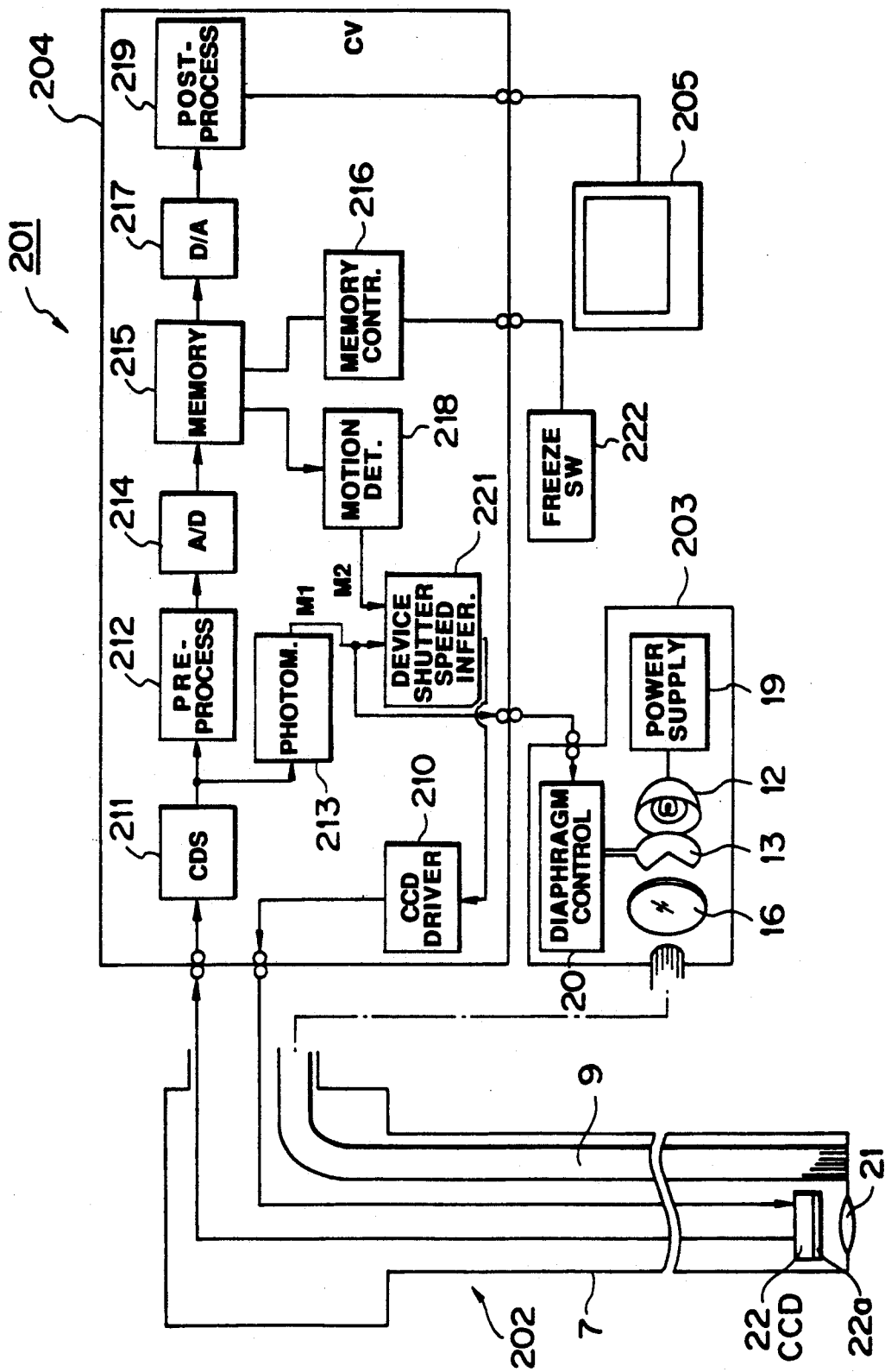

FIG. 23 shows an arrangement of primary components of a fourth embodiment of the present invention. This embodiment is directed to an endoscope device 201 of a synchronous type (that provides a color image under illumination of white light).

The endoscope device 201 comprises a synchronous type electronic scope 202, a light source unit 203 for supplying white illumination light to the electronic scope 202, a signal processing unit 204 to carry out signal processing for the electronic scope 202, and a color monitor 205 for displaying an image of an object.

The electronic scope 202 as a CCD 22 provided with a color mosaic filter 22a in the focal plane of the objective lens 21 in the electronic scope 2 of FIG. 1. The remaining components are the same as shown in FIG. 1 (for sake of simplicity, however, the channel 45 and others shown in FIG. 1 are omitted in FIG. 23), and the same components as those in FIG. 1 are designated by the same reference numerals. The light source unit 203 is a modified version of the light source unit 3 in FIG. 1 in which white light from the lamp 12 is irradiated to the incident end face of the light guide 9 via the diaphragm 13 and the condenser lens 16.

An image of an object illuminated by the white light, which is transmitted through the light guide 9 and emitted from the distal end face of the insert section 7, is focused by the objective lens 21 on the CCD 22 disposed in its focal plane. At this time, the white light is subjected to color separation by the color mosaic filter 22a. An image signal read out of the CCD 22 upon application of a drive signal from a CCD driver 210 thereto is inputted to a CDS (Correlation Double Sampling) circuit 211 where reset noise or the like is removed away and the image signal is demodulated to the base band, followed by entering both a pre-process circuit 212 and a photometric circuit 213.

The signal subjected to gamma correction, white balance adjustment, etc. by the pre-process circuit 212 is converted to a digital signal by an A/D converter 214, where the digital signal being inputted to a memory 215. The memory 215 is controlled by a memory controller 216 so that the signal data written into the memory 215 is inputted to both a D/A converter 217 and a motion detecting circuit 218. The digital signal is converted into an analog signal by the D/A converter 217, following by superposition of a synchronizing signal, etc. in a post-process circuit 219 to produce a standard composite video signal CV. The composite video signal CV is inputted to the color monitor 205 for displaying the image of the object in colors.

On the other hand, the photometric circuit 213 produces from an output signal of the CDS signal 211, e.g., a luminance signal, a signal corresponding brightness of the image of each frame and then delivers it to both a device shutter speed inferring section 221 and the diaphragm control circuit 20. The diaphragm control circuit 20 changes a rotational angle of the diaphragm 13 for changing the intensity of light passing therethrough to make a light adjustment so that brightness of the image of each frame becomes an appropriate value.

The motion detecting circuit 218 obtains an absolute value of a difference signal between every two luminance signals shifted from each other by one frame/field, for example, to detect a motion quantity between the images shifted from each other by one frame/field, and then delivers a motion signal corresponding to the detected motion quantity to the device shutter speed inferring section 221.

Applied to the device shutter speed inferring section 221 are a photometric signal M1 from the photometric circuit 213 and a motion signal M2 from the motion detecting circuit 218. Using these two sorts of input information as membership functions of the antecedent portion, the device shutter speed inferring section 221 performs the fuzzy inference for speed of a device shutter as the consequent portion and outputs a resulting control signal to the CCD driver 210. Upon receiving the control signal, the CCD driver 210 outputs a CCD drive signal to the CCD 22 at the speed of the device shutter corresponding to the control signal.

There will now be explained the fuzzy inference performed in the device shutter speed inferring section 221.

In this embodiment, a fuzzy scale for brightness is expressed in three stages; i.e., the photometric result is a. light, b. medial, and c. dark.

Also, a fuzzy scale for motion speed is expressed in three stages; i.e., the motion is a. fast, b. medial, and c. slow.

Furthermore, a fuzzy scale for speed of the device shutter as the consequent portion is expressed in five stages; i.e., the shutter speed is at a. high speed, b. medium high-speed, c. medium speed, d. medium low-speed, and e. low speed.

This embodiment adopts, as fuzzy rules, nine rules listed in Table 2 below.

TABLE 2

| Rule | Bright-ness | | Motion speed | | Shutter speed |
|---|---|---|---|---|---|
| 1 | light | | fast | | high speed |
| 2 | light | | medial | | medium high-speed |
| 3 | light | | slow | | medium speed |
| 4 | medial | and | fast | then | medium high-speed |
| 5 | medial | | medial | | medium speed |
| 6 | medial | | slow | | medium low-speed |
| 7 | dark | | fast | | medium speed |
| 8 | dark | | medial | | medium low-speed |
| 9 | dark | | slow | | low speed |

Figure 24:
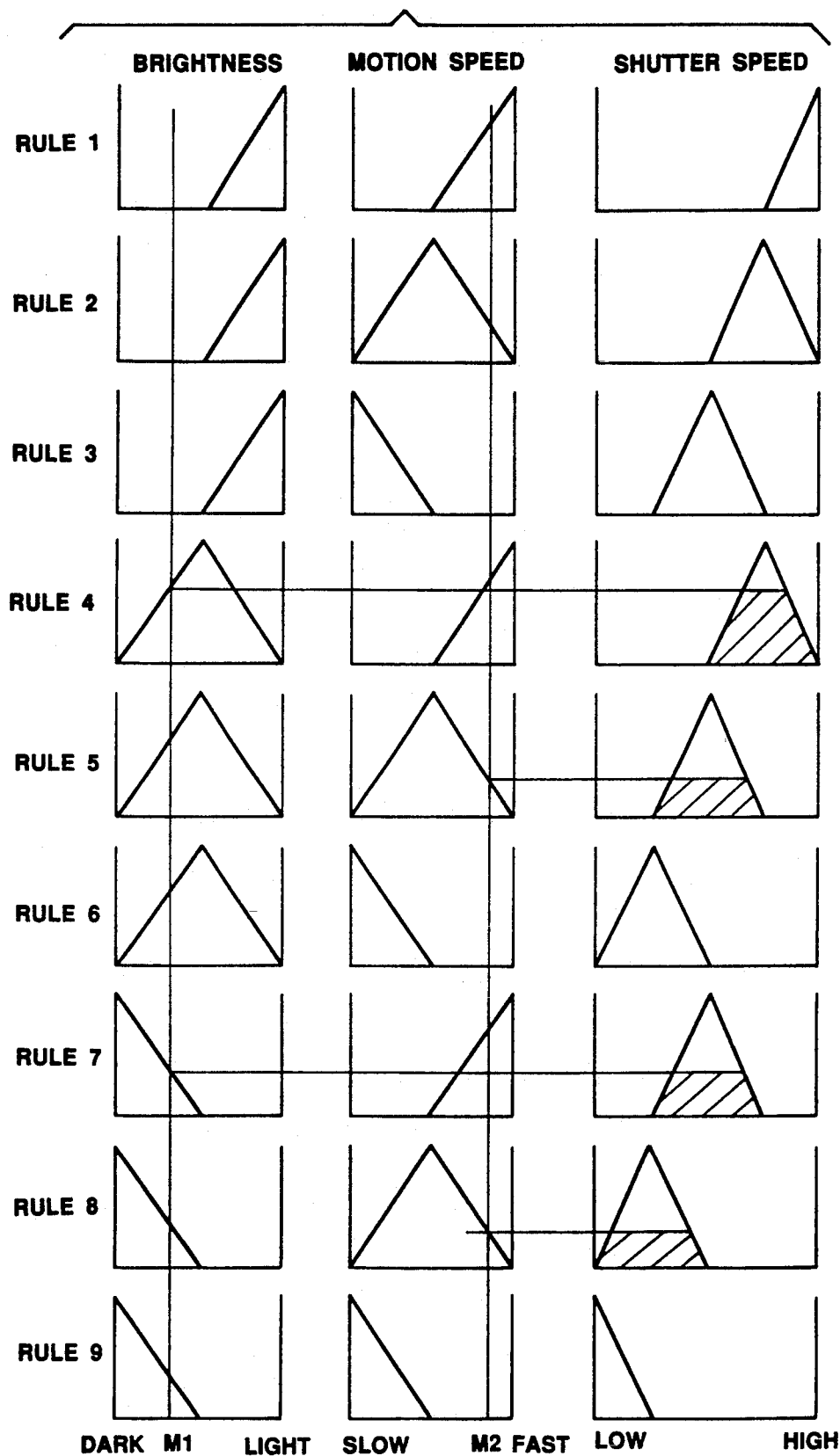
Figure 25:
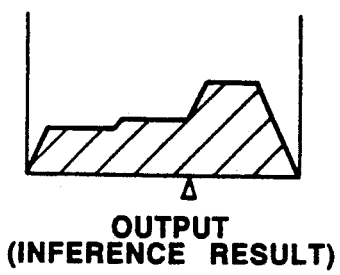

The above nine rules can be expressed as shown in FIG. 24 using membership functions. Receiving the photometric signal M1 from the photometric circuit 213 and the motion signal M2 from the motion detecting circuit 218 as inputs, the device shutter speed inferring section 221 applies the above nine rules simultaneously to obtain degrees of the antecedent portions of all the rules for the respective inputs with MIN operations, then applies those degrees to the consequent portions of the rules for obtaining respective elements, indicated by hatched areas, to specify the shutter speed. A MAX operation is made on the hatched areas to obtain a centroid value of the function resulted from synthesizing the consequent portions of all the rules, as shown in FIG. 25 by way of example, the centroid value being an output value to determine the shutter speed. Then, after a freeze signal issued upon turning-on of a freeze switch 222 comprising a foot switch, for example, is inputted to the memory controller 216 shown in FIG. 23, the speed of the device shutter is automatically changed depending on the output value so that a proper still picture may be provided under conditions of image blur and brightness which contradicts each other.

Stated otherwise, although there has also existed in the past an endoscope device with a function of the device shutter able to present a still picture, it is designed to manually switch over the speed of the device shutter. Therefore, if the speed of the device shutter is set to be too fast, the intensity of illumination light becomes insufficient; resulting in a dark image. If too slow, the image blur cannot be totally eliminated so as to present a sharp image.

In contrast, this embodiment carries out the fuzzy inference using the brightness and motion quantity of the image as input information, whereby the speed of the device shutter is controlled over a short period of time to present an endoscope image with less image blur and brightness expedient for diagnosis. Accordingly, in the case of obtaining the endoscope image in the form of a still picture used to make a diagnosis in situ or filed in a recording unit for purpose of later detailed diagnosis, for example, there can be provided a sharp image more expedient for diagnosis.

Figure 26:
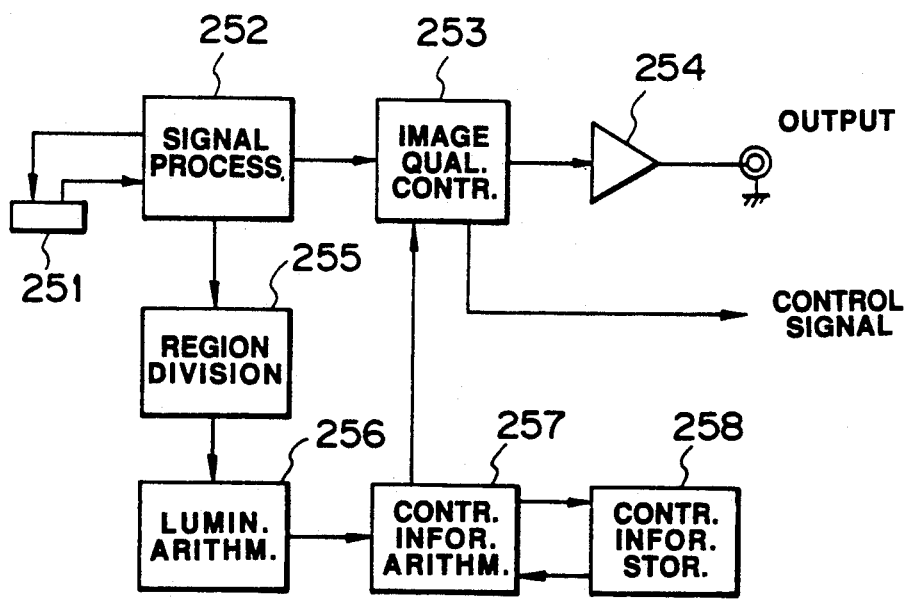

FIG. 26 shows a conceptual arrangement of a fifth embodiment of the present invention. An output signal of an image sensing device 251 is processed by a signal processing circuit 252 and, thereafter, issued from an output terminal via an image quality control means 253 for performing image control and then a video amplifier 254.

An output signal of the signal processing circuit 252 is divided into plural regions by a region dividing means 255 for dividing the image field sensed. Luminance is derived by a luminance arithmetic means 256 for each of the divided regions, followed by calculating average and maximum values of the luminance. An output of the luminance arithmetic means 256 is delivered to a control information arithmetic means 257 which performs fuzzy inference for image quality control using the average and maximum values of the luminance. At this time, the control information arithmetic means 257 refers to information stored in a control information storage means 258, and outputs a final result of the fuzzy inference to an image quality control means 253. The image quality control means 253 outputs a control signal for image quality control to a diaphragm control means in a light source unit, for example, thereby carrying out the image quality control.

Figure 27:
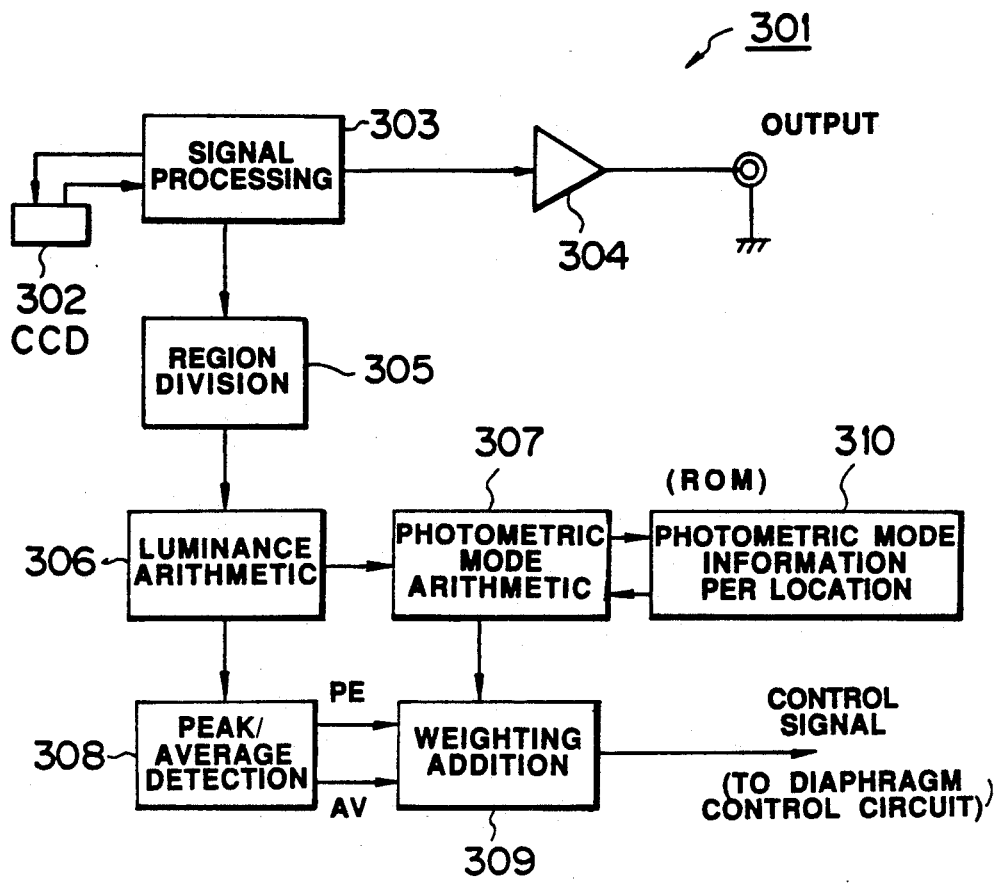

FIG. 27 shows an arrangement of primary components in an endoscope device 301 of the fifth embodiment of the present invention.

Figure 28:
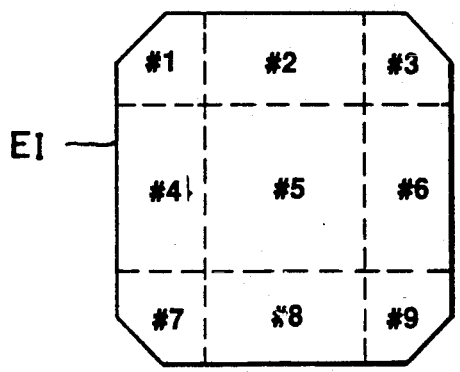

An output signal of a CCD 302 is applied to and processed by a signal processing circuit 303 and, thereafter, is issued from an output terminal via a video amplifier 304. An output signal of the signal processing circuit 303 is applied to a region dividing circuit 305 where an endoscope image is divided into plural regions. FIG. 28 shows one example of a division manner in which the region dividing circuit 305 divides an endoscope image EI into nine divisional images (regions) #1 through #9.

Output signals respectively corresponding to the divisional images divided by the region dividing circuit 305 are applied to a luminance arithmetic circuit 306 which detects luminance information for the respective regions, the luminance information being sent to both a photometric mode arithmetic circuit 307 and a peak/average detecting circuit 308. The peak/average detecting circuit 308 derives a peak value PE and an average value AV from each luminance information, and delivers those values to a weight adding circuit 309.

The photometric mode arithmetic circuit 307 carries out fuzzy inference to determine, from the luminance information for each image region, the degree that the object corresponds to which location of the divided regions, and also reads weighting information corresponding to the inferred location out of a photometric mode information storage circuit 310. The weighting information is used for a weighting process in the weight adding circuit 309, thereby producing a final control signal for diaphragm control.

FIG. 29 shows membership functions for use in handling the luminance information, i.e., the input variables to the photometric mode arithmetic circuit 307, as a fuzzy set.

FIG. 30 shows fuzzy inference rules employed in the case of observing the stomach corner. A typical endoscope image resulting from observing the stomach corner is featured in that, as shown in FIG. 31(a), a highlight area (stomach corner) appears from the upper right to the lower left in the image field. Correspondingly, the inference rule is set such that if the regions #3, #5 and #7 are light and the other regions #1, #2,

4, #6, #8 and #9 are dark in FIG. 30, the photometric mode is set to nearly peak photometry so as to make an exposure matched with the stomach corner.

Figure 32:
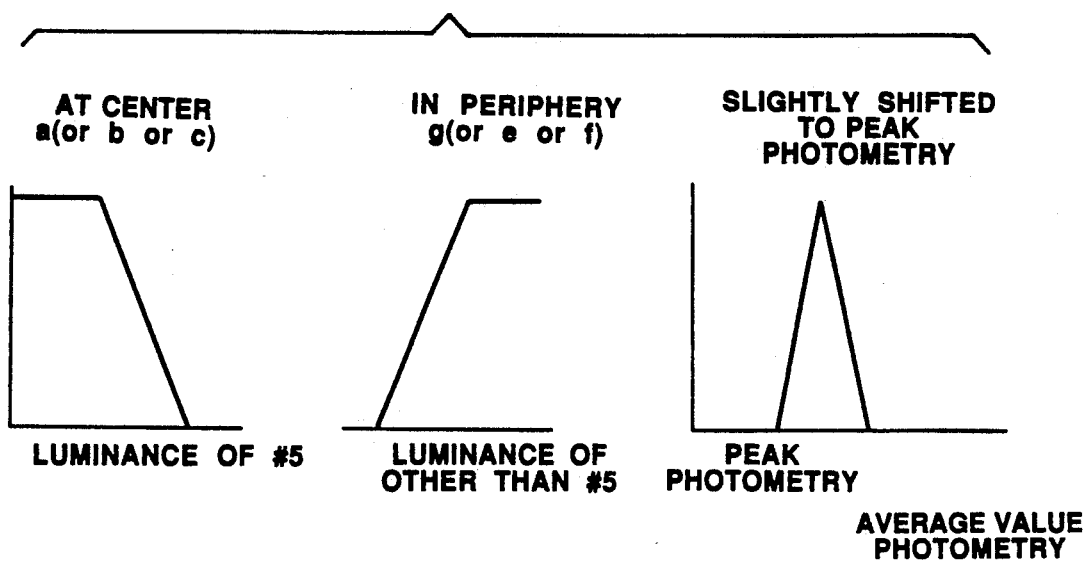

FIG. 31(b) shows a typical feature of dark/light distribution of an endoscope image resulted from observing the gullet. In this case, the central area is light and the peripheral area is dark. Therefore, the inference rule for observation of the gullet is set as shown in FIG. 32. Thus, if the central region #5 is light and the other regions are dark, the photometric mode is set to be slightly shifted to peak photometry so that the gullet is illuminated under the brightness expedient for observation.

Figure 33:
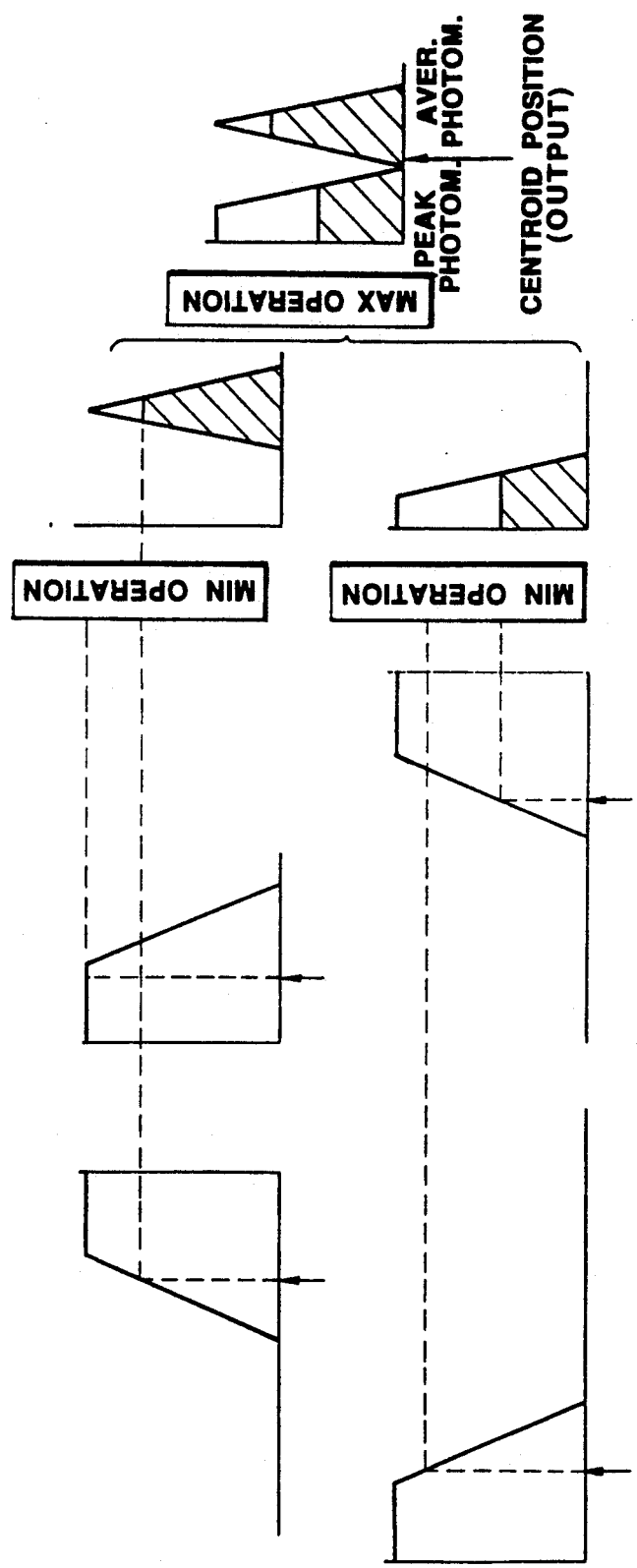

A general sequence of "min-max" processing is carried out using the aforementioned inference rules to obtain respective output values for determining the photometric mode, and these output values are synthesized by a "centroid process" to provide an inference result, as shown in FIG. 33. While this embodiment has been explained as using two typical types of inference rules, the device is designed in practice to set an arbitrary number of inference rules depending on the observed locations and to synthesize the respective output values to provide the inference result.

With this embodiment, as described above, since the fuzzy inference is carried out by setting an inference, rule corresponding to and suitable for each observed location, it is possible to perform the diaphragm control optimum for each observed location. Accordingly, there can be obtained an endoscope image with appropriate brightness in the location to be diagnosed, and the endoscope device very useful in making a diagnosis.

Although the above embodiment adopts the photometric control method to add weights to the detected peak and average values, the present invention is limited to that embodiment. For simplification, for example, the peak and average value photometry modes may be simply switched over, or the photometry may be performed with a focus given to a certain region.

Figure 34:
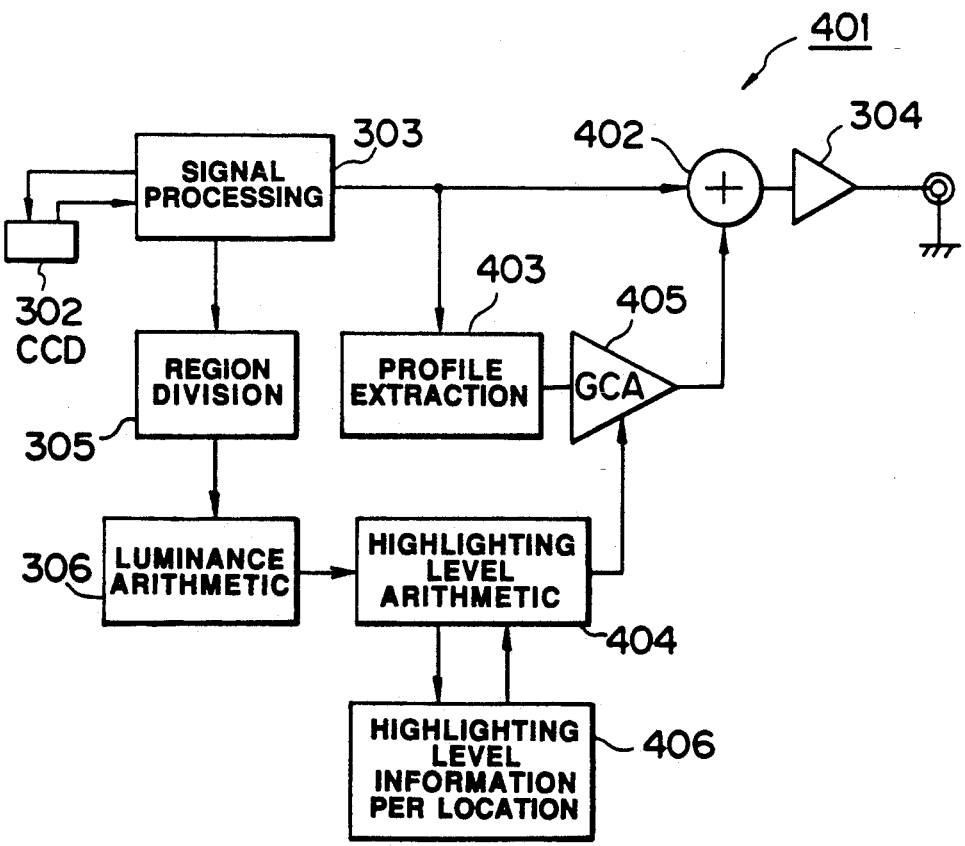
FIG. 34 is a block diagram of primary components in a sixth embodiment of the present invention.

FIG. 34 shows an arrangement of primary components in an endoscope device 401 of a sixth embodiment of the present invention. Note that the same components as those in FIG. 27 are designated by the same reference numerals.

In this embodiment, fuzzy inference is made to control profile highlighting to be performed in such a manner as suitable for each observed location even if the locations to be observed are different.

The output signal of the signal processing circuit 303 is, as with the embodiment of FIG. 27, applied to the luminance arithmetic circuit 306 via the region dividing circuit 305. Also, the output signal of the signal processing circuit 303 is delivered from an output terminal via an adder 402 and the video amplifier 304. The output signal of the signal processing circuit 303 is further applied to a profile extracting circuit 403 formed of a delay line or the like. A profile signal component extracted by the profile extracting circuit 403 is amplified by a gain variable amplifier 405 of which gain is controlled depending on an output signal from a highlighting level arithmetic circuit 404, and then applied to the adder 402 for addition to the output signal of the signal processing circuit 303.

Applied to the highlighting level arithmetic circuit 404 are the luminance information for the respective divided regions outputted from the luminance arithmetic circuit 306. The highlighting level arithmetic circuit 404 determines, from the luminance information for each image region, the degree that the object corresponds to which location of the divided regions, and also reads profile highlighting levels for the respective locations out of a highlighting level information per location storage circuit 406. The read-out profile highlighting levels are weight averaged depending on the above degrees to determine a final profile highlighting level. Such an arithmetic process can be implemented with fuzzy inference in a like manner to the sixth embodiment.

With this embodiment, for example, it is possible to automatically set the highlighting level to be somewhat strong in the case of viewing the walls of the stomach from in front which case requires close observation of surface tissues, or set it to be somewhat weak in the case of observing the great intestine to suppress a rough texture of the dark area.

The aforementioned embodiments may be combined to constitute other different embodiments which also belong to the present invention. Further, the present invention is similarly applicable to an attachment type endoscope in which a TV camera having an image sensing device such as a CCD built therein is fitted to a fiber scope, instead of the electronic scope.

According to the present invention, as described above, since the fuzzy inference is carried out using a plurality of information produced from the image signal picked up by the image sensing means to thereby make control, there can be provided the endoscope image expedient for diagnosis.

Next, an automatic insertion device capable of automatically inserting an insert into bent body cavities will be described. This automatic insertion device permits an endoscope insert section to be inserted in place with a simple construction.

Figure 35:
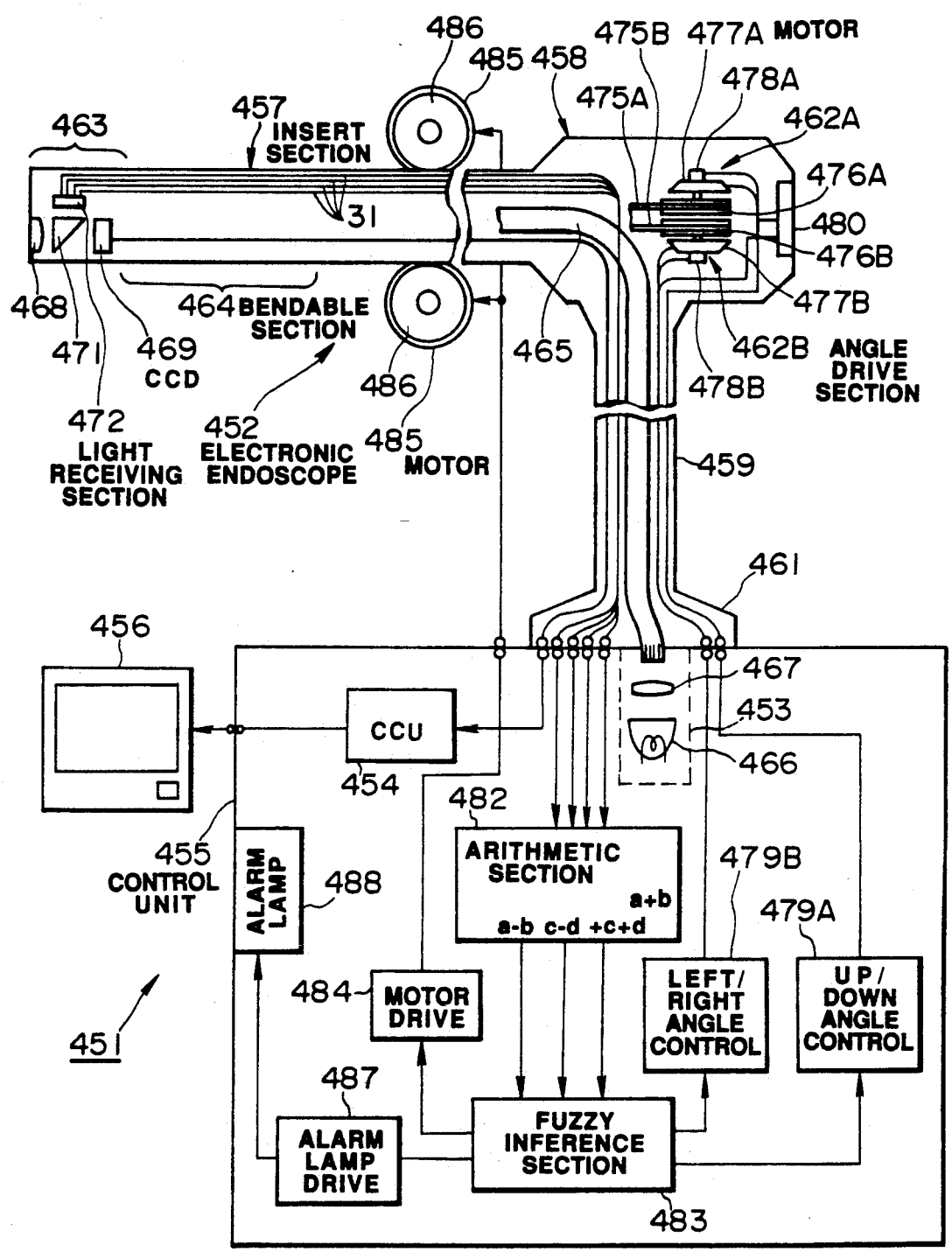

FIG. 35 shows an arrangement of an automatic insertion device 451 (for endoscopes) of a seventh embodiment which includes the fuzzy inference means as stated above.

The automatic insertion device 451 comprises an electronic endoscope 452 provided with an image sensing means, a control unit 455 incorporating a light source section 453 for supplying illumination light to the electronic endoscope 452 and a signal processing section (called also a camera control unit and abbreviated as CCU hereinafter) 454 for processing signals, and a color monitor 456 for displaying a video signal from the CCU 454.

The electronic endoscope 452 has an slender, flexible insert section 457 which is formed at its rear end with a thick operating section 458. A universal cord 459 is extended from the operating section 458, and a connector 461 attached to the distal end of the universal cord 459 can be fitted to the control unit 455 in a detachable manner.

The operating section 458 includes angle drive sections 462A, 462B for the up and down directions and the left and right directions, respectively. By controlling these angle drive sections 462A, 462B, a bendable section 464 formed adjacent to a distal end component 463 of the insert section 457 can be bent in the up/down directions and the left/right directions, etc.

A light guide 465 allowing illumination light to transmit therethrough is penetrated through the insert section 457 and the universal cord 459. When the connector 461 is connected to the control unit 455, the illumination light is supplied to an incident end face of the light guide 465. Thus, a beam of white light emitted from a light source lamp 466 is condensed by a condenser lens 467 and irradiated to the incident end face of the light guide 465. The illumination light transmitted by the light guide 465 is emergent from an opposite end face on the side of the distal end component 463 to illuminate an object.

An optical image of the illuminated object is focused by an objective lens 468, provided in the distal end component 463, on a CCD 469 disposed in the focal plane of the objective lens 468.

The optical image is subjected to photoelectric conversion by the CCD 469 and temporarily stored therein in the form of signal charges. The stored electric signal is read out by a drive signal from a drive circuit (not shown) in the CCU 454, and processed by a signal processing circuit in the CCU 454 to be converted into a standard video signal so that the image of the object is displayed on the color monitor 456 in colors.

A beam splitter such as a half prism 471 is disposed in an optical path between the objective lens 468 and the CCD 469, and reflects part of the light entering through the objective lens 468 to a light receiving section 472.

The light receiving section 472 comprises four-divided light receiving elements 472a, 472b, 472c, 472d, as shown in FIG. 36(A) or 36(B), the light receiving elements 472a, 472b being arranged corresponding to the up/down bending direction, the light receiving elements 472c, 472d being arranged corresponding to the left/right bending direction. In other words, the light receiving elements 472a, 472b are arranged along direction that is expected identical to the vertical direction in the image produced by the CCD 469, while the light receiving elements 472c, 472d are arranged along a direction perpendicular to the vertical direction. The above expected direction coincides with a direction in which the bendable section 464 is bent by the angle drive section 462A.

The angle drive sections 462A, 462B respectively comprise pulleys 476A, 476B around which angle wires 475A, 475B are wound, motors 477A, 477B for rotatively driving the pulleys 476A, 476B, and rotary encoders 478A, 478B for detecting quantities of rotation of the motors 477A, 477B. Thus, when the motor 477A is rotated forwardly, for example, one end of the wire 475A is pulled and the other end thereof is loosened to bend the bendable section 464 in the vertical direction.

The motors 477A, 477B are respectively connected to up/down and left/right angle control circuits 479A, 479B so that their operations are controlled by the up/down and left/right angle control circuits 479A, 479B.

The motors 477A, 477B are energized by a bend operating switch 480 so as to bend the bendable section 464 in a desired direction via the up/down and left/right angle control circuits 479A, 479B.

An output signal of the light receiving section 472 used to detect the insert direction for the purpose of automatic insertion is inputted to an arithmetic section 482 via a signal cable 481.

The arithmetic section 482 calculates and outputs a total signal (a+b+c+d) of the four light receiving elements 472a, 472b, 472c, 472d, as well as difference signals a-b and c-d between pairs of the light receiving elements 472a, 472b and 472c, 472d respectively arranged in the up/down direction and the left/right direction.

The total signal (a+b+c+d) and the difference signals a-b, c-d are inputted to a fuzzy inference section 483 which produces control signals for angle control of the angle drive sections 462A, 462B from those three signals, thereby bending the distal end side of the insert section 457 depending on the bent state of an insertion route to permit automatic insertion.

Output signals of the fuzzy inference section 483 are inputted to the up/down and left/right angle control circuits 479A, 479B for angle control, and also inputted to a (movement) motor drive circuit 484 for controlling motors 485, 485 to respectively control rotation/stop of pulleys 486, 486 held in abutment against the insert section 7.

Another output of the fuzzy inference section 483 is used to control an alarm lamp 88 to blink or flash on and off via an alarm lamp drive circuit 487. The following is an explanation of the angle control in the up/down direction, by way of example, effected by the fuzzy inference section 483. Based on the outputs of the arithmetic section 482, that is, the total signal (a+b+c+d) and the difference signal a-b, the fuzzy inference section 483 basically carries out the angle control in the up/down direction and the on/off control of the alarm lamp as shown in Table 3 below.

TABLE 3

| Rules | a + b + c + d | a-b | Angle control | Alarm lamp |
|-------|---------------|-------|---------------|------------|
| I | light | plus | down | off |
| II | light | 0 | as it is | on |
| III | light | minus | up | off |
| IV | dark | plus | down | off |
| V | dark | 0 | as it is | off |
| VI | dark | minus | up | off |

The method of the angle control represented by Table 3 can be expressed as shown in FIG. 37, by way of example, in the form of membership functions.

In FIG. 37, for example, I represents a control rule that if the total signal (a+b+c+d) is light and the difference signal a-b is plus (positive), the angle control is effected in the downward direction and the alarm lamp is not lighted.

The control rule I shown in Table 3 corresponds to a condition of FIG. 38.

When a body cavity 491 into which the distal end of the insert section 457 is inserted is bent downwards toward a deeper portion and the distal end of the insert section 457 is not directed downwards, the illumination light from the light guide 465 cannot reach the deeper portion, or the reflected light from the deeper portion is weak, the output of the light receiving element 472b on which an opening area facing the deeper portion is focused becomes smaller than the output of the light receiving element 472a.

In this case, therefore, the angle control is effected in the downward direction so that the distal end of the insert section 7 is controlled to direct the opening deeper portion. At the same time, since the distal end of the insert section 457 is not about to abut against the wall surface of the body cavity, the alarm lamp 488 is not lighted.

On the other hand, the control rule represented by II is considered to correspond to a condition that the distal end of the insert section 457 confronts the wall surface of the body cavity, and may occur when the automatic insertion device 451 does not operate properly.

Under that condition, coming close to the wall surface of the body cavity brings forth a light illumination state, and almost the same level of the outputs from the light receiving elements 472a, 472b results in that the difference signal therebetween becomes substantially zero. With this control rule, therefore, the angle control is left as it is because the control direction is unknown, and the alarm lamp 488 is lighted to issue an alarm. Also, in the control of this case, the insertion motors 485, 485 are de-energized to stop operating so that the distal end of the insert section 7 will not strike against the wall surface of the body cavity.

Other control rules III through VI are further used to produce output signals with fuzzy inference.

Accordingly, assuming that the total signal (a+b+c+d) has a value x1 and the difference signal a-b has a value x2 as shown in FIG. 37(A) and 38(B), respectively, the degree of the angle control is given by hatched areas shown in FIG. 37(C) and the degree of the alarm light control is given by hatched areas shown in FIG. 37(D). Superposition of the three hatched areas in FIG. 37(C) results in a pattern of three figures as shown in FIG. 37(E), which are subjected to a MAX operation. The centroid x3 of the resulting membership function is obtained as the angle control quantity in the up/down direction. The fuzzy inference section 483 outputs a signal depending on the angle control quantity to the up/down angle control circuit 579A. As a result, the angle control in the slightly downward direction is performed in this case.

Further, in this case, an output value for the alarm lamp 38 is near an off state and the alarm lamp 38 is thus not lighted.

With this seventh embodiment, the endoscope can be automatically inserted toward the deepest portion of the insertion route with a simple construction.

Moreover, since the insert section and the blinking of the alarm lamp 488 are controlled using the fuzzy inference means, the seventh embodiment makes it possible to execute more appropriate decision at a high speed than an ordinary digital computer. More specifically, with a control process executed by the ordinary computer, if there are a plurality of conditions in the antecedent portion each corresponding to an "if . . . then" sentence, those conditions independently affect the consequent portion as the conclusive portion. It is thus a general proposition that in any cases where the data perfectly satisfy the conditions of the antecedent portion and where the data are fairly deviated from the perfect conditions, the control result becomes the same if the data fall within a preset range.

In contrast, the fuzzy inference means functions such that, as will be also seen from FIG. 37, when the data better satisfy the conditions of the antecedent portion, the consequent portion contributes to the control result at a larger degree or proportion, and when the data less satisfy the conditions of the antecedent portion, the consequent portion contributes to the control result at a smaller proportion. Thus, there can be derived the control result as provided by weighting a basic control rule.

Therefore, the obtained control result approaches an optimum value.

Although the control result depending on the proportion meeting the conditions of the antecedent portion can be also obtained by usual computer control, implementation of this requires a so large amount of computations as to necessitate scale-up of the device itself or use of a very high-speed computer. On the contrary, the fuzzy inference means makes it possible to obtain the control result with a smaller scale and a shorter period of time, leading to an advantage that the device is simplified in construction and reduced in size.

Figure 39:
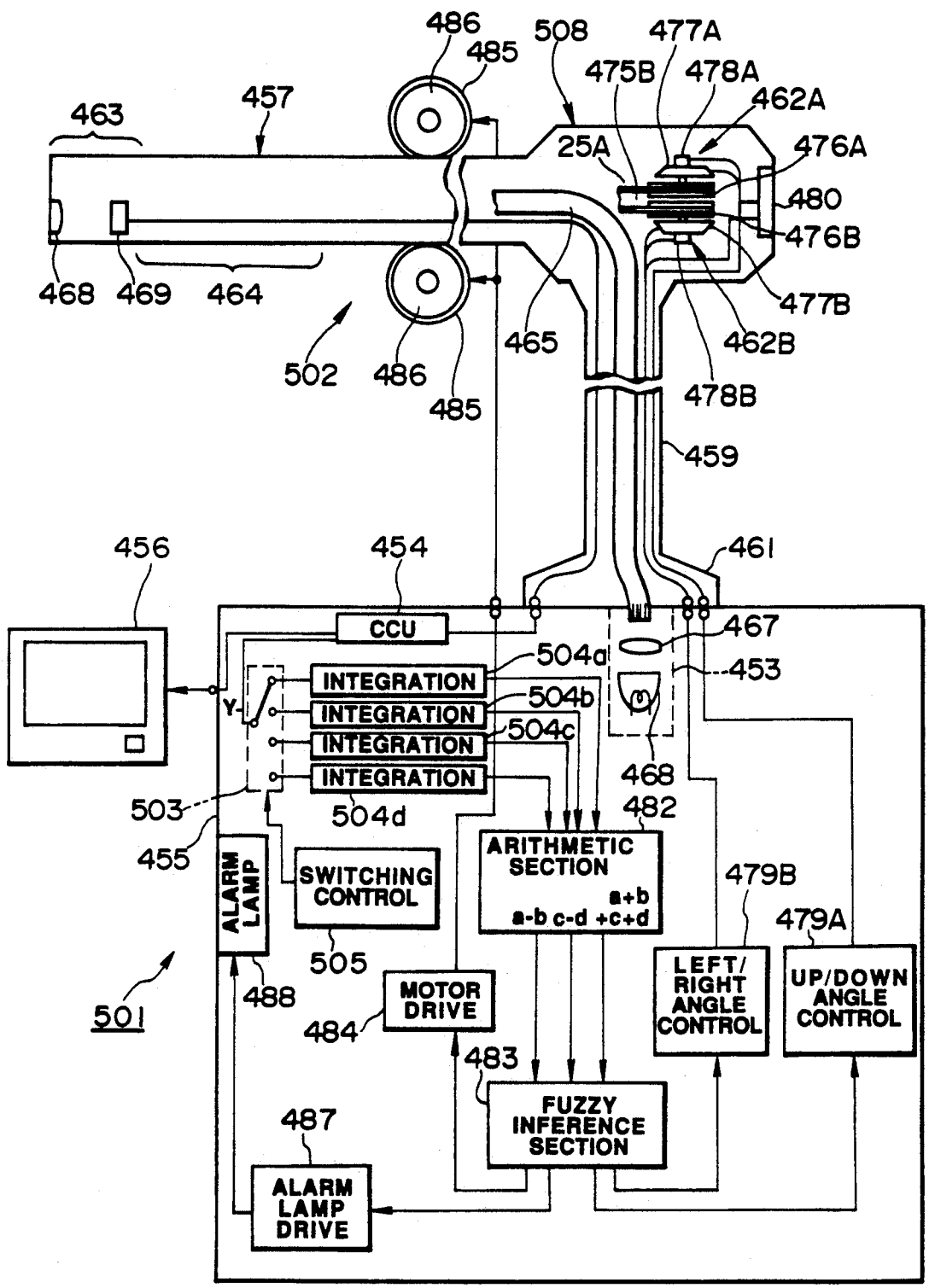

FIG. 39 shows an entire arrangement of an automatic insertion device 501 according to an eighth embodiment of the present invention. In this embodiment, an electronic endoscope 502 is formed by omitting the half prism 471 and the light receiving section 472 in the endoscope of FIG. 35. The control unit 454 is arranged such that a luminance signal Y applied to an NTS encoder (not shown) in the CCU 454 is selectively introduced to integrating circuits 504a, 504b, 504c, 504d via a select switch 503, and integrated signals of the integrating circuits 504a, 504b, 504c, 504d are inputted to the arithmetic section 482.

The select switch 503 has contacts Sa, Sb, Sc, Sd which are changed over by a switching control circuit 505 as shown in FIG. 39.

For an image of one field/frame on the monitor screen shown in FIG. 40a, the select switch 503 is changed over such that luminance signal of four regions Ra, Rb, Rc, Rd divided by two diagonals, by way of example, are inputted to the integrating circuits 504a, 504b, 504c, 504d, respectively.

During a video signal period of the scan line shown in FIG. 40a, for instance, the contacts Sc, Sa and Sb are turned on as depicted in FIGS. 40b, 40c and 40d, respectively.

Therefore, the integrating circuits 504a, 504b, 504c, 504d jointly serve as the light receiving section 472 in the seventh embodiment.

The remaining arrangement is almost the same as the seventh embodiment. In addition to operation similar to that in the seventh embodiment, this eighth embodiment also has an advantage that an electronic endoscope of a type not including the light receiving section 472 can be used as the electronic endoscope 502.

Note that instead of blinking the alarm lamp 488, an alarm mark may be displayed on the monitor screen. Further, the seventh and eighth embodiments are also applicable to a TV camera attachment type endoscope in which a TV camera is fitted to an eyepiece of a fiber scope.

In addition, the monitor screen may be divided into more than four regions for the purpose of finer control.

According to the seventh and eighth embodiments, as described above, since an endoscope image is divided into plural regions, output levels of the respective regions are compared with each other, and output signals resulting from the comparison are applied to the fuzzy inference means to control the insert direction of an endoscope, it is possible to insert the endoscope properly and automatically with the simple construction.

Figure 41:
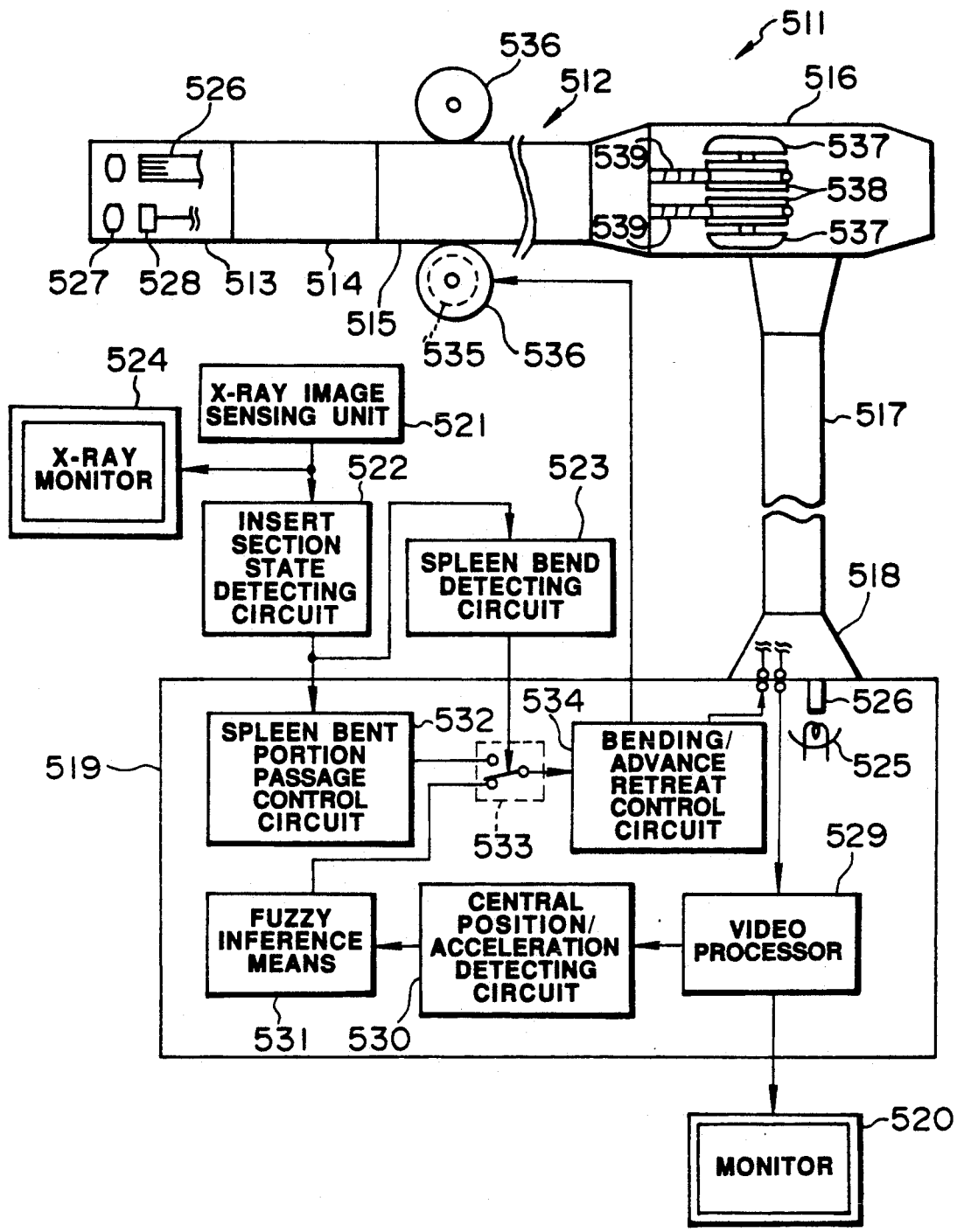
FIG. 41 is an arrangement view of an endoscope device of the ninth embodiment.

An endoscope device of a ninth embodiment of the present invention comprises, as shown in FIG. 41, an endoscope 511 formed to be so slender or thin as to enable its insertion into a body cavity, for example, a control unit 519 incorporating a later-described video processor 529 to which a universal cord 517 of the endoscope 511 is connected via a connector 518, a monitor 520 for displaying an image of an object such as some location in body cavities based on an output signal of the video processor 529, an X-ray image sensing unit 521 for picking up an inserted condition by an X-ray, an insert section state detecting circuit 522 for detecting the state of an insert section from an output signal of the X-ray image sensing unit 521, a spleen bend detecting circuit 523 for detecting a bent portion of the spleen from an output signal of the insert section state detecting circuit 522, an X-ray monitor 524 for displaying the output signal of the X-ray image sensing unit 521, and a motor 535 for inserting an insert section 512 of the endoscope 511.

The endoscope 511 comprises the slender insert section 512, a thick operating section 516 provided adjacent to a rear end of the insert section 512, a universal cord 517 extended sidewards from the operating section 516, and the connector 518 provided at an end of the universal cord 517. The insert section 512 comprises a distal end component 513 in which an objective lens 527, a CCD 528 such as a solid image sensing device, etc. are disposed, a bendable section 513 provided adjacent to a rear end of the distal end component 513 in such a manner as able to bend in up/down and left/right directions, and a flexible tube section 515 provided adjacent to a rear end of the bendable section 514. The operating section 516 includes motors 537 for driving the bendable section 514 to bend, and pulleys 538 are associated with the motors 537. Bending wires 539 are anchored to the pulleys 538 so that the bendable section 514 may be bent by letting and pulling the bending wires 539 from and to the pulleys.

The control unit 519 comprises the video processor 529 to which an image pickup signal from the CCD 528 is applied, a central position/acceleration detecting circuit 530 for detecting later-described central position and acceleration from an output signal from the video processor 529, a fuzzy inference means 531 for making inference from an output signal of the central position-/acceleration detecting circuit 530, a spleen bent portion passage control circuit 532 for carrying out spleen bent portion passage control from an output signal of the insert section state detecting circuit 522, a switch 533 for changing over output signals of the fuzzy inference means 531 and the spleen bent portion passage control circuit 532 under control of the spleen bend detecting circuit 523, a bending/advance-retreat control circuit 534 for controlling insertion of the bendable section 514 and the insert section 512, and a lamp 525 for supplying illumination light to a light guide 526 incorporated in the endoscope 511.

The motor 535 is provided with drums 536 disposed in such a manner as to advance and retreat the insert section 512. The motors 535 and 537 are driven by drive signals from the bending/advance-retreat control circuit 534.

Operation of the endoscope device thus arranged will be described below.

Figures 45A, 45B:
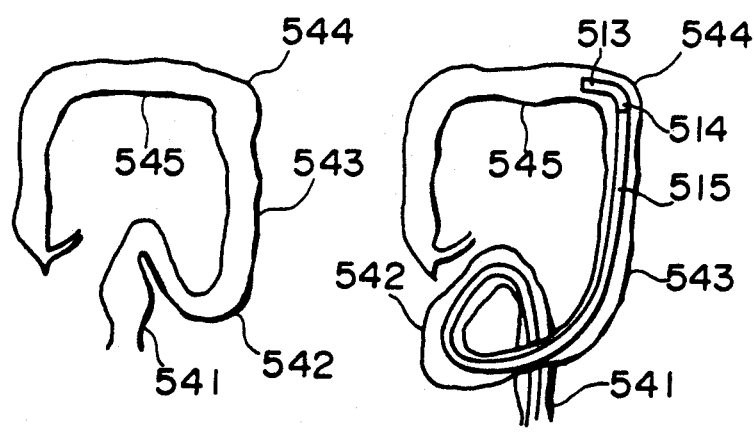

The insert section 512 of the endoscope 511 is inserted by an operator from the anus 541 shown in FIG. 45a, while turning the operating section 516 such that the insert section 512 makes an α-turn in the S-shaped colon as shown in FIG. 45b. The illumination light from the lamp 525 is supplied to the incident end face of the light guide 526, led through the light guide 526, and then irradiated to a body cavity from the emergent end face of the light guide 526 disposed in the distal end component 513. An image of the body cavity irradiated by the illumination light is focused by the objective lens 527 disposed in the distal end component 513 on the photoelectric converting plane of the CCD 528, and a resulting image pickup signal is inputted to the video processor 529. The image pickup signal is subjected to various processing and converted into a video signal by the video processor 529, the video signal being inputted to the monitor 520 so that the monitor 520 displays the image of the body cavity.

The video processor 529 also outputs a processed signal to the central position/acceleration detecting circuit 530. From the processed signal applied, the central position/acceleration detecting circuit 530 detects the coordinate values of a central position of the body cavity tract in front of the distal end component 513, and an acceleration indicating the speed at which the central position moves over the coordinate in front of the distal end component 513 with later-described bending of the bendable section 514 and advance-retreat of the insert section 512, followed by outputting the detected data to the fuzzy inference means 531.

Figures 42A, 42B, 42C, 42D:
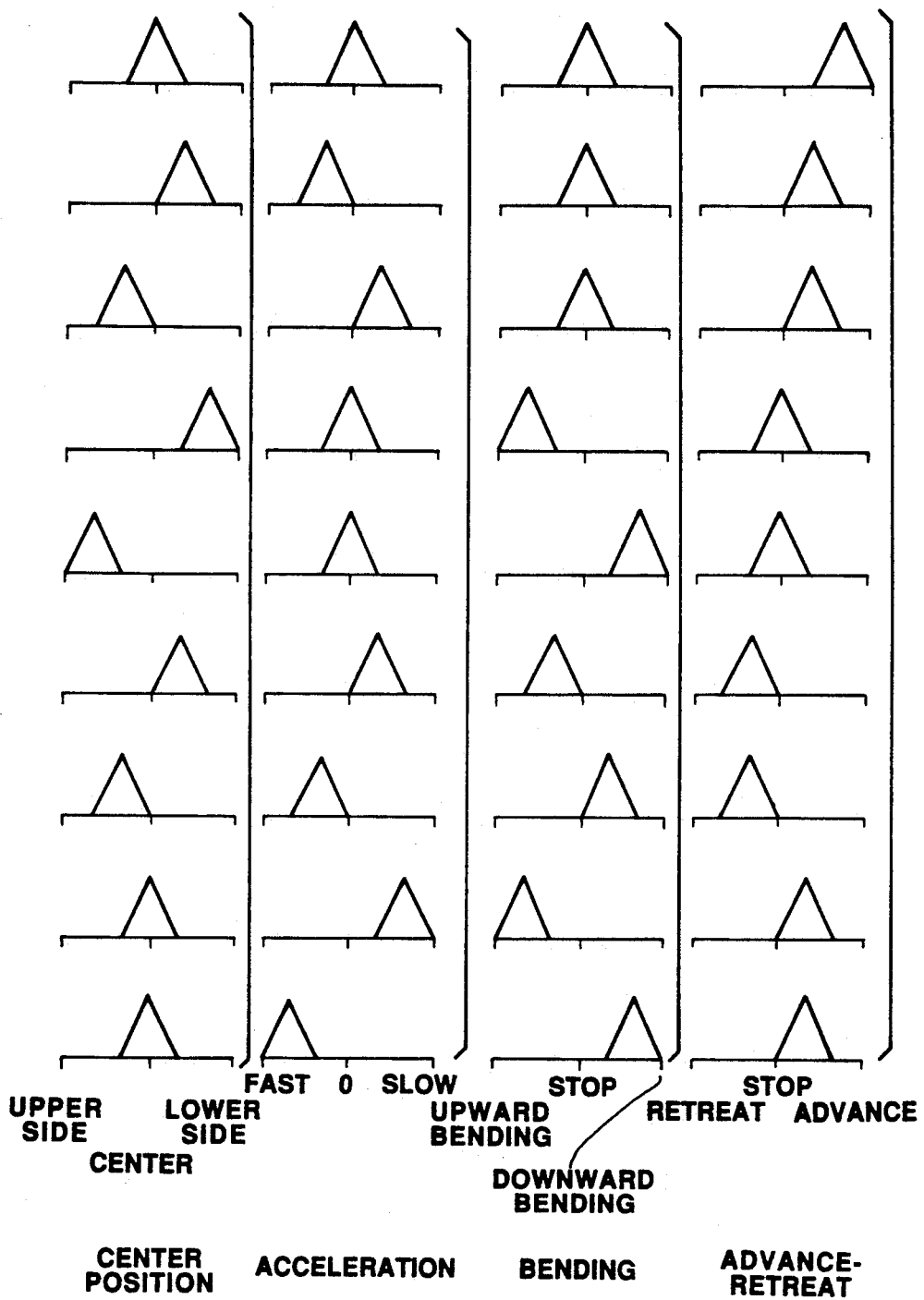
FIGS. 42(a), 42(b), 42(c) and 42(d) are a set of explanatory charts showing membership functions.

The fuzzy inference means 531 puts the coordinate data of the central position in the up/down direction and the acceleration data into the antecedent portion made up by membership functions shown in FIGS. 42a and 42b, and also puts the coordinate data of the central position in the left/right direction into the antecedent portion made up by membership functions (not shown). Then, the fuzzy inference means 531 derives control data consisting of an upward/downward bending direction and a bending angle of the bendable section 514, as well as an advance/retreat movement and an advance/retreat speed of the insert section 2 from the consequent portion made up by membership functions shown in FIGS. 42c and 42d, and a leftward/rightward bending direction and a bending angle of the bendable section 514 from the consequent portion made up by membership functions (not shown), followed by outputting a control signal to the bending/advance-retreat control circuit 534 via a break contact and a transfer terminal of the switch 533. The above control data may be obtained by using the fuzzy inference rules explained above or any other suitable ones.

In response to the control signal based on the above control data, the bending/advance-retreat control circuit 534 drives or brakes the motor 537 in such a manner as to make the bendable section 514 bend up, down, left or right or stop the bending, and also the motor 535 in such a manner as to make the insert section 512 advance, retreat or stop the movement. An image of such an inserted condition is sensed by the X-ray image sensing unit 521 to be displayed on the X-ray monitor 524 and also outputted to the insert section state detecting circuit 522. The insert section state detecting circuit 522 outputs the inserted state of the insert section 512 thus detected to both the spleen bend detecting circuit 523 and the spleen bent portion passage control circuit 532.

When the insert section 512 is inserted into the body cavity to such an extent that it passes through the descending colon 543 and reaches a spleen bent portion 544, its further advance is prevented by the spleen bent portion 544 and the α-turn in the S-shaped colon 542 is slacked. Thus, even if the advance of the insert section 512 is continued, the insert section 512 only increases the slack of the α-turn and cannot reach the transverse colon 545. An image of this condition is sensed by the X-ray image sensing unit 521 to be displayed on the X-ray monitor 524 and also detected by the spleen bend detecting circuit 523 via the insert section state detecting circuit 522.

The spleen bend detecting circuit 523 detects the above condition and outputs a control signal to the switch 533. In response to the control signal, the switch 533 changes over the input terminal of the bending/advance-retreat control circuit 534 to the spleen bent portion passage control circuit 532.

Figure 43:
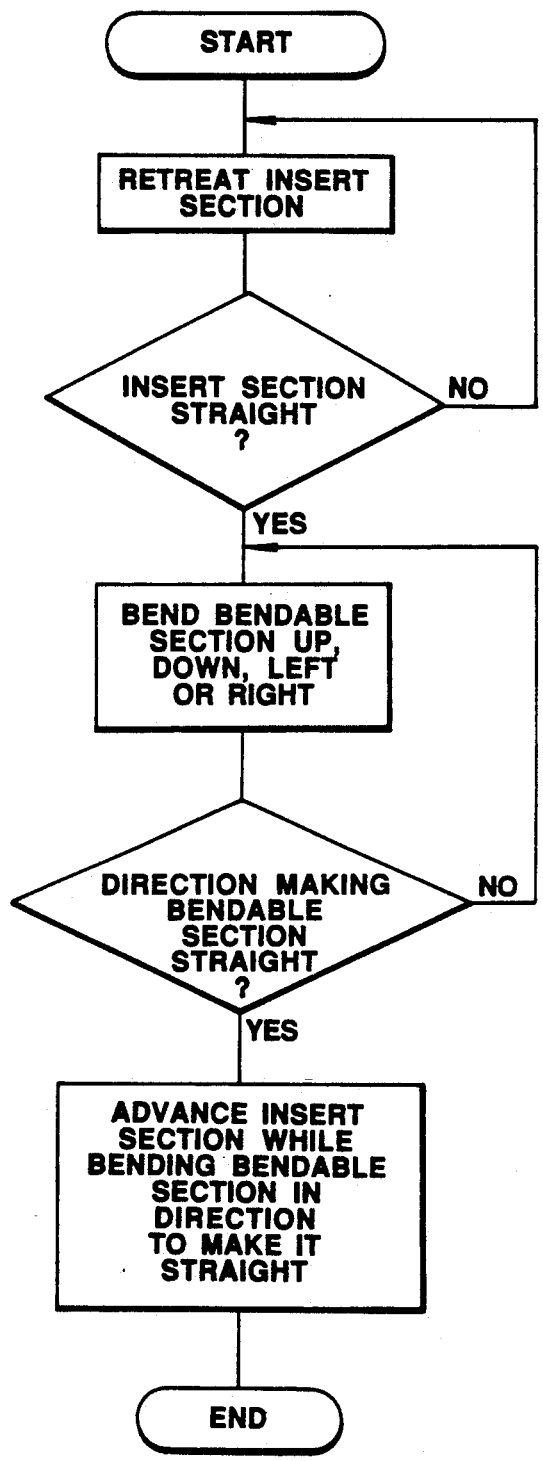
FIGS. 43, 44(a), 44(b), 44(c), 44(d), 45(a) and 45(b) are representations for explaining an insertion manner.
Figure 44A:
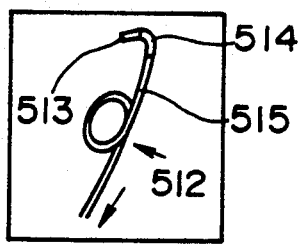
Figure 44B:
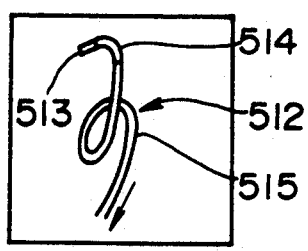
Figure 44C:
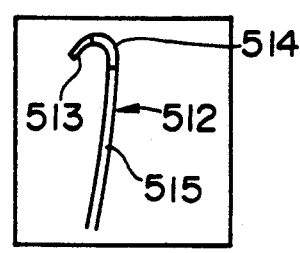
Figure 44D:
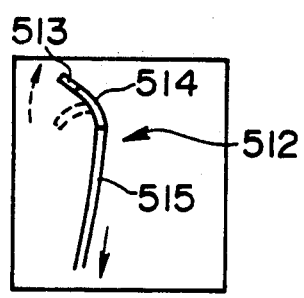

The spleen bent portion passage control circuit 532 controls the bending/advance-retreat control circuit 534 in response to the output signal of the insert section state detecting circuit 522 as shown in FIG. 43. First, as shown in FIGS. 44a, 44b and 45b, under a condition that the bendable section 514 is bent to hold the distal end component 513 of the insert section 512 latched by a joint area between the transverse colon 545 and the spleen bent portion 544, the insert section 512 is controlled to retreat. At this time, the operator turns the operating section 516 in a direction opposite to that in the above insertion of the insert section 512, whereby the α-turn in the S-shaped colon 542 disappears to make the insert section 512 extend straight. Then, in order to detect the direction in which the bendable section 514 extends straight, the bendable section 514 is controlled to bend up, down, left and right as shown in FIG. 44d. Upon detecting the direction in which the bendable section 514 extends straight, the bendable section 514 is bent in the same direction, while controlling the insert section 512 to advance.

Note that the switch 533 may be changed over not by the control signal from the spleen bend detecting circuit 523, but manually at the discretion of the operator.

In short, this embodiment has an advantage that using the control signals from the fuzzy inference means 531 and the spleen bent portion passage control circuit 532, the insert section 512 can be inserted into the transverse colon 545 by the mechanical means, allowing the operator to easily operate the endoscope 511.

Next, a tenth embodiment of the present invention will be described. The components which are arranged and operate similarly to those in the ninth embodiment are designated by the same reference numerals and will not be explained here.

Figure 46:
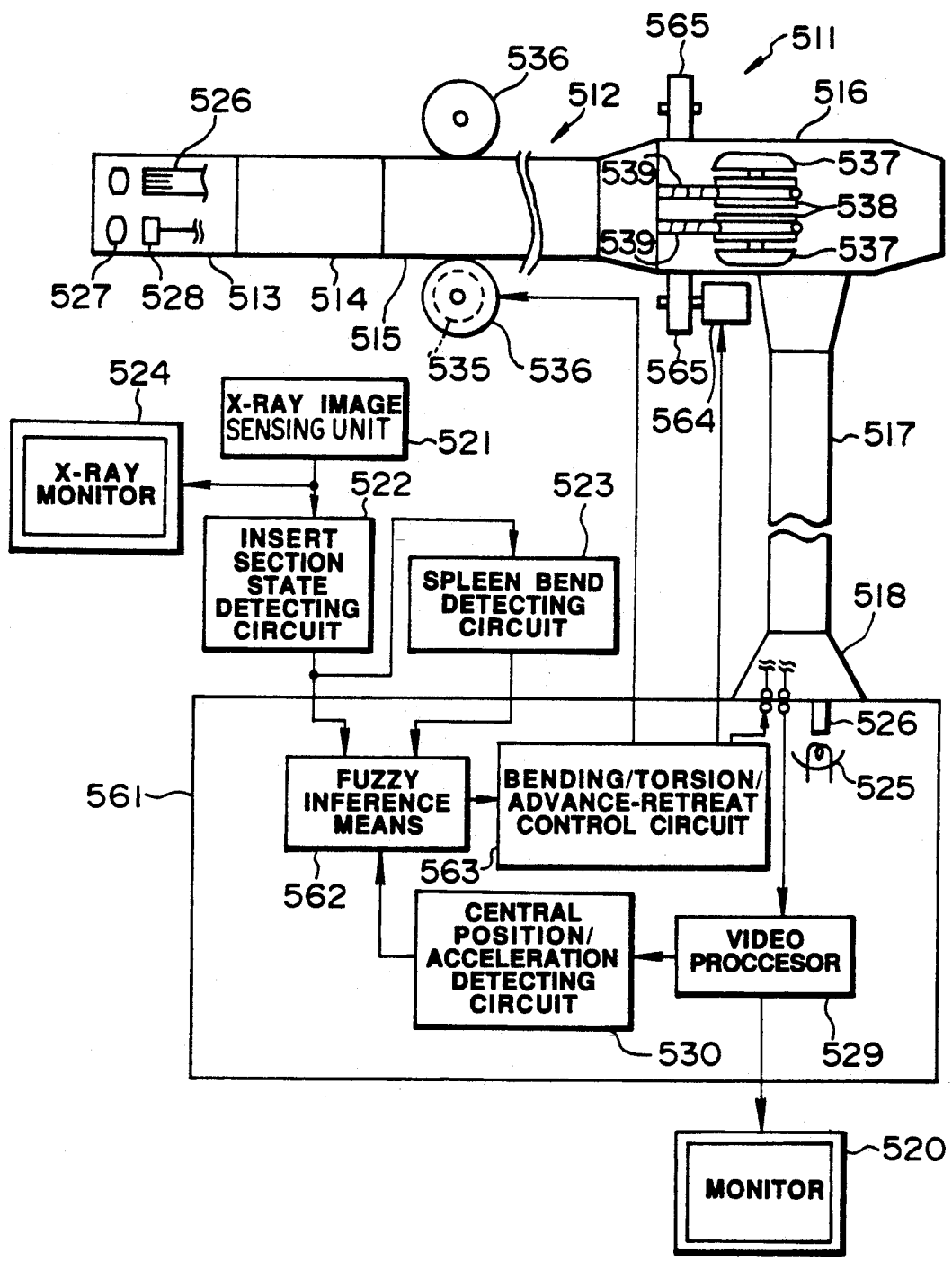

An endoscope device comprises, as shown in FIG. 46, the endoscope 511, a control unit 561 incorporating the later-described video processor 529 to which the universal cord 517 of the endoscope 511 is connected via the connector 518, the monitor 520, the X-ray image sensing unit 521, the insert section state detecting circuit 522, the spleen bend detecting circuit 523, the X-ray monitor 524, the motor 535, and a motor 564 for torsionally rotating the insert section of the endoscope 511.

The control unit 561 comprises the video processor 529, the central position/acceleration detecting circuit 530, a fuzzy inference means 562 for making inference from one of output signals of the central position/acceleration detecting circuit 530 and the insert section state detecting circuit 522 which are changed over in response to an output signal of the spleen bend detecting circuit 523, a bending/torsion/advance-retreat control circuit 563 for controlling torsion and insertion of the bendable section 514 and the insert section 512 based on the output signal of the fuzzy inference means 562, and the lamp 525.

The motor 564 is provided with drums 565 disposed in such a manner as to turn the operating section 516.

The motors 535, 537 and 564 are driven by drive signals from the bending/torsion/advance-retreat control circuit 563.

Operation of the endoscope device thus arranged will be described below.

The endoscope device operates in a like manner to the ninth embodiment until reaching the spleen bent portion, and thus the description thereof is omitted here.

As with the ninth embodiment, when the spleen bend detecting circuit 523 detects the insert section reaching the spleen bent section, the spleen bend detecting circuit 523 outputs a detection signal to the fuzzy inference means 562.

Figure 47:
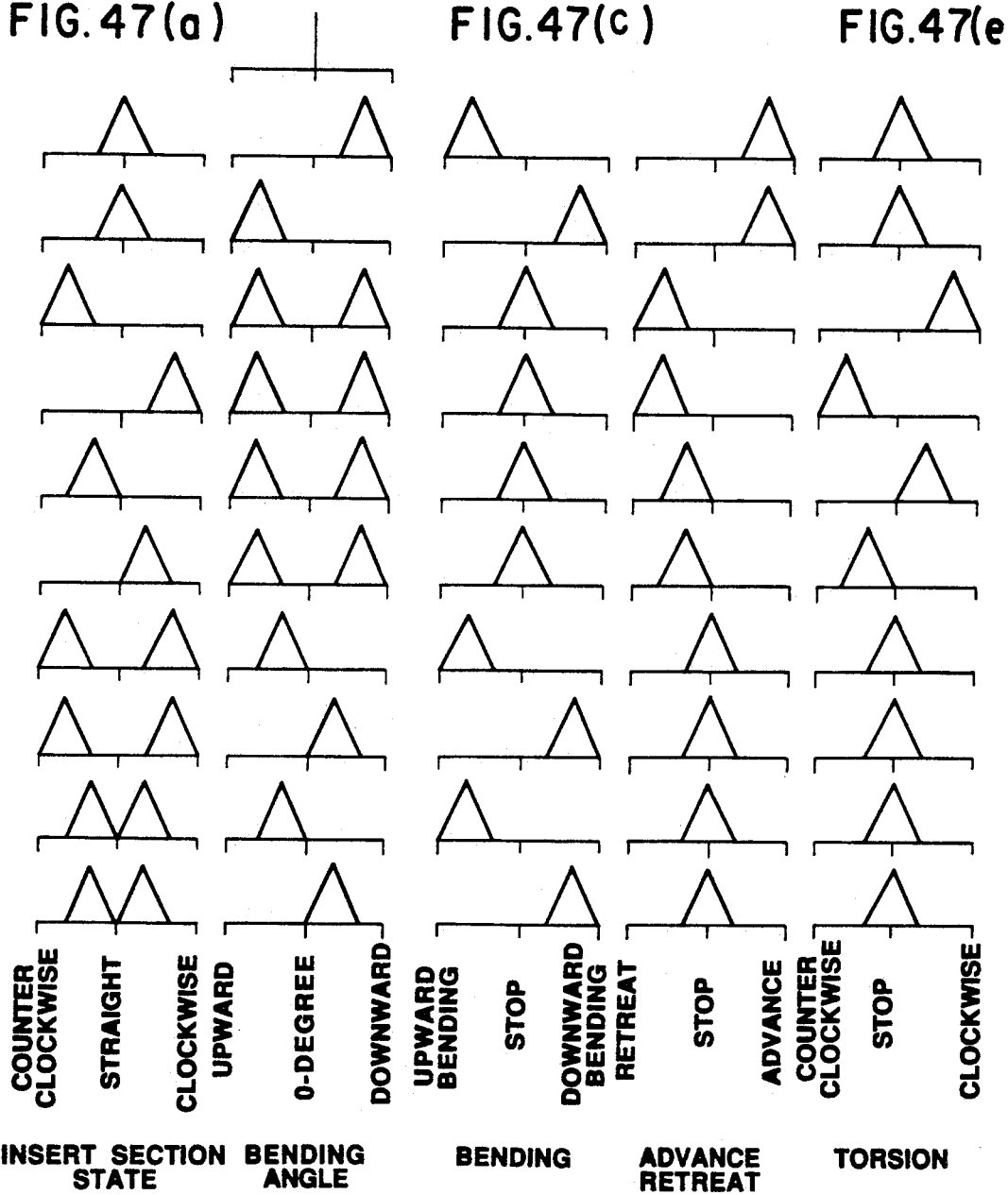

In response to the detection signal, the fuzzy inference means 562 changes over membership functions from the first group shown in FIG. 42 to the second group shown in FIG. 47. More specifically, the state of the insert section 3 and the bending angle of the bendable section 513 in the up/down direction are put into the antecedent portion made up by the second group of membership functions shown in FIGS. 47a and 47b, and the bending angle of the bendable section 513 in the left/right direction is put into the antecedent portion made up by the second group of membership functions (not shown). Then, the fuzzy inference means 562 derives control data consisting of an upward/downward bending direction and a bending angle of the bendable section 514, an advance/retreat movement and an advance/retreat speed of the insert section 2, as well as a torsion direction and a torsion angle of the insert section 512 from the consequent portion made up by the second group of membership functions shown in FIG. 47e, and a leftward/rightward bending direction and a bending angle of the bendable section 514 from the consequent portion made up by the second group of membership functions (not shown), followed by outputting a control signal to the bending/torsion/advance-retreat control circuit 563.

In response to the above control data, the bendable section 514 is first bent to hold the distal end component 513 of the insert section 512 latched by a joint area between the transverse colon and the spleen bent portion. Then, the insert section 512 is controlled to retreat and, at this time, the operating section 516 is operated to turn in a direction to eliminate the aforementioned α-turn of the insert section 512 so that the α-turn disappears to make the insert section 512 extend straight. Afterward, in order to detect the direction in which the bendable section 514 extends straight, the bendable section 514 is controlled to bend up, down, left and right as shown in FIG. 44d. Upon detecting the direction in which the bendable section 514 extends straight, the bendable section 514 is bent in the same direction, while controlling the insert section 512 to advance. Note that the above control data may be obtained by using the fuzzy inference rules explained above or any other suitable ones.

In the antecedent portion made up by the second group of membership functions shown in FIG. 47 for the fuzzy inference means 562, zero values of the bending angle in the up/down and left/right directions represent a privilege mode in which the membership functions are returned to the first group of memberships shown in FIG. 42 in preference to all other conditions of the antecedent portion.

In response to the control signal based on the above control data, the bending/torsion/advance-retreat control circuit 563 drives or brakes the motor 537 in such a manner as making the bendable section 514 bend up, down, left or right or stop the bending, the motor 535 in such a manner as making the insert section 512 advance, retreat or stop the movement, and further the motor 564 in such a manner as to cause the operating section 516 to turn left or right or stop the torsion.

In short, this embodiment has an advantage that using the control signal from the fuzzy inference means 562, the insert section 512 can be inserted into the transverse colon by a mechanical means, allowing the operator to easily operate the endoscope 511.

Next, an eleventh embodiment of the present invention will be described. This embodiment is concerned with an active endoscope in which the insert section comprises a plurality of bendable segments (articulations) and, as the insert section advances, a motion of the segment on the front or tip side is in turn transmitted to the segment on the rear or root side.

Japanese Patent Laid-Open No. 63-136014 discloses an active endoscope in which the insert section comprises a plurality of bendable segments (articulations) each made of a shape memory array, and a bending quantity of the segment at the tip end is successively transmitted to the subsequent segment so that the insert section may be smoothly inserted into a complicated canal path. However, the segment on the top side and the segment on the root side undergo different loads due to not only weight of the insert section of the endoscope, but also undulations of the canal path or the like. Therefore, the conventional active endoscope has suffered from a problem that the segment on the top side and the segment on the root side cannot always exhibit the same motion, whereby the insert section may not be inserted smoothly. Furthermore, since the canal path may change with progress of insertion in the great intestine, for example, it is not always optimum that a motion of the segment at the tip end is directly shifted to the subsequent segments. In contrast, this embodiment is designed so as to make all the segments operate substantially in the same manner, thereby enabling smooth insertion of the insert section irrespective of different loads exerted on the segments.

Figure 48:
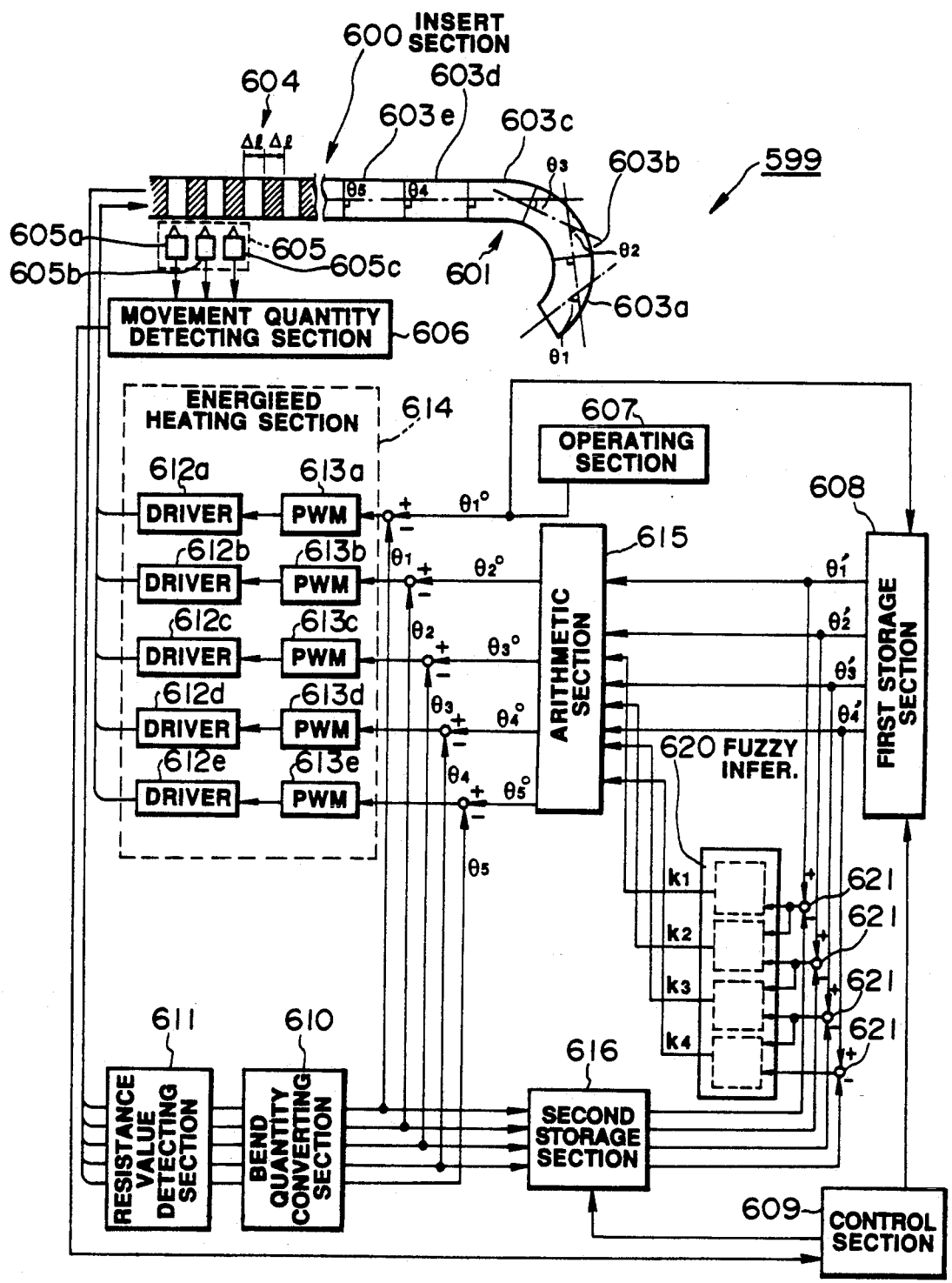

As shown in FIG. 48, an active endoscope constituting an active endoscope device 599 has a slender insert section 600 which is provided with an actuator 601 at the distal end side. The actuator 601 comprises a plurality, e.g., five, of segments 603a, 603b, 603c, 603d, 603e jointed in the axial direction. In each segment, a pair of spiral shape memory alloys (hereinafter referred to as SMA's) are disposed to axially extend at respective positions symmetrical about the central axis. Both ends of the SMA's are respectively fixed to a pair of flanges. A bias spring is also disposed on the central axis of each segment and has its both ends similarly fixed to a pair of flanges.

Further, at the rear end side of the insert section 601, there is provided a marking section 604 in a stripe pattern with spacing of $\Delta l$ for purpose of detecting a movement distance of the insert section 601. A sensor section 605 is provided opposite the marking section 604. The sensor section 605 has, for example, three photosensors 605a, 605b, 605c, each comprising a pair of light emitting and receiving elements, with a spacing of 1.5$\Delta l$. Outputs of the photosensors 605a, 605b, 605c are inputted to a movement quantity detecting section 606. The movement quantity detecting section 606 determines a direction of movement of the making section 604, that is, a direction of movement of the insert section 601, from the delay or advance in phase of the outputs from the photosensors 605a, 605b, 605c, and also measures a movement quantity of the insert section 601 by counting the number of output pulses of any one photosensor, that is, the number of pattern stripes going past the photosensor. A detection output of the movement quantity detecting section 606 is applied to a control section 609.

On the other hand, the segments 603a through 603e are each controlled in its bending by an energizing and heating section 614. The energizing and heating section 614 comprises drivers 612a through 612e connected to respective SMA's of the segments 603a through 603e, and pulse width modulation (PWM) circuits 613a through 613e respectively connected to the drivers 612a through 612e.

Also connected to the SMA's of the segments 603a through 603e is a resistance value detecting section 611. The resistance value detecting section 611 is connected to the SMA's via wires dedicated for resistance value detection and separate from energizing wires connecting between the energizing and heating section 614 and the SMA's. This enables it to precisely detect resistance values of the SMA's without being affected by changes in resistance values of the energizing wires due to heating under the energization. Outputs of the resistance value detecting section 611 are converted by a bend quantity converting section 610 into actual bend quantities (angles) $\theta 1$ through $\theta 4$ of the segments 603a through 603e. The bend quantities $\theta 1$ through $\theta 4$ outputted from the converting section 610 are stored in a second storage section 616. The second storage section 616 is controlled by the control section 609 to output the bend quantities $\theta 1$ through $\theta 4$, as required.

A target value $\theta 1°$ of the bend quantity of the first segment 603a at the distal end is manually inputted from an operating section 607. Then, a difference between the target value $\theta 1°$ from the operating section 607 and the actual bend quantity $\theta 1$ of the first segment 603a outputted from the bend quantity converting section 610 is supplied to the PWM circuit 613a of the energizing and heating section 614.

The target value $\theta 1°$ of the bend quantity of the first segment 603a is stored in a first storage section 608. The first storage section 608 is controlled by the control section 609 such that it is shifted in the order of $\theta 1° \rightarrow \theta 1' \rightarrow \theta 2' \rightarrow \theta 3' \rightarrow \theta 4'$ and outputted to an arithmetic section 615 to become a target value of the subsequent segment before correction, each time the insert section 601 is moved by a distance corresponding to the length of one segment.

Further, subtractors 621, 621, 621, 621 respectively calculate difference between the target values $\theta 1'$, $\theta 2'$, $\theta 3'$, $\theta 4'$ outputted from the first storage section 608 and the actual bend quantities $\theta 1$, $\theta 2$, $\theta 3$, $\theta 4$ outputted from the second storage section 616, the calculated differences being applied to a fuzzy inference section 620. The fuzzy inference section 620 serves to derive coefficients k1, k2, k3, k4 for correcting the target values of bend quantities of the segments 603b, 603c, 603d, 603e with fuzzy inference.

Using $\theta 1'$, $\theta 2'$, $\theta 3'$, $\theta 4'$ from the first storage section 608 and k1, k2, k3, k4 from the fuzzy inference section 620, the arithmetic section calculates a target value $\theta n°$ for the n-th segment following an arithmetic equation below;

$$\theta n° = an + kn\theta n-1'$$

where an is a correction coefficient depending on the segment number (n), $\theta n-1'$ is a target value for the (n−1)-th segment before correction, i.e., a value of shifted $\theta 1°$ depending on the movement quantity of the insert section 601, and kn is a correction coefficient with the fuzzy inference. Because the insert section 601 undergoes a larger load in area nearer to its rear end, the coefficient to correct such a variation in the load is the above an which is expressed by, for example:

$$an = 1 + 0.05n$$

The above kn gives the coefficient to correct the target value for the n-th segment derived with the fuzzy inference based on both a difference $\theta n-1'-\theta n-1$ between the target value of bend quantity and the actual bend quantity for the one-articulation earlier ((n−1)-th) segment, and a difference $\theta n-2'-\theta n-2$ between the target value of bend quantity and the actual bend quantity for the two-articulation earlier ((n−2)-th) segment. Note that there is no two-articulation earlier segment for the second segment 603b, so the k2 is derived based on only the difference between the target value of bend quantity and the actual bend quantity for the one-articulation earlier segment.

The target values $\theta 2°$ through $\theta 5°$ of bend quantities for the second through fifth segments 603b–603e obtained by the arithmetic section 615 are respectively subtracted by the actual bend quantities $\theta 2$ through $\theta 5$ outputted from the bend quantity converting section 610, the resulting differences being supplied to the PWM circuits 613b–613e of the energizing and hearing section 614. The PWM circuits 613b–613e respectively supply energization pulses with duty ratios depending on the differences between the target values $\theta 1°$ through $\theta 5°$ and the actual bend quantities $\theta 1$ through $\theta 5$, to the SMA's of the segments via drivers 612a–612e. The supply of the energization pulses is continued until the above differences each become zero.

When the insert section 601 is inserted by a distance corresponding to one segment in this way, the target value $\theta 2°$ after correction is determined based on the target value $\theta 1'$ ($=\theta 1°$) for the first segment 603a, the correction coefficient a2 depending on the segment number, and the correction coefficient k2 with the fuzzy inference, following which the second segment 603b is driven to bend in accordance with the target value $\theta 2°$. At this time, if a new target value $\theta 1°$ for the first segment 603a is inputted, the first segment 603a is driven to bend in accordance with this new target value $\theta 1°$. When the insert section 601 is further inserted by a distance corresponding to one segment, the target value $\theta 3°$ after correction is determined based on the target value $\theta 2'$ (equal to the shifted $\theta 1'$) for the second segment 603b, the correction coefficient a3 depending on the segment number, and the correction coefficient k3 with the fuzzy inference, following which the third segment 603c is driven to bend in accordance with the target value $\theta 3°$. At this time, the second segment 603b is driven to bend in accordance with a new target value $\theta 2°$ determined based on $\theta 1'$ equal to the shifted new target value $\theta 1°$ and the correction coefficients a2, k2. The fourth and subsequent segments 603d, etc. are also operated in a like manner.

The fuzzy inference carried out by the fuzzy inference section 620 of this embodiment will now be described.

Assuming that;

$$\theta n-1'-\theta n-1=A, \theta n-2'-\theta n-2=B$$

the following seven rules are adopted as fuzzy rules in this embodiment.

1. If A is nearly 0, then kn is set to be medium.
2. If A is negative and B is nearly 0, then kn is set to be very large.
3. If A is positive and B is nearly 0, then kn is set to be very small.
4. If A is negative and B is negative, then kn is set to be medially large.
5. If A is positive and B is positive, then kn is set to be medially small.
6. If A is negative and B is positive, then kn is set to be slightly large.
7. If A is positive and B is negative, then kn is set to be slightly small.

Note that kn is in a range of $0 \geqq kn \geqq 2$ with the term "medium" indicating 1 or thereabout.

Figure 49:
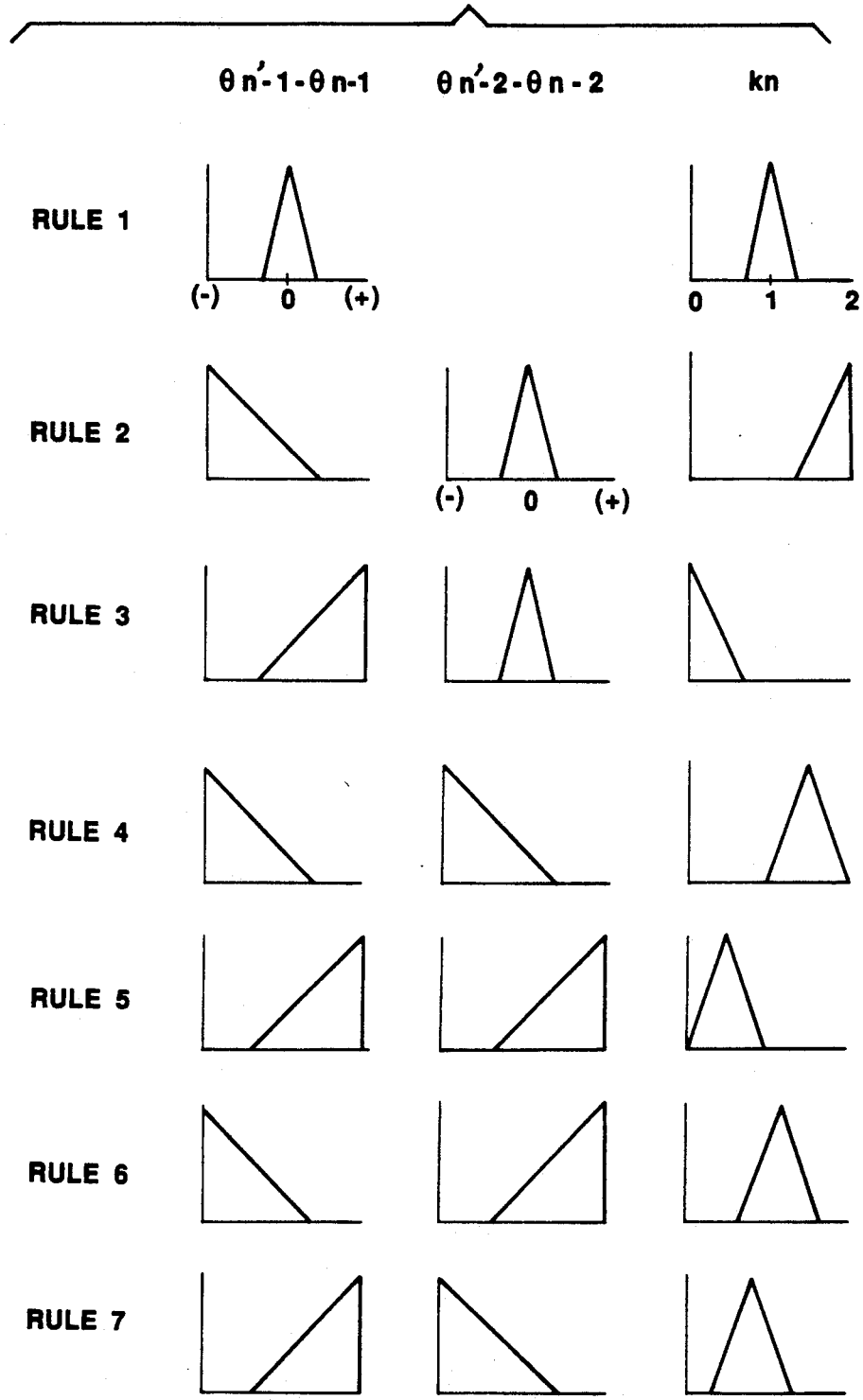

The above rules can be expressed in the form of membership functions, as shown in FIG. 49.

In the fuzzy inference section 620, the above seven rules are applied simultaneously to MIN operations to determine a degree of coincidence in the precedent portion of each rule for respective inputs, and the resulting degree is used as a weight for the consequent portion of that rule. Then, a MAX operation is executed to synthesize the consequent portions of all the rules and a centroid value of the resulting membership function, for example, is derived as an output value. This output value is given as the correction coefficient kn. The above execution of the fuzzy rules and arithmetic operation of the inference result can be implemented at a high speed by using a fuzzy chip. Notice that, as mentioned before, there is no two-articulation earlier segment for the second segment 603b, so the k2 is derived based on only $\theta n-1'-\theta n-1$ in the antecedent portion.

Figure 50:
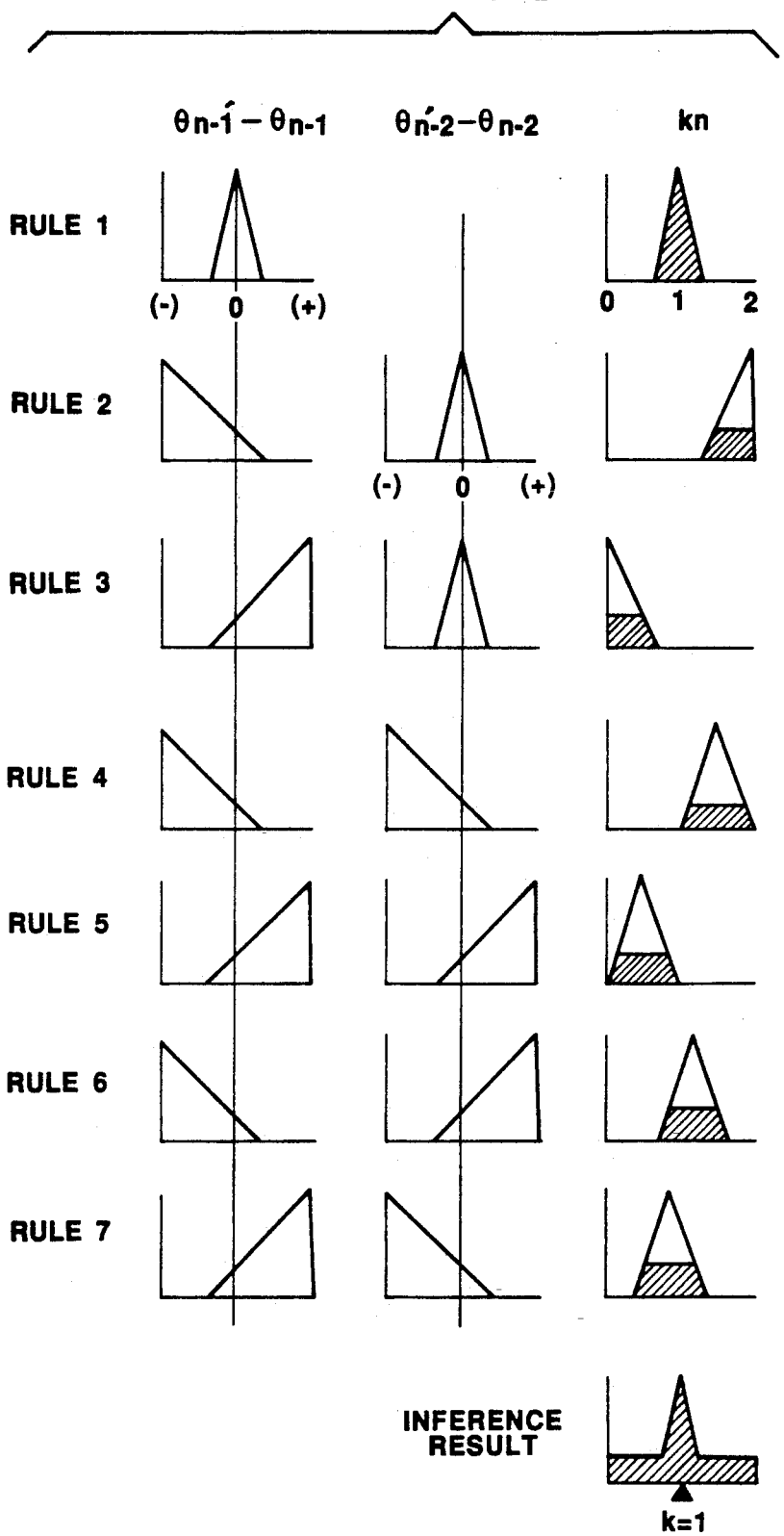
Figure 51:
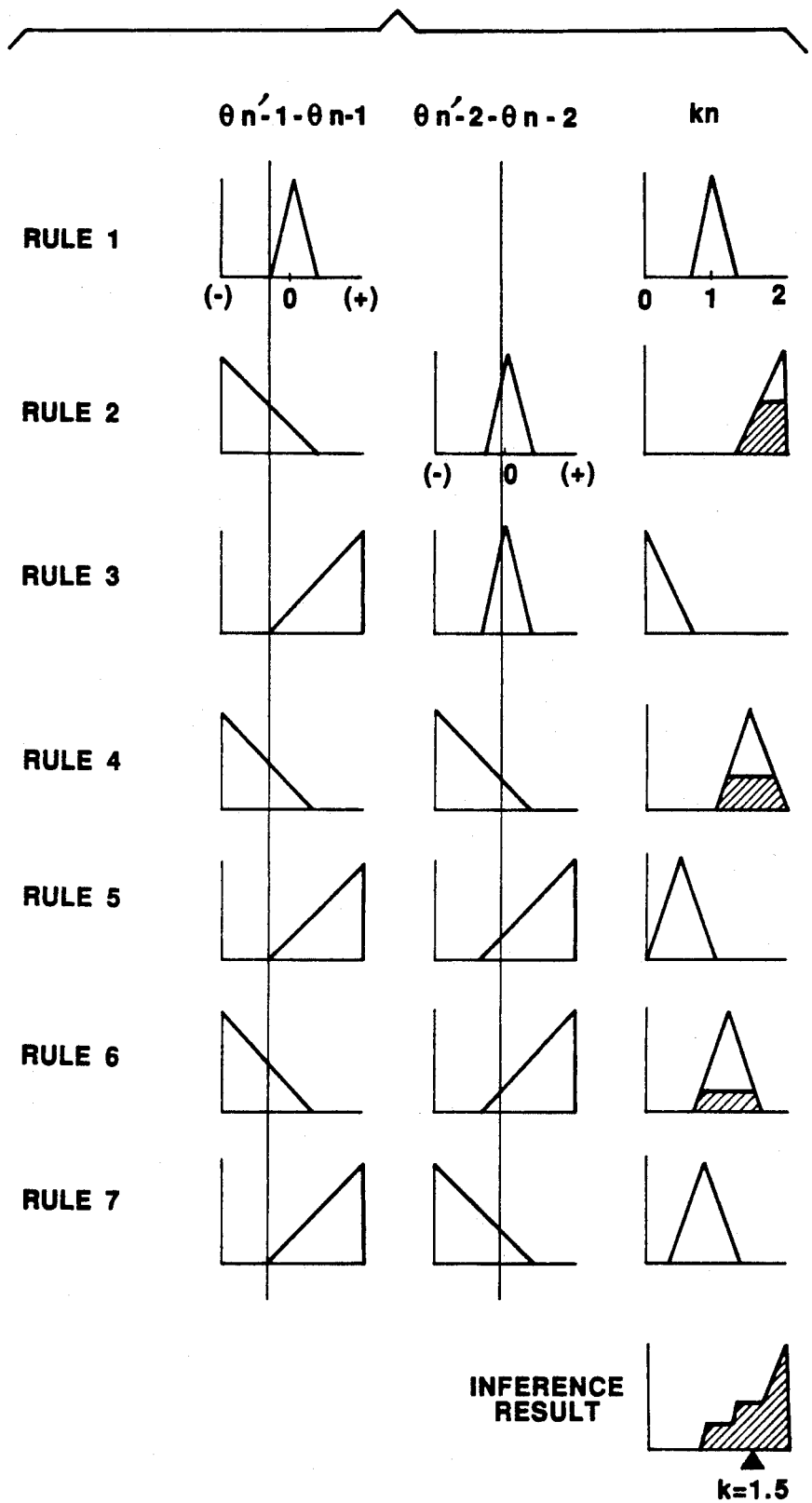

FIGS. 50 and 51 show examples of inputs to and an inference result from the fuzzy inference section 620.

The example of FIG. 50 represents the case in which $\theta n-1'-\theta n-1$ and $\theta n-2'-\theta n-2$ are each 0. In this case, all the seven rules are applied with respective weights indicated by hatched areas, thereby providing an illustrated membership function as the inference result. Then, the value 1 corresponding to the centroid position of the resulting membership function is given as kn.

The example of FIG. 51 represents the case in which $\theta n-1'-\theta n-1$ and $\theta n-2'-\theta n-2$ are each a negative value indicated by a vertical line intersecting the membership functions of the antecedent portions for all the rules. In this case, the rules 2, 4, 6 are applied with respective weights indicated by hatched areas, thereby providing an illustrated membership function as the inference result. Then, the value 1.5 corresponding to the centroid position of the resulting membership function is given as kn.

With this embodiment, as described above, even if the segments undergo different loads due to weight of the insert section of the endoscope, undulations of the canal path and other factors, all the segments can operate substantially in the same manner, thereby enabling smooth insertion of the insert section. Also, because of using information about the up to two-articulation earlier segments, it is possible to operate the segments in expected motion or predicted fashion.

Figure 52:
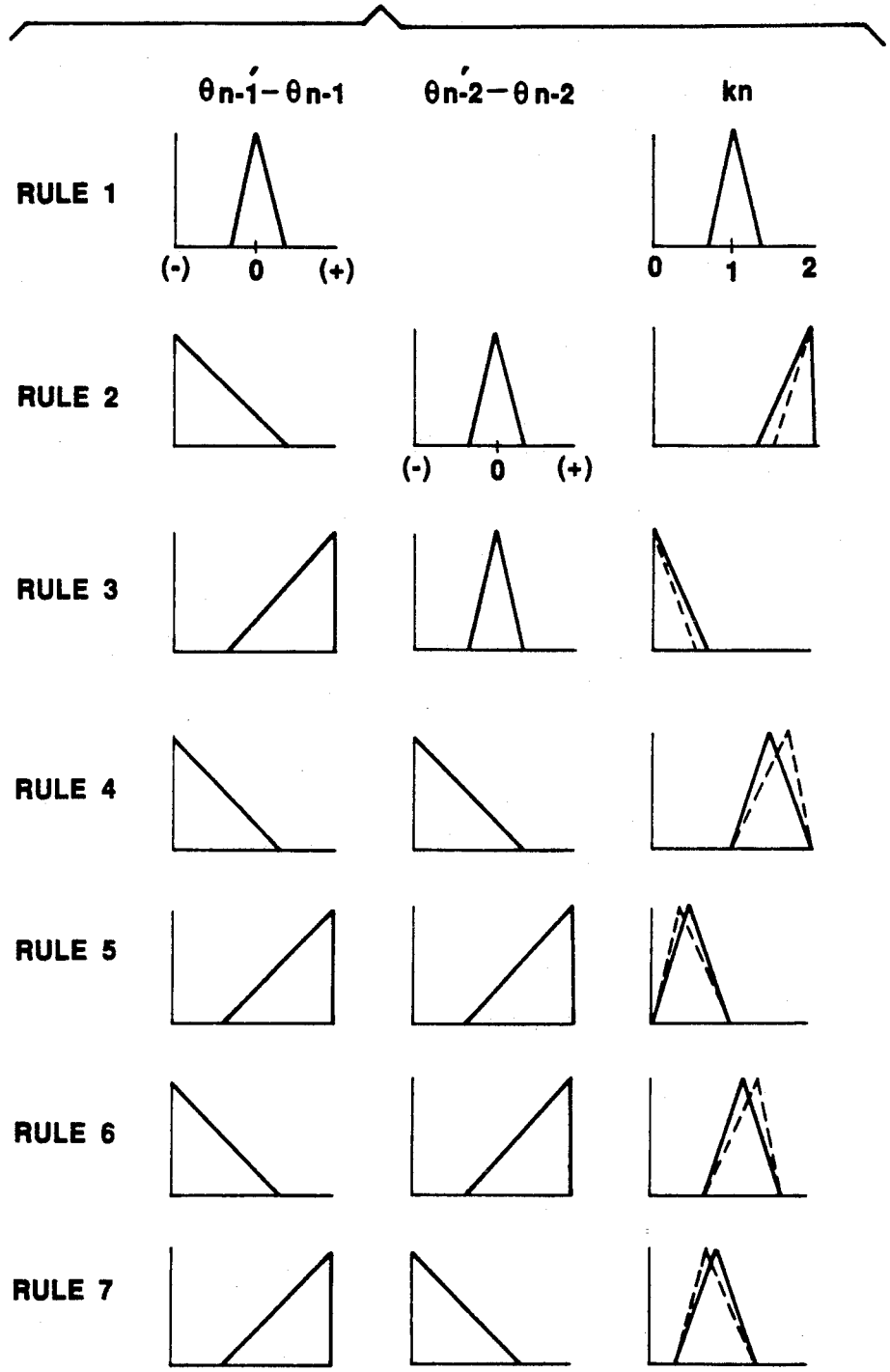
FIG. 52 is a set of explanatory charts showing fuzzy rules and membership functions in a twelfth embodiment of the present invention.

FIG. 52 is a set of explanatory charts showing fuzzy rules and membership functions in a twelfth embodiment of the present invention.

Although this embodiment has almost the same arrangement as the above eleventh embodiment, it is designed such that information of the segment number (n) is inputted to the fuzzy inference section 620 to vary the membership functions depending on the segment number (n).

Also, the arithmetic section 615 calculates the target value $\theta n$ for the n-th segment from the following arithmetic equation: $\theta n = kn\theta n - 1'$.

In other words, because kn includes a correction depending on the segment number (n), this embodiment does not contain the correction coefficient an used in the above eleventh embodiment.

Fuzzy rules in this embodiment are substantially the same as those in the eleventh embodiment as seen from FIG. 52, the membership functions in the consequent portion are somewhat different therebetween depending on the segment number n. In FIG. 52, the membership functions indicated by solid lines represent the case of n=2, and the membership functions indicated by broken lines represent the case of n=3. Since the third segment undergoes a larger load than the second segment due to weight of the insert section 601, the membership functions of the consequent portion for the third segment is set to have larger or smaller values, respectively, in large or small side than those for the second segment. Though not shown, the membership functions in the cases of n=4 and subsequent numbers are also somewhat different depending on the segment number.

The remaining arrangement, operation and advantages are the same as the eleventh embodiment.

Note that the present invention is not limited to the above eleventh and twelfth embodiments. For instance, the target value of bend quantity may be determined with the fuzzy inference based only on the difference between the target value of bend quantity and the actual bend quantity for the one-articulation earlier segment.

According to the eleventh and twelfth embodiments of the present invention, as described above, since the target value of bend angle for the segment to be bent is determined with fuzzy inference based on the difference between the target value and the measured value of bend angle for the segment nearer to the distal end that the segment to be bent, all the segments can be operated substantially in the same manner to enable smooth insertion of the insert section in spite of different loads exerted on the respective segments.

Next, a thirteenth embodiment of the present invention will be described. This embodiment is concerned with a medical irrigation system in which the quantities of supplied and sucked water (liquid or solution) are controlled by a fuzzy inference means.

When medical treatment or observation is conducted using medical equipment such as an endoscope, it is generally known to irrigate a liquid such as a physical saline solution.

Further, supply and suction of water are used in many and various applications of medical equipment.

For instance, water is supplied and sucked when calculi (stones) in the bladder, the ureter, the kidney and so forth are broken by using a ultrasonic calculus breaking device, an electric water-pressure calculus breaking device, a laser calculus breaking device, etc. Supply and suction of water are also carried out in the cases of excision using a ultrasonic scalpel device and excision of the prostate gland using an electric scalpel. In addition, when observing body cavities by an endoscope, water is supplied to ensure the clear field and sucked to remove foreign matters.

While water is supplied and sucked in many pieces of medical equipment as stated above, it is difficult to set the quantities of supplied and sucked water to optimum values depending on types of the medical equipment unless an operator has a skilled experience. This embodiment provides a medical irrigation system which allows even an unskilled operator to set optimum or nearby conditions.

Figure 53:
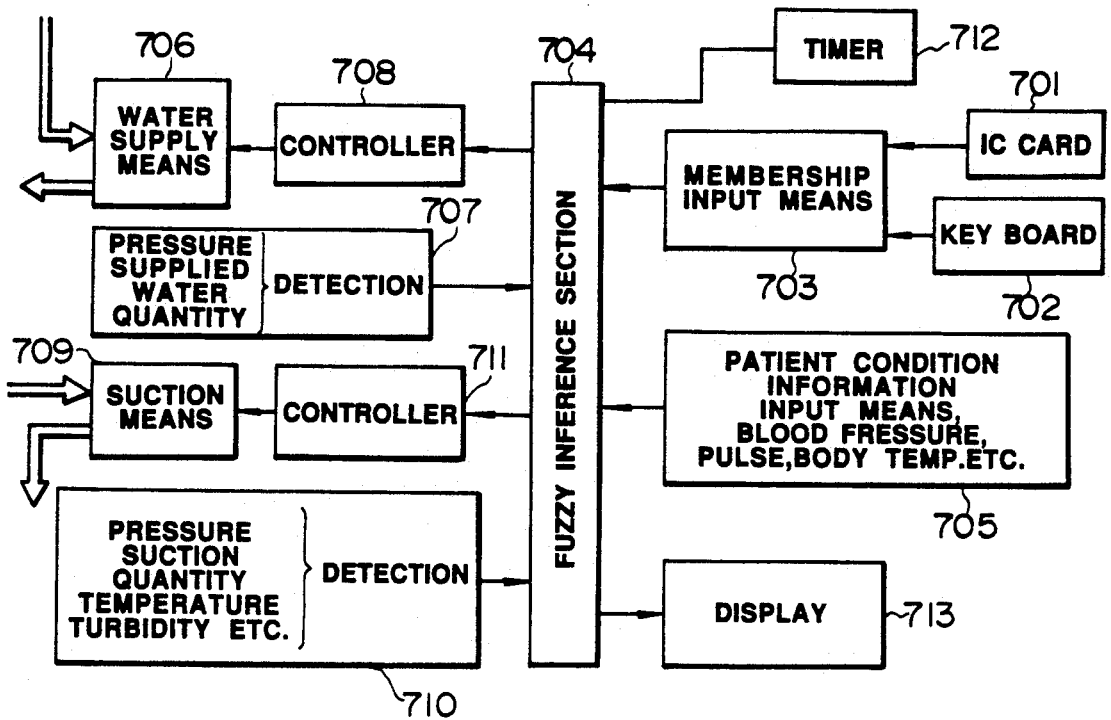

In this embodiment, as shown in a basic arrangement of FIG. 53, membership functions are inputted to a membership input means 703 from an IC card 701 storing membership functions therein, a keyboard 702 or the like, and an output of the membership input means 703 is applied to a fuzzy inference section 704 to perform fuzzy inference for specifying control rules.

As required, patient information such as blood pressure, pulse and body temperature, etc. is applied from a patient condition information input means 705 to a fuzzy inference section 704.

On the other hand, the water supplied to the patient via a water supply means 706 from a water supply container or the like is detected by a first detecting means 707, the detected pressure and the quantity of supplied water being applied to the fuzzy inference section 704. The quantity of supplied water from the water supply means 706 can be controlled by an output of the fuzzy inference section 704 via a controller 708.

The water (liquid) sucked by a suction means 709 from the patient is introduced to a discharge container (which may be the same as the water supply container depending on cases). The pressure, quantity, temperature, turbidity, etc. of sucked water are detected by a second detecting means 710 and applied to the fuzzy inference section 704. The quantity of sucked water by the suction means 709 can be controlled by an output of the fuzzy inference section 704 via a controller 711.

Based on the quantities of supplied and sucked water, the patient information and so forth, the fuzzy inference means 704 performs fuzzy inference to determine the quantities of supplied and sucked water fit for the patient from the membership patients at all times even for different types of medical treatment or equipment, and controls the quantities of supplied and sucked water by the water supply means 706 and the suction means 709 via the controllers 708, 711, respectively. The quantity of supplied water, etc. can be variably controlled in terms of time using a timer 712, as required. In addition, a result of the fuzzy inference, etc. may be displayed on a display 713.

Figure 54:
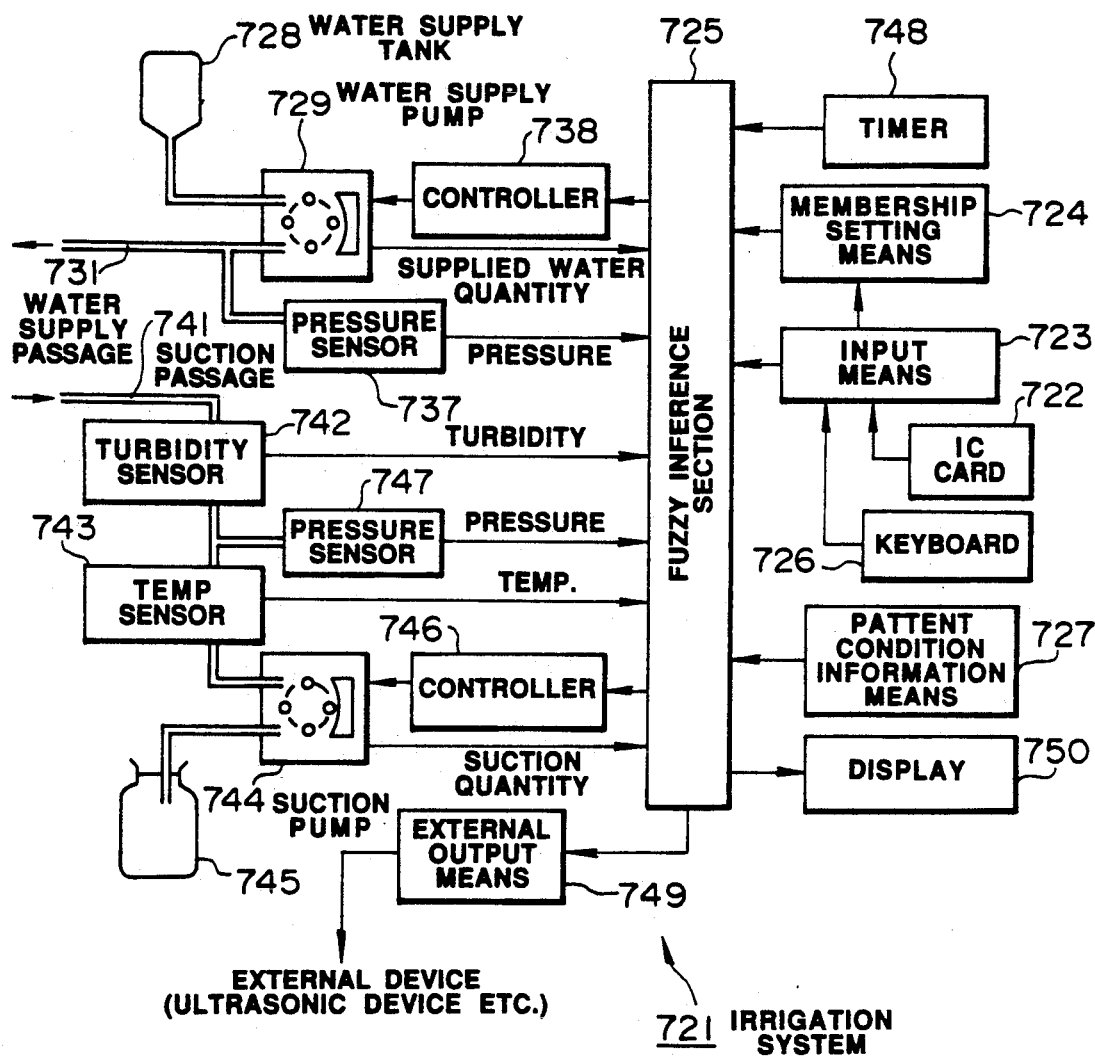

FIG. 54 shows an entire arrangement of the medical irrigation system 721 of the thirteenth embodiment based on the fuzzy inference.

An IC card 722 in which information is written to define membership functions representing control rules as shown in FIG. 58 is read by a reading unit in an input means 723 and the read information is sent to a membership setting means 724 for setting the membership functions. These membership functions are inputted to a fuzzy inference section 725 to perform fuzzy inference. The membership functions determined by the IC card 722 may be corrected or added by using a keyboard 726. The input means 723 is designed such that the input information for use in the fuzzy inference may be outputted to the fuzzy inference section 725 depending on the applications or the like.

A patient condition information means 727 is also provided to output patient condition information such as blood pressure, pulse and body temperature, etc. to the fuzzy inference section 725 for permitting the fuzzy inference fit for the patient conditions.

Figure 55:
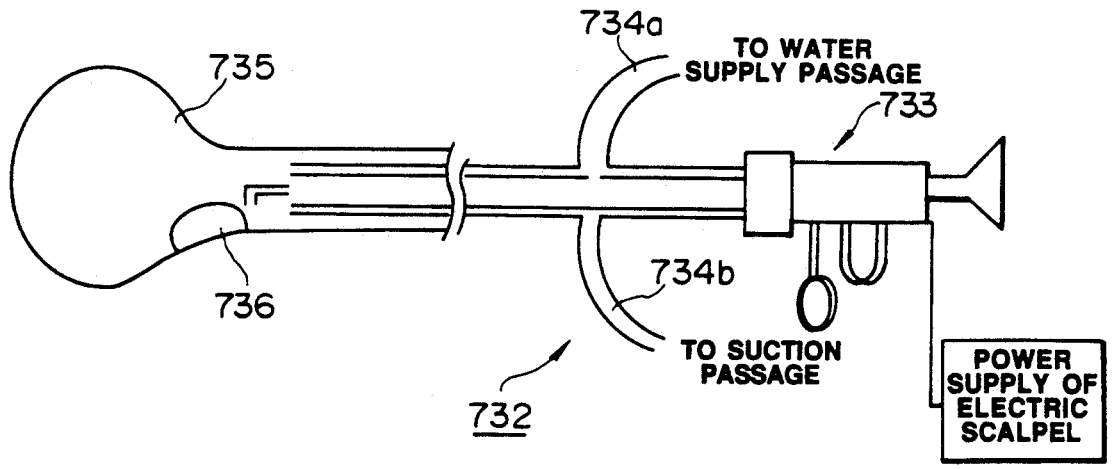

On the other hand, irrigation water (liquid) from a water supply tank 728 is introduced to the patient side by a water supply pump 729 via a water supply passage 731. In the case of an electric scalpel 732 as shown in FIG. 55, for example, the water supply passage 731 is connected to a water supply tube 734a of a resect scope 733 so that the water is supplied to the bladder 735 via the water supply tube 734a for purpose of resecting the prostate gland 736.

The pressure of supplied water in the water supply passage 731 is detected by a pressure sensor 737 and inputted to the fuzzy inference section 725 for detecting a water supply state.

The quantity of supplied water by the water supply pump 729 is also inputted to the fuzzy inference section 725.

The water supply pump 729 can control the quantity of supplied water by an output of the fuzzy inference section 725 via a controller 738. The irrigation water introduced to the patient side is sucked by a suction pump 744 through a suction passage 741 via a turbidity sensor 742 and a temperature sensor 743, and then led into a discharge tank 745 (or the water supply tank 728 depending on cases). In the case of FIG. 55, the suction passage 741 is connected to the suction tube 734b for sucking the water in the bladder 735.

The quantity of sucked water by the suction pump 744 is sent to the fuzzy inference section 725. The suction pump 744 can control the quantity of sucked water by an output of the fuzzy inference section 725 via a controller 746.

Moreover, a pressure sensor 747 is connected to the suction passage 741 so that the detected suction pressure is inputted to the fuzzy inference section 725 for detecting a suction state.

The fuzzy inference section 725 is further connected to a timer 748 to change a control manner with the fuzzy inference in terms of time.

In addition, the fuzzy inference section 725 can output a control signal to an external device such as a ultrasonic device via an external output means 749. The fuzzy inference section 725 is connected to a display 750 for displaying the membership functions and so forth.

Figure 56:
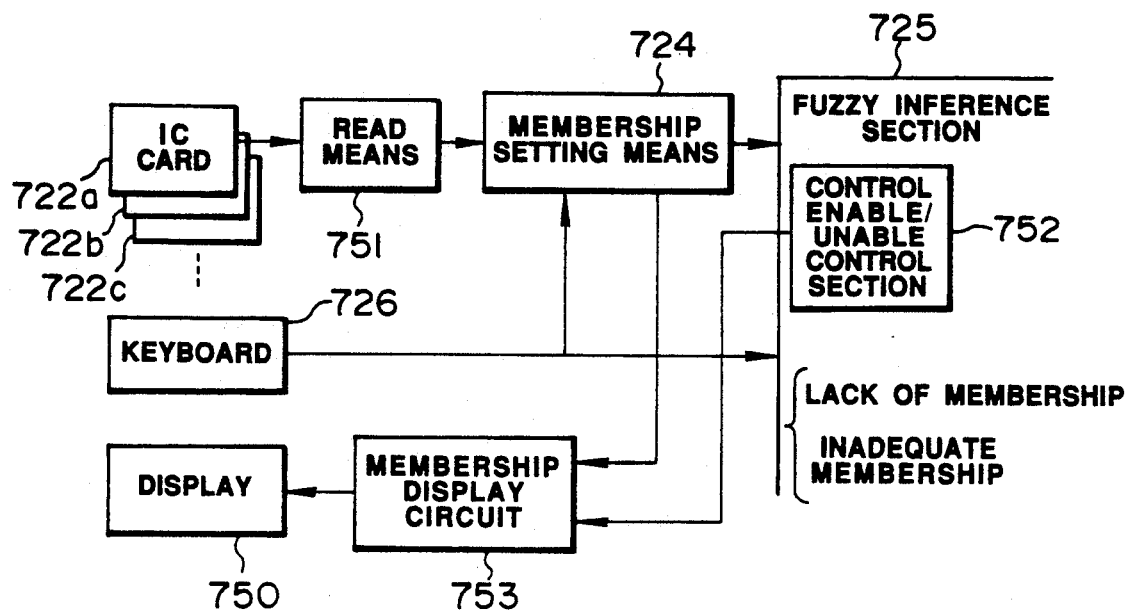

FIG. 56 shows the membership switching and inputting means in more detail.

Figure 57A:
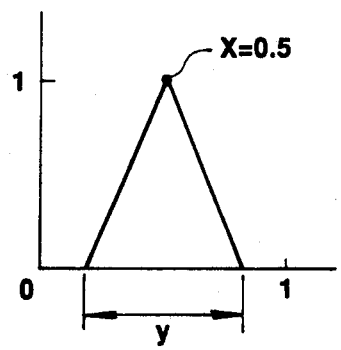
FIGS. 57(a) and 57(b) are a set of charts showing practical examples to determine membership functions, FIGS. 58(a), 58(b), 58(c), 58(d), 58(d'), 58(e) and 58(e') are a set of explanatory charts showing typical examples of control rules made up by membership functions for the electric scalpel device.
Figure 57B:
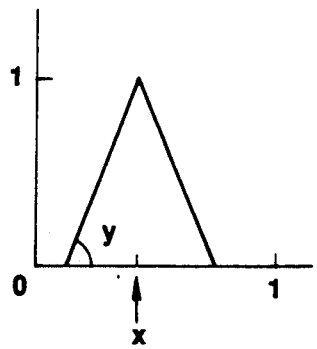

In each of IC cards 722a, 722b, . . , there is written information useful to set different membership functions per patient, surgical technique or application. A read means 751 reads membership codes (for example, water supply pressure 0001, supplied water quantity 0010, . . . ), and data x, y, i.e., the central position x and the width or inclined angle (base angle) y which jointly define each membership function, as shown in FIGS. 57a and 57b. The membership setting means 724 determines the membership functions and input them to the fuzzy inference section 725. The keyboard 726 may be used to correct the membership functions or add other membership functions. The keyboard 726 may be also be used to determine the input or output information to be inputted to or outputted from the fuzzy inference section 725, etc.

The fuzzy inference section 725 has a control enable/unable judging section 752 to judge whether fuzzy control is enabled or unabled, based on the information about the fuzzy control inputted from the membership setting means 724, the keyboard 726 or the like. At least in the case that the membership is lacking or inadequate, the display 750 displays via a membership display circuit 753 the membership functions set by the membership setting means 724 and the message indicating lack or inadequacy of the membership.

Apparently, the fact that the membership is lacking or inadequate may be also displayed.

Correction or addition of the membership functions using the keyboard 726 can be made by the central position x and the width or inclined angle y as shown in FIGS. 57a or 57b, for example.

In the medical irrigation system 721 shown in FIG. 54, the types, numbers, forms and so forth of the membership functions can be changed using the IC card 723 or the keyboard 726 to effect control suitable for each type of the various medical equipment.

Typical control items will be briefly listed below.
(1) Case of resecting the prostate gland by an electric scalpel device (see FIG. 55):
  (a) inner pressure control: the pressure is set to such a level as to expand the bladder to some extent, but not make it rupture;
  (b) clear view field: if the sucked water is turbid to some extent, the flow rate of irrigation is increased;
  (c) supplied water quantity: the quantity of supplied water is slightly reduced (to suppress the electric scalpel syndrome).
(2) Case of resecting the prostate gland by a ultrasonic scalpel:
  (a) inner pressure control; (b) clear view field; and (c) supplied water quantity may be controlled similarly to the case of an electric scalpel; (d) monitor of sucked water temperature: if the temperature rises due to ultrasonic vibrations, the quantity of supplied water is increased to restrain such a temperature rise.
(3) Case of resecting polyps or the like by an intrauterine resect scope:
  (a) inner pressure control: the set pressure is generally different from the case of an electric scalpel;
  (b) clear view field; and (c) supplied water quantity may be controlled similarly to the case of an electric scalpel.
(4) Case of observation by an endoscope:
  (a) inner pressure control; and (b) clear view field may be controlled similarly to the case of (1).
  (c) supplied water quantity: the quantity of supplied water may be set to a level slightly larger than the case of (1).

Thus, by changing the levels and/or types of control items depending on the medical equipment used, it is possible to realize an irrigation device which can be suitably used in various medical equipment.

Control items and control rules for use in the electric scalpel 732 shown in FIG. 55 are summarized in FIG. 58, by way of example.

The antecedent portion includes control items of supplied water pressure, supplied water quantity and turbidity as shown in (a), (b), (c) of FIG. 58, respectively. Depending on these values, the water supply pump and the suction pump are controlled in operation ability as shown in (d), (e) of FIG. 58, respectively.

FIG. 58 also shows five control rules R1 through R5.

With the rule R1, for example, if the supplied water pressure is high, the supplied water quantity is large and the turbidity is small, the water supply ability of the water supply pump is set to small and the suction ability of the suction pump is set to be large.

In the case of the illustrated control rules R1 through R5, when the supplied water pressure is $x_1$, the supplied water quantity is $x_2$ and the turbidity is $x_3$ as shown in FIG. 58, for example, the fuzzy inference section 725 performs MIN operations to derive the hatched areas shown in (d), (e) of FIG. 58. The hatched areas resulted from the MIN operations are subjected to MAX operations to derive membership functions as shown in (d'), (e') of FIG. 58, respectively, followed by obtaining centroids x4, x5 of those membership functions. These centroids x4, x5 are used to control the water supply ability of the water supply pump 729 and the suction ability of the suction pump 744. In that condition, the controllers 738, 746 are controlled to set the water supply ability of the water supply pump 729 to a slightly small level, and the suction ability of the suction pump 744 to a nearly medium level.

While the water supply pump 729 and the suction pump 744 are controlled based on three input information of the supplied water pressure, the supplied water quantity and the turbidity, they may be controlled in a more appropriate manner using the patent information, as mentioned above.

Accordingly, even when a less experienced operator conducts a treatment, it is possible to achieve irrigation sufficiently suitable for the medical equipment used only by setting the membership functions upon proper selection of the IC card 722, and to eliminate such an inconvenience that insufficient irrigation prevents an appropriate treatment.

Further, when an experienced operator uses the present irrigation system, its control function can be further enhanced because the operator can correct the information from the IC card 722 with key-in operation at the keyboard to update the information from the IC card 722 by the corrected information, thereby improving the membership information from the IC card 722 into a more optimum version.

Since the irrigation control is carried out using the fuzzy inference means in the above thirteenth embodiment, the proper control can be effected by a smaller scaled device than the case of using ordinary computer control. Another advantage is in that the control result is obtained with a smaller scale and in a shorter period of time, so the device has a simple construction and a small size.

Although the above explanation has been made regarding supplying and sucking water, it is also possible to perform only water supply control and let the water drain naturally in the case where the lumen is not required to expand, but filled with the supplied water.

In that case, an IC card (e.g., a segment IC card) may be used to make a setting such that the operator can set the quantity and pressure of supplied water respectively to about 10 ml/min and 800 mHg from a skilled experience by key-in operation at the keyboard 726, for example, and the water supply control by the pump as shown in FIG. 59(c) is carried out with fuzzy inference based on information about the quantity and pressure of supplied water as shown in FIGS. 59(a) and 59(b).

FIG. 60 shows a manner of the case that the irrigation system 721 of the thirteenth embodiment is applied to dissolution of gall stones.

A ultrasonic device 761 has an external applicator 762 which emits ultrasonic waves from a concave ultrasonic emitting portion. The ultrasonic waves emitted from the emitting portion are collected into a conical shape and then irradiated to the gall 763 where gall stones have been accumulated.

A liquid for dissolving the gall stones is supplied from the (medical) irrigation system 721 to the gall 763 and sucked therefrom via a catheter 764. Note that the liver 765 is near the gall 763.

The gall stones in the gall 763 are dissolved by circulating the gall stone dissolving liquid through the irrigation system 721, and this dissolution is accelerated by irradiation of the ultrasonic waves from the outside of the body.

The irrigation system 721 outputs via the external output means 749 a control signal to the ultrasonic device 761 for controlling the quantity of emitted ultrasonic waves by using the supplied liquid (water) pressure, the supplied liquid quantity, the suction quantity and the temperature as parameters, so that the quantity and temperature of irrigated liquid are each controlled so that each is held at an appropriate level.

FIG. 61 shows one example of control rules for the case where respective levels of the supplied liquid pressure, the supplied liquid quantity and the temperature, for instance, are detected to control the water supply pump and the quantity of emitted ultrasonic waves (sound pressure).

Although the suction quantity is not shown in FIG. 61, the control may be effected, by way of example, such that if the supplied liquid pressure is high, the suction quantity is set to be large, and if it is low, the suction quantity is set to be small.

The manner of changing the control rules will now be explained.

For instance, an IC card 722a writes therein information to define the membership functions representing the control rules, as shown in FIG. 58. These control rules serve to simultaneously supply and suck water in the medical irrigation system 721. In this instance, input information regarding the supplied water pressure, the supplied water quantity and the turbidity are used to perform the fuzzy inference for determining two outputs of the water supply pump and the suction pump. Then, in the case of carrying out only the water supply control, another IC card 722b is used to read the membership functions representing the control rules, as shown in FIG. 59.

In this case, input information regarding the supplied water quantity and the supplied water pressure are used to perform the fuzzy inference for determining an output of the pump.

Thus, by changing the IC cards, it is possible to rewrite the membership functions and employ the system for different surgical techniques and applications. At the same time the membership functions are rewritten, the input and output information are also switched over.

The manner of correcting and adding shapes of the membership functions by the keyboard 726, for example, will now be explained.

For instance, let it be assumed that in the control rules read from the IC card 722b, the membership function of the rule R1 for the supplied water pressure and the membership function of the rule R3 for the supplied water quantity are corrected in their shapes. The control rules read from the IC card 722b are indicated by dot lines in FIG. 62. These indicated membership functions are changed in the central positions from x1 to x11 and x2 to x21, respectively, but not in the width y. It is desirable that such a correction is properly made based on the information obtained from the experience of a skilled operator.

The keyboard 726 can also be used to add one or more other control rules. In FIG. 62, one added rule is indicated by R4. The rule R4 represents a rule by which the pump output is set to a smaller level for old persons than for young persons, by way of example.

Thus, this embodiment is designed to easily enable addition of new rules and input information by key-in operation at the keyboard 726.

FIG. 63 shows an inference result d" after correction and an inference result e" before correction in the case of using the control rules R1, R2, R3.

As input means for setting the membership functions, a modem or the like may be used to permit remote entry, in addition to the IC card and the keyboard. As the patient information input means, a modem or the like may also be used to input the patent information from hospitals and so forth which are holding (keeping) it, when the information peculiar to patients cannot be inputted from IC cards.

According to the thirteenth embodiment, as described above, since the water supply and suction means are controlled by providing the membership function input means to set control rules for controlling the water supply and suction means, and the fuzzy inference means for performing the fuzzy inference based on the membership functions, supply and suction of water can be controlled properly depending on the applications, patients, surgical techniques and the like.

Next, a fourteenth embodiment of the present invention will be described.

This embodiment is concerned with an ultrasonic diagnosis device which includes an STC control circuit to change an amplification factor of a reception signal with fuzzy inference depending on an elapsed time until echo reception.

Heretofore, there has been known an ultrasonic diagnosis device used to diagnose tissues, organs and others in the body by utilizing ultrasonic waves. In this ultrasonic diagnosis device, the ultrasonic waves reflected by deeper portions of an object have a lower signal level owing to attenuation of ultrasonic waves in the living body. For the reason, there has been conventionally practiced a gain correction of the reception signal that is called STC (sensitivity time control). This STC serves to eliminate differences in the magnitude of reception signal caused by attenuation to display an image of the object with uniform brightness if its medium is constant acoustically, by suppressing sensitivity (amplification factor) for an area near the object surface and increasing sensitivity (amplification factor) for a deeper or farther area.

In conventional STC control, an STC control curve indicating the relationship between a diagnosis distance and an amplification degree is generated at the same time as transmission of ultrasonic waves, and the amplification factor of a reception signal of the ultrasonic waves is changed to follow the STC control curve depending on an elapsed time corresponding to the diagnosis distance.

However, when an ultrasonic endoscope or the like provided with an ultrasonic oscillator at the distal end of an insert section of the endoscope is used to conduct ultrasonic observation by radial scan from a body cavity, for example, the ultrasonic oscillator is not always in close contact with tissues in the body cavity, leading to that the distance between the surface of tissues in the body cavity and the rotating surface of the ultrasonic oscillator may change per scan line. In such a case, attenuation is not so problematic for an ultrasonic medium such as water present between the ultrasonic oscillator and the surface of tissues in the body cavity. But, if the ultrasonic medium is tissues in the body cavity, the gain or amplification factor must be increased with a distance from the surface of tissues in the body cavity because it exhibits large attenuation. Thus, when the distance between the surface of tissues in the body cavity and the rotating surface of the ultrasonic oscillator may change per scan line, the STC control curve is required to be changed correspondingly per scan line. This kind of control cannot be achieved by a conventional manual adjustment. Furthermore, since attenuation of ultrasonic waves is different depending on ultrasonic frequencies, it is also required for the distance-dependent gain to be increased as the frequency goes higher. The prior art could not deal with the above problems. The fourteenth embodiment can overcome those problems.

Figure 64:
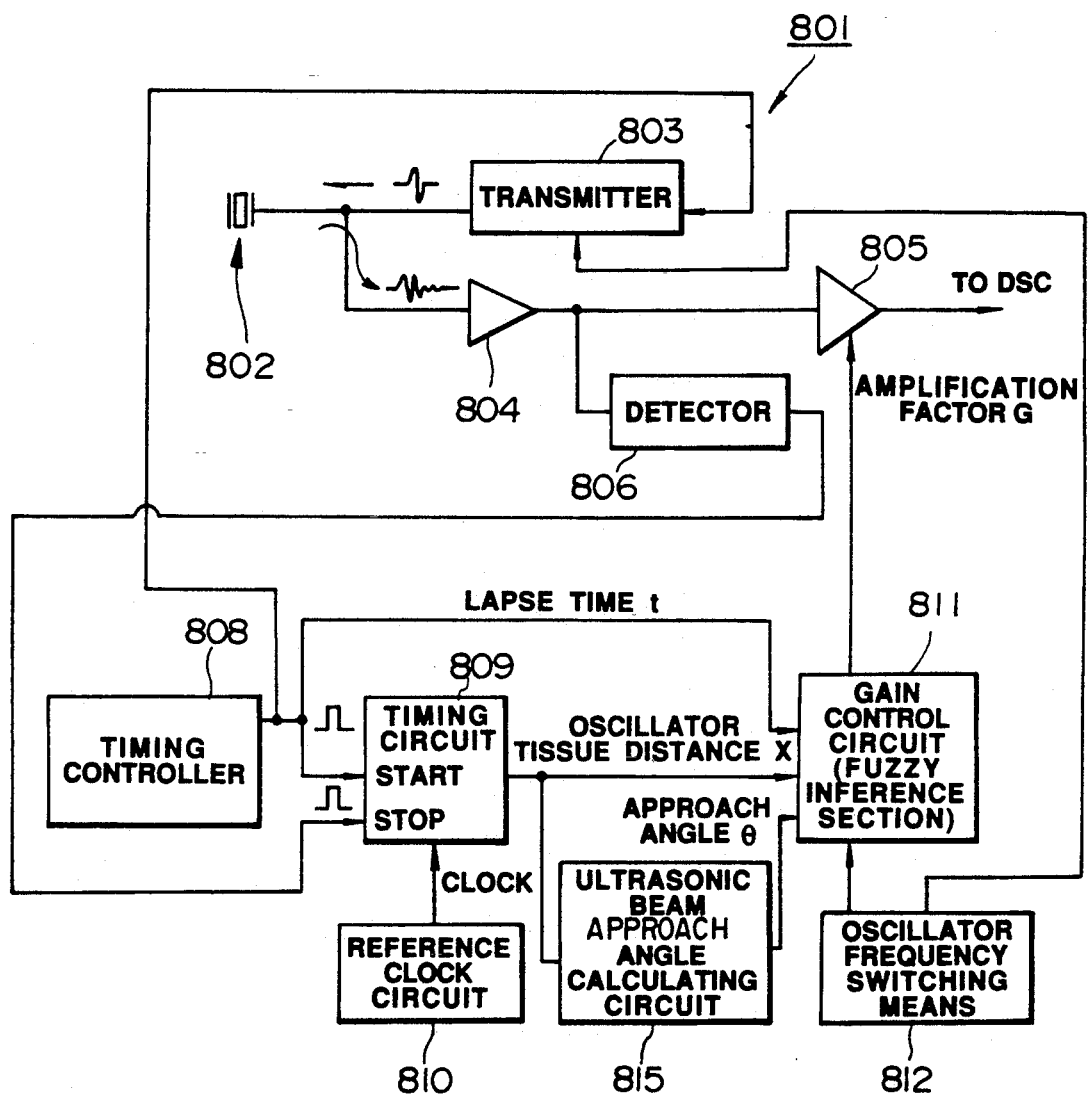
Figures 65A, 65B, 65C, 65D:
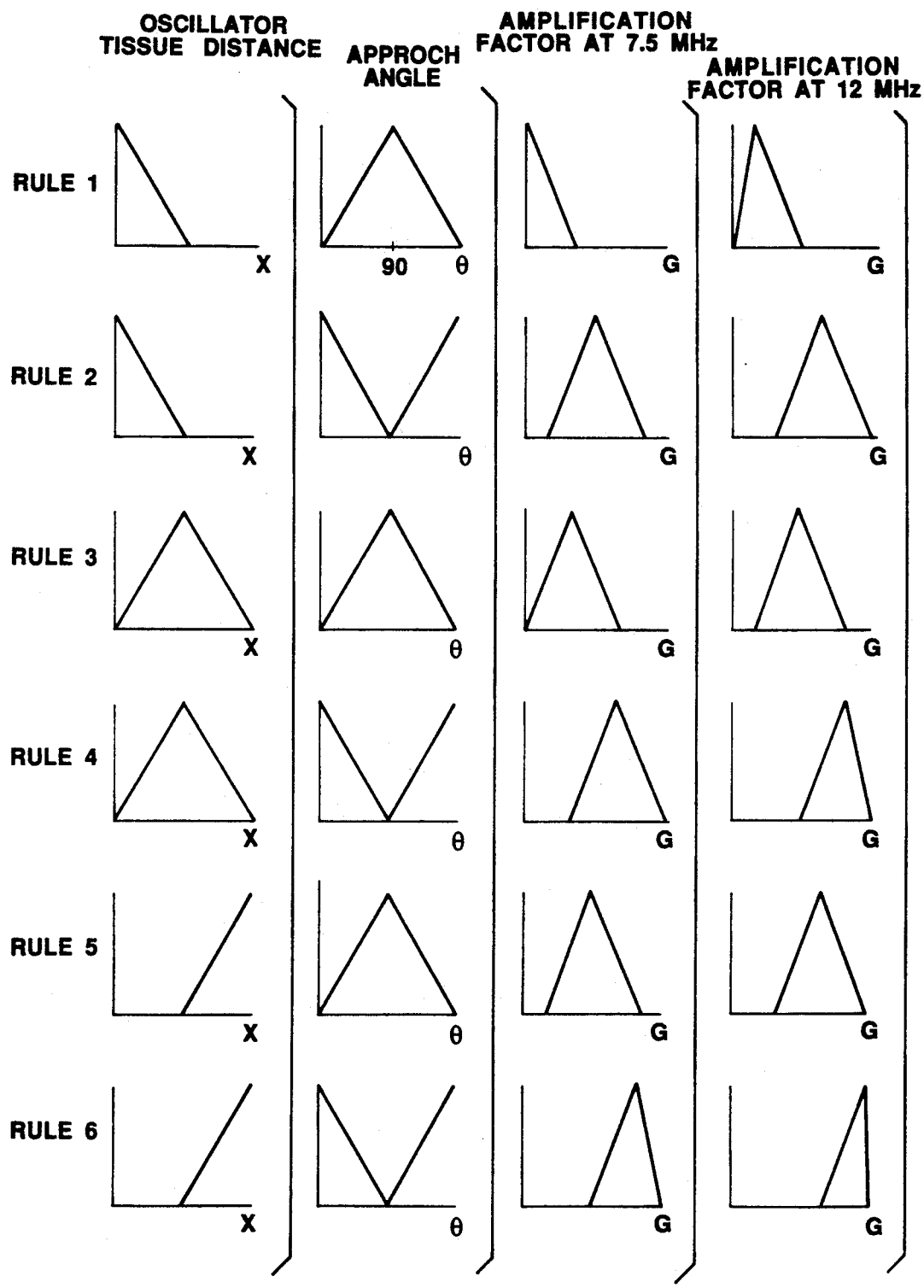

FIG. 64 is a block diagram showing an arrangement of the ultrasonic diagnosis device according to the fourteenth embodiment of the present invention.

As shown in FIG. 64, an ultrasonic diagnosis device 801 comprises a ultrasonic oscillator 802 serving to emit ultrasonic waves and also detect an echo, the ultrasonic oscillator 802 being connected to a transmitter 803 and a preamplifier 804. The transmitter 803 receives a trigger pulse from a timing controller 808 and transmits a ultrasonic pulse to the ultrasonic oscillator 802, whereupon the ultrasonic oscillator 802 generates ultrasonic waves. The ultrasonic waves are emitted into a living body and returned as an echo by being reflected from a tissue interface of the living body. The echo is converted by the ultrasonic oscillator 802 into an electric signal which is then amplified as a reception signal by the preamplifier 803. The ultrasonic oscillator 802 is designed to make a linear, sector or radial scan in a mechanical or electronic manner. An output signal of the preamplifier 804 is applied to both a variable gain amplifier 805 and a detector 806. An output of the variable gain amplifier 805 is sent to a not shown DSC (digital scan converter). The DSC serves to store the reception signal in the form of a digital quantity to be read as a TV video signal therefrom. The video signal is inputted to a monitor so that an ultrasonic tomographic image is displayed on the monitor.

The trigger pulse from the timing controller 808 is also applied to a start terminal (START) of a timing circuit 809. Applied to a stop terminal (STOP) of the timing circuit 809 is an output of the detector 806. The timing circuit 809 counts clock pulses (CLOCK) from a reference clock circuit 810 during a period from application of the trigger pulse from the timing controller 808 to application of the signal from the detector 806. Because the detector 806 first detects the reception signal of an echo reflected by the tissue surface of the living body (hereinafter referred to as a first echo), the timing circuit 809 measures a time lapsed from the emission of ultrasonic waves from the ultrasonic oscillator 802 to reception of the first echo. This time corresponds to a distance X between the ultrasonic oscillator 802 and the tissue surface of the living body (hereinafter referred to as an oscillator-tissue distance X), which implies that the timing circuit 809 measures the oscillator-tissue distance X. This information of the oscillator-tissue distance X is inputted to a gain control circuit 811 formed by a fuzzy inference section. The gain control circuit 811 also receives from the timing controller 809 a time t lapsed after the emission of ultrasonic waves.

In this embodiment, the frequency of ultrasonic waves emitted from the ultrasonic oscillator 802 can be switched over between 5 MHz and 12 MHz, for example. The frequency switching is instructed by an oscillator frequency switching means 812 an output of which is inputted to the transmitter 803 for controlling the transmitter 803 to change over the frequency of ultrasonic pulses emitted therefrom, and also to the gain control circuit 811.

There is further provided a ultrasonic beam approach angle calculating circuit 815 for determining an approach angle of the ultrasonic beam into tissues of the living body. The information of the oscillator-tissue distance X from the timing circuit 809 is inputted to the ultrasonic beam approach angle calculating circuit 815 which collects the oscillator-tissue distances X for several scan lines preceding that one for which the approach angle is to be determined, and determines changes in these distances to calculate the approach angle $\theta$. Information of the approach angle $\theta$ is inputted to the gain control circuit 811. Based on the information of the oscillator-tissue distance X, the lapsed time t, the ultrasonic frequency and the approach angle $\theta$, the gain control circuit 811 performs fuzzy inference and controls an amplification gain G of the variable gain amplifier 805 using an output value of the fuzzy inference.

If the approach angle of the ultrasonic beam into tissues of the living body (i.e., the angle formed between the ultrasonic beam and the tissue surface of the living body) is small, the reception signal of ultrasonic waves becomes weak even with the oscillator-tissue distance X remained constant and, therefore, this reduction in the signal level is required to be corrected. To this end, this embodiment is designed so as to vary change characteristics of the amplification factor with respect to time depending on the approach angle $\theta$.

The fuzzy inference to be carried out in a fuzzy inference section within the gain control circuit 811 of this embodiment will be explained below. In this embodiment, fuzzy rules are different between 7.5 MHz and 12 MHz of the ultrasonic frequency. The following six rules, for example, are adopted as fuzzy rules in the case of 7.5 MHz.

1. If the oscillator-tissue distance is short and the approach angle is large, then the amplification factor is set to be much smaller than the value of the standard STC control curve.
2. If the oscillator-tissue distance is short and the approach angle is small, then the amplification factor is not changed from the value of the standard STC control curve.
3. If the oscillator-tissue distance is medium and the approach angle is large, then the amplification factor is set to be a little smaller than the value of the standard STC control curve.
4. If the oscillator-tissue distance is medium and the approach angle is small, then the amplification factor is set to be a little larger than the value of the standard STC control curve.
5. If the oscillator-tissue distance is far and the approach angle is large, then the amplification factor is not changed from the value of the standard STC control curve.
6. If the oscillator-tissue distance is far and the approach angle is small, then the amplification factor is set to be relatively larger than the value of the standard STC control curve.

Note that when the approach angle is over 90°, it is interpreted to be smaller as the angle value approaches 180°.

Fuzzy rules for 12 MHz have the same antecedent portion as fuzzy rules for 7.5 MHz, but have the consequent portion below.
1. The amplification factor is set to be relatively smaller than the value of the standard STC control curve.
2. The amplification factor is set to be a little larger than the value of the standard STC control curve.
3. The amplification factor is not changed from the value of the standard STC control curve.
4. The amplification factor is set to be relatively larger than the value of the standard STC control curve.
5. The amplification factor is set to be a little larger than the value of the standard STC control curve.
6. The amplification factor is set to be much larger than the value of the standard STC control curve.

Note that in the consequent portion the magnitude of amplification factor is defined as follows; very smaller<relatively smaller<a little smaller<not changed<a little larger<relatively larger<very larger.

Thus, in this embodiment, the amplification factor is set to be a little larger as the oscillator-tissue distance becomes greater, to be larger as the approach angle becomes smaller, and to be a little larger in the case of 7.5 MHz than the case of 12 MHz. Furthermore, the standard STC control curve is changed depending on the oscillator-tissue distance.

The fuzzy inference section within gain control circuit 811 switched over a group of fuzzy rules depending on the frequency, simultaneously applies the aforementioned six rules to the oscillator-tissue distance X and the approach angle $\theta$ both applied thereto, executes MIN operations to determine a degree of coincidence in the antecedent portion of each rule for respective inputs, and further employs the resulting degree as a weight for the consequent portion of that rule. Then, a MAX operation is executed to synthesize the consequent portions of all the rules and a centroid value of the resulting membership function, for example, is derived as an output value. The above execution of the fuzzy rules and arithmetic operation of the inference result can be implemented at a high speed by using a fuzzy chip. Based on the output value, the standard STC control curve is corrected. When correcting the standard STC control curve with the fuzzy inference, since the attenuation rate between the ultrasonic oscillator 802 and the tissue surface of the living body is not dependent on the oscillator-tissue distance and the approach angle, the amplification factor is not corrected during the lapse time corresponding to the oscillator-tissue distance X, but corrected after that lapse time.

Thus, with this embodiment, the STC control curve can be easily changed in a shorter period of time based on the oscillator-tissue distance X, the approach angle $\theta$ and the frequency of ultrasonic waves.

Incidentally, the present invention is not limited to the foregoing fourteenth embodiment. In the case of controlling the amplification factor based on the oscillator-tissue distance and the frequency, for example, the STC control curve may be controlled by defining a plurality of fuzzy rules each of which comprises the antecedent portion specifying conditions of the oscillator-tissue distance and the frequency, and the consequent portion specifying a degree of correction in the amplification factor, and by carrying out fuzzy inference.

According to the fourteenth embodiment, as described above, since change characteristics of the amplification factor of the reception signal with respect to time is varied depending on the positional relationship between the ultrasonic oscillator and the object surface and also the frequency of ultrasonic waves, there can be obtained an advantage that the appropriate STC can be always effected irrespective of the positional relationship between the ultrasonic oscillator and the object surface and also the frequency of ultrasonic waves.

Next, a fifteenth embodiment of the present invention will be described.

This embodiment is concerned with an industrial endoscope system in which the degree of defect of an inspected object is determined by judging an inspection result with a fuzzy inference means.

For instance, when inspecting blades in a jet engine, if any blade is damaged, defected or discolored, it has been customary to judge an expected risk from the size of damage and the degree of discoloration, and to replace the blade with a new one depending on the expected risk.

Because such a judgment is made by an inspector, there has been a likelihood that the judgment may become different depending on individuals and thus may be erroneous. In a jet engine or the like, particularly, an appropriate judgment by non-destructive inspection using an endoscope is necessitated for purpose of ensuring safety. This embodiment is to provide an industrial endoscope system with which an importance of defect, such as an expected risk, can be properly judged without causing differences depending on individuals.

Figure 66:
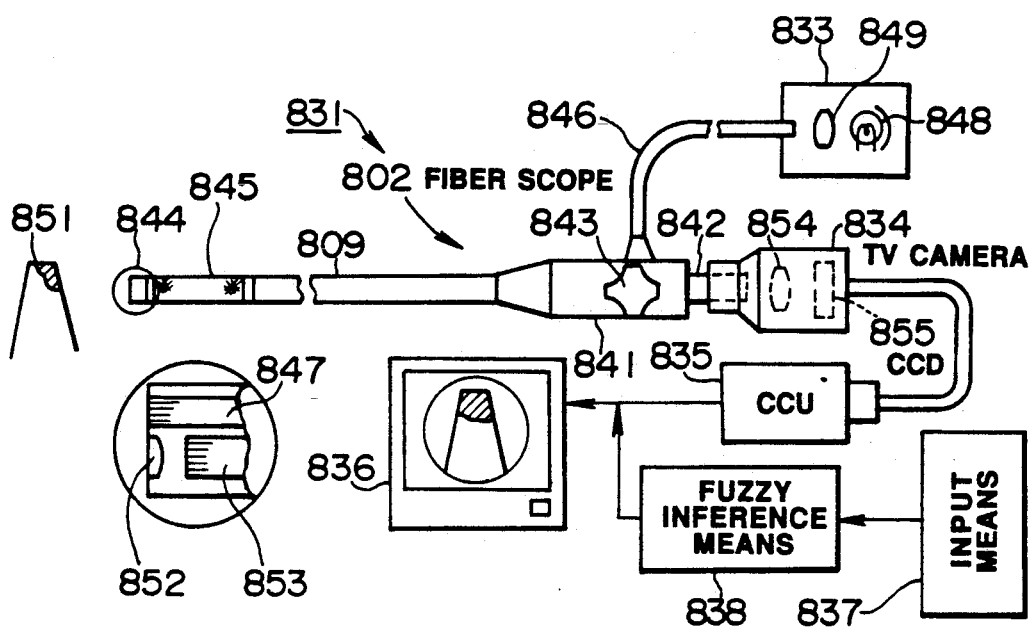

FIG. 66 shows an industrial endoscope system 831 of the fifteenth embodiment equipped with a means for carrying out fuzzy inference. This system 831 comprises a fiber scope 832 as an optical endoscope, a light source unit 833 for supplying illumination light to the fiber scope 832, a TV camera 834 fitted to the fiber scope 833, a camera control unit (hereinafter abbreviated as a CCU) 835 for processing a signal from the TV camera 834, a TV monitor 836 displaying a video signal outputted from the CCU 835, input means 837 for inputting information about inspection date, inspected location, blade state and so forth, and a fuzzy inference means 838 for carrying out the fuzzy inference an inference result inferred by the fuzzy inference means 838 being displayed on the TV monitor 836.

The fiber scope 832 has a slender insert section 839 and a thick operating section 841 formed adjacent to a rear end of the insert section 839. The TV camera 834 can be fitted to an eyepiece 842 at rear end of the operating section 841.

The operating section 841 is provided with an angle knob 843 and, by turning the angle knob 843, a bendable section 845 provided near a distal end 844 of the insert section 839 can be bent.

A light guide 847 for transmitting illumination light therethrough is penetrated through the insert section 839 and a light guide cable 846 extended from the operating section 841. When a connector of the light guide cable 846 is connected to the light source unit 833, a beam of white light from a light source lamp 848 is condensed by a condenser lens 849 to be irradiated to an incident end face of the light guide 847. The illumination light transmitted through the light guide 847 is emitted from its opposite end face of the distal end 844 toward an object locating in front of the emergent end face. An optical image of an engine blade 851, for example, as an object is brought under illumination, focused by an objective lens 852 provided in the distal end 844 on the focal plane of the objective lens 852. One end face of the image guide 853 is disposed in the focal plane so as to transmit the optical image until the other end face thereof located near the eyepiece 842. An eyepiece lens (not shown) is disposed in the eyepiece 842 so that the transmitted optical image may be observed in an enlarged scale.

When the TV camera 834 is fitted to the eyepiece 842, the optical image is focused on the CCD 855 by a focusing lens 854. The CCD 855 photoelectrically converts the optical image to be temporarily stored in the form of signal charges therein. Upon application of a drive signal from the CCU 835, an electric signal is read out of the CCD 855 and processed by a signal processing circuit (not shown) in the CCU 835 to be converted into a standard video signal for displaying an image of the object, i.e., the blade 851, on the TV monitor 836 in colors.

Accordingly, while observing the image, the inspector of the blade 851 can, using the input means 837 such as a keyboard, input the type of blade, specify the fuzzy rule to be used out of fuzzy rules each prepared per inspected location, and further enter the results of inspection items such as flow size, flaw position, degree of discoloration, and coating condition (extent of peeling-off).

Figure 67:
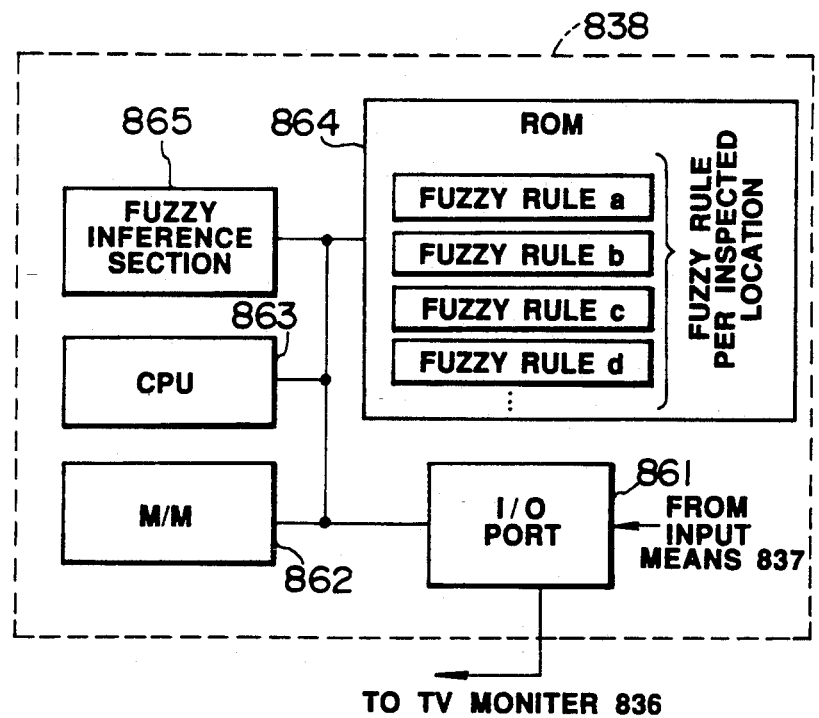

FIG. 67 shows an arrangement of the fuzzy inference means 838 for carrying out fuzzy inference based on the entered results of the inspection items.

The data entered through the input means 783 is stored in a temporary memory 862 via an I/O port 861. Based on the data entered via the I/O port 861 and indicating the type of blade, a CPU 863 selects a corresponding fuzzy rule i out of a ROM 864 in which fuzzy rules a, b, c, d, ... each per inspected location (that is, the type of blade in this case) are written in advance. In engine inspection, standards of the inspection are usually different depending on the type of blade (location). Therefore, the fuzzy rules a, b, c, d, ... each per type of blade are prepared and written in the ROM 864, enabling the system to handle any blade type.

Then, based on the entered data of results of the inspection items, the fuzzy inference section 865 executes a fuzzy inference process using the fuzzy rule i to determine an importance such as necessity of replacing the blade with a new one. The inference result is outputted to the TV monitor 836 via the I/O port 861.

Figures 68A, 68B, 68C, 68D:
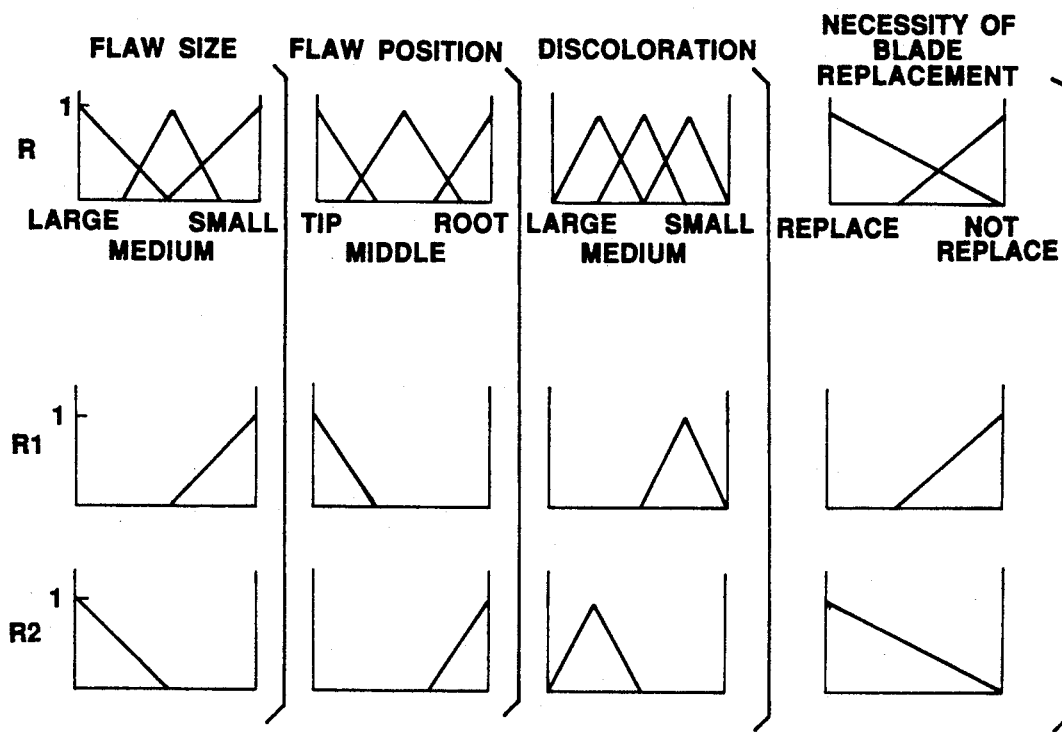
Figure 69:
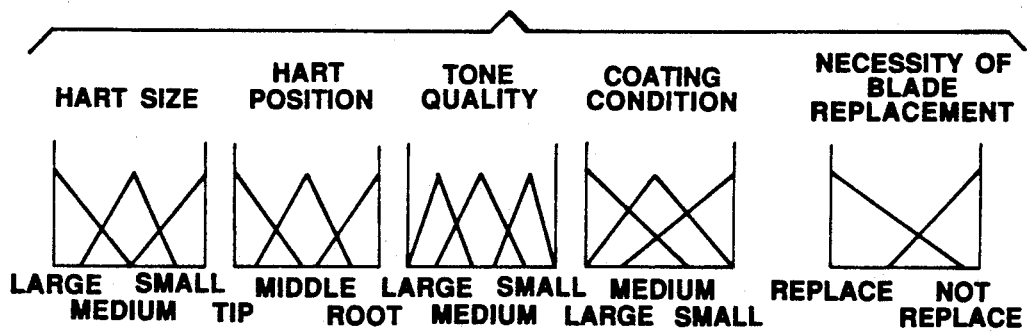

The fuzzy rule for use in the fuzzy inference based on the results of the inspection items is expressed by membership functions shown in FIG. 68 or 69, for example.

In FIG. 68, there are three inspection items; (a) flaw size, (b) flaw position, and (c) degree of discoloration. These items make up the antecedent portion, and degrees of coincidence of the items define the form of a function indicating the necessity of blade replacement. Because there are three inspection items, each is therefore divided into three stages and expressed by functions giving the triangular form as shown. Accordingly, while rules corresponding to $3^3=27$ items in total are contemplated in this case, those rules which are considered to be effective are extracted out of all the possible rules and used as a fuzzy rule group. Two typical rules are shown at R1 and R2, by way of example.

With the rule R1, if the flaw size is small, the flaw position is nearer to the tip end, and the degree of discoloration is small, then a membership function of the fuzzy rule indicating "no replacement" is resulted.

On the contrary, with the rule R2, if the flaw size is large, the flaw position is nearer to the root end, and the degree of discoloration is large, then a membership function of the fuzzy rule indicating "replacement" is resulted.

In this way, a fuzzy rule group is made up by the membership functions representing the rules which are considered to be effective, and the fuzzy inference section 865 carries out the fuzzy inference using the fuzzy rule group. The manner of the fuzzy inference has been explained before and further description is omitted here.

FIG. 69 shows the case that another item of coating condition is included in addition to the three inspection items in FIG. 68. Based on respective results of those four inspection items jointly making up the antecedent portion, an inference result representing necessity of blade replacement is derived in the consequent portion. While rules corresponding to $4^3 = 256$ items in total are contemplated in the case of FIG. 69, it is practical that those rules which are considered to be effective are extracted out of all the possible rules to form a fuzzy rule group.

According to the fifteenth embodiment, when the results of the inspection items are entered, these entered results of the inspection items are judged synthetically, enabling it to obtain an effective decision without depending on differences between individuals.

Furthermore, according to the fifteenth embodiment, since the necessity of blade replacement and so forth are judged using the fuzzy inference means 838, the more appropriate decision result can be provided with the device of smaller scale and in a shorter period of time.

Figure 70:
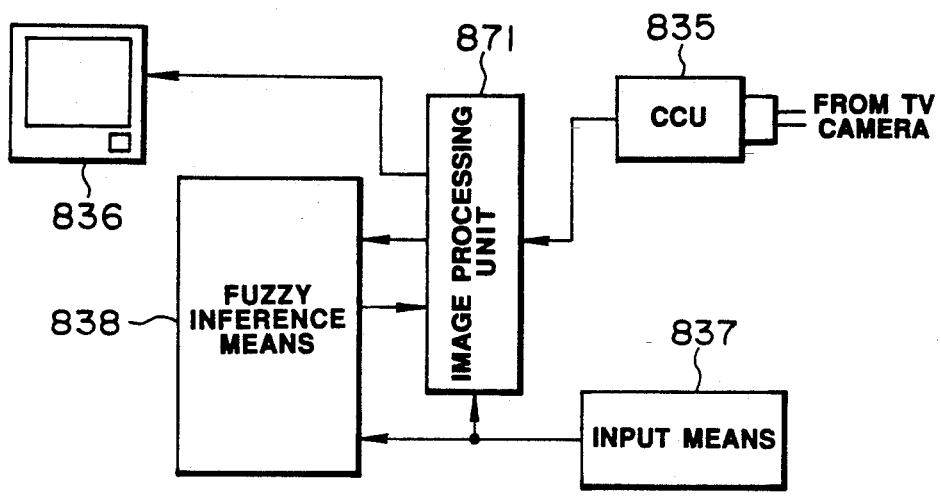

FIG. 70 shows an arrangement of primary components of a sixteenth embodiment of the present invention.

In this embodiment, inputted to the fuzzy inference means 838 are the data of size and position of flaws resulted from image processing by an image processing unit 871, as well as the data entered from the input means 837.

Figure 71:
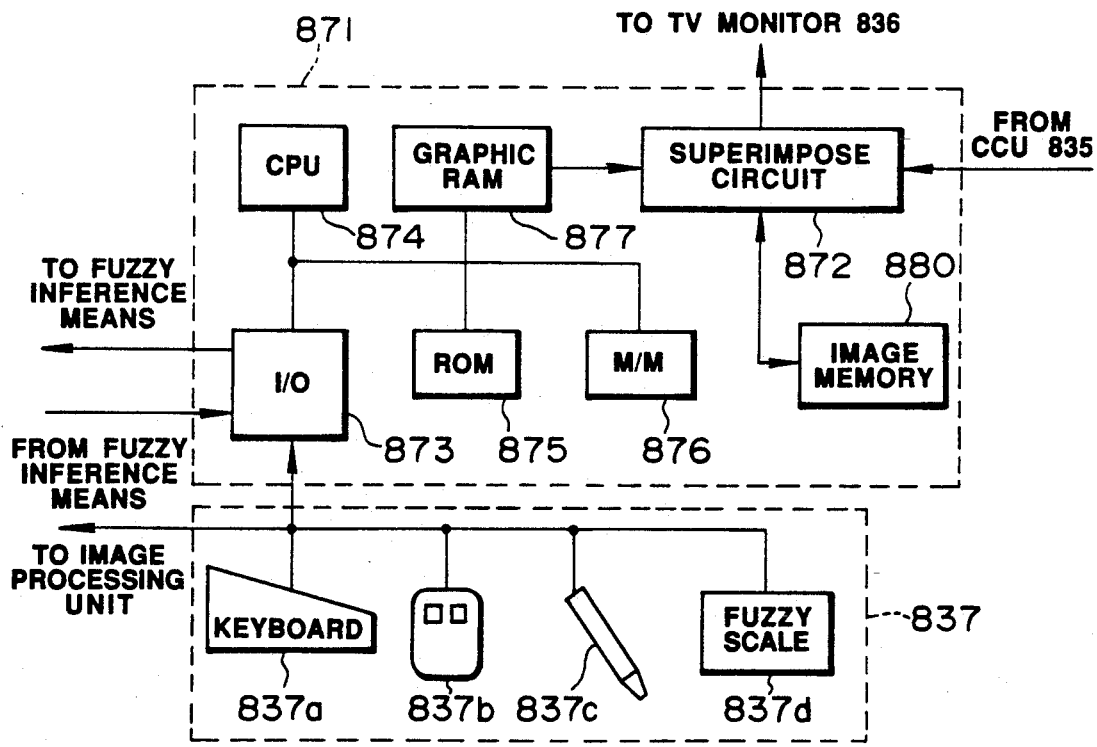

As with the fifteenth embodiment, an electric signal from the TV camera 834 fitted to the fiber scope 832 is converted into a video signal by the CCU 835. The video signal of the CCU 835 is inputted to the image processing unit 871 and outputted to the TV monitor 836 via a superimposing circuit 872 as shown in FIG. 71.

The image processing unit 871 has a keyboard 837a, a mouse 837b, a light pen 837c and a fuzzy scale 837d as the input means 871, and can enter data to an I/O port 873 using any means. The image processing unit 871 also has a CPU 874 and functions to measure a length of any portion such as a flow 878 displayed on a monitor screen 836A as shown in FIG. 72, by using a ROM 875 storing programs therein, a working memory 876 and a graphic RAM 877.

Figure 72:
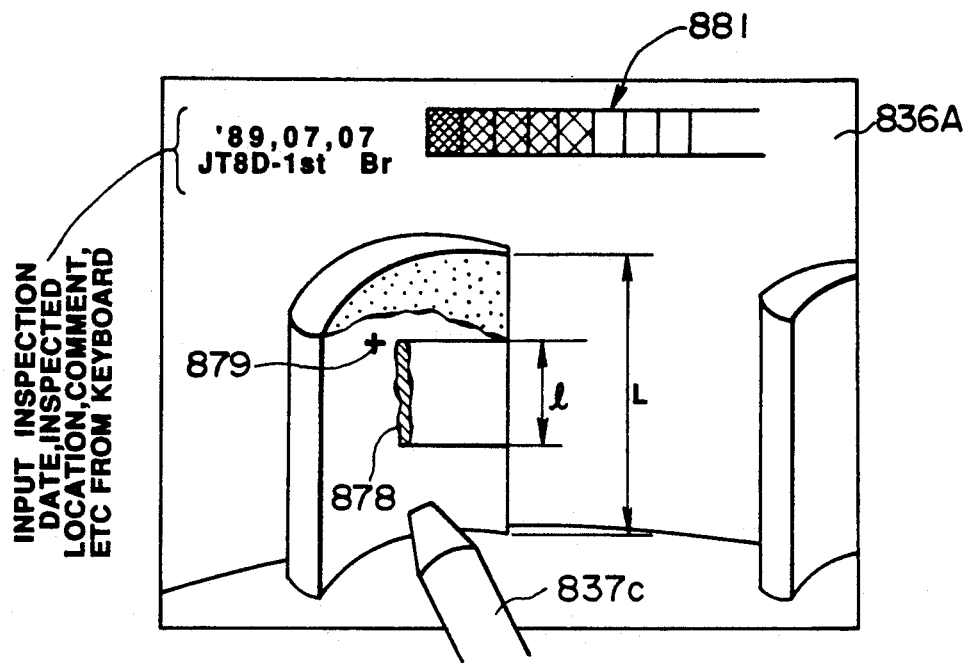

In the case of blade inspection, for example, the actual length Lo of dimension L of a blade to be inspected is known as shown in FIG. 72 upon entry of data indicating the type of blade, etc. Accordingly, by comparing size l of the flaw 878 on the monitor screen 836A with the known dimension L, the actual flaw size lo can be determined with proportional allotment or other method. Thus, the actual flaw size lo is given:

$$lo = l \times Lo/L$$

The size to be determined on the monitor screen 836A can be designated by moving a cursor 879 (e.g., through the mouse 837b) or utilizing the light pen 837c. Data regarding the flaw position can be obtained just by designating a central position of the flaw 878 on the monitor screen 836A by means of the cursor 879, the light pen 837c or the like.

Further, the image processing unit 871 has an image memory 880 for a freeze picture so that the size and position of a flaw may be designated using a freeze picture presented by storing the video signal from the CCU 835 in the image memory 880.

On the other hand, data of degree of discoloration can be entered by the inspector who compares the discoloration with a color bar 881 displayed at the top of the monitor screen 836A and enters the compared result using the fuzzy scale 837d, for example.

Data of coating condition can be entered by the inspector who observes the coating condition and enters the observed result using the fuzzy scale 837d, for example.

Figure 73:
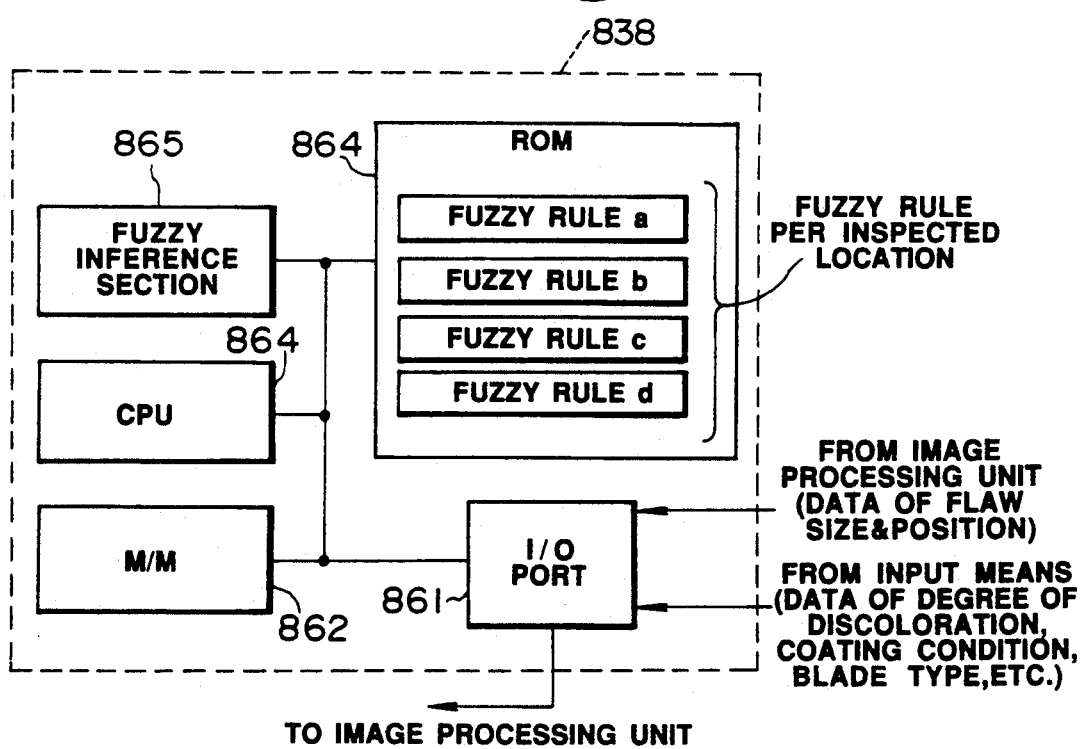

In this embodiment, therefore, inputted to the fuzzy inference means 838 the data of the size and position of flaw from the image processing unit 871, as well as the data of degree of discoloration and coating condition from the input means 837, as shown in FIG. 73. In addition, the blade type, inspection date, comment, etc. may be entered from the input means 837 such as the keyboard.

Incidentally, the fuzzy inference means 838 shown in FIG. 73 is different from that shown in FIG. 67 in an input section of the I/O port 861 and an output section from the I/O port 861. Thus, the former means has substantially the same arrangement as the latter means and their components are denoted by the same reference numerals.

This sixteenth embodiment is modified to input the data of size and position of flaw to the fuzzy inference means from the image processing device 871, and operates similarly to the fifteenth embodiment in the remaining points. Also, the sixteenth embodiment has a similar advantage to the fifteenth embodiment.

Figure 74:
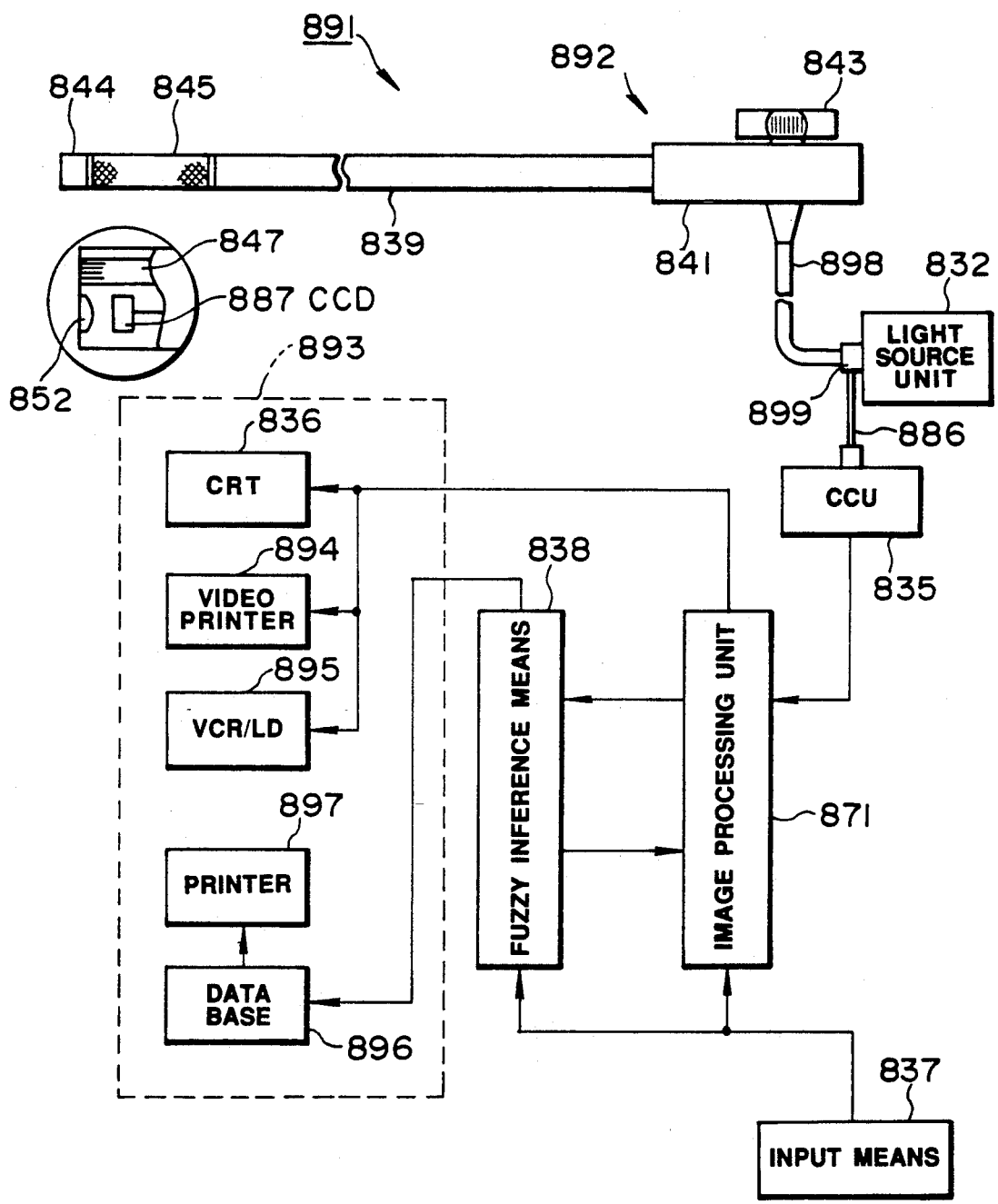
FIG. 74 is an entire arrangement view of a seventeenth embodiment.

FIG. 74 shows an industrial endoscope system 891 of a seventeenth embodiment.

This embodiment has a data base in an output means, permitting all the inspection results of one engine to be outputted together in the form of a table or graph.

The system 891 comprises an electronic endoscope 892, the light source unit 833, the CCU 835, the image processing unit 871, the input means 837, and an output means 893.

In other words, applied to the CCU 835 is a signal not from the TV camera 834 in the sixteenth embodiment, but from an image sensing means of the electronic endoscope 892.

An output signal of the image processing unit 871 is also applied to a video printer 894 and VCR/LD 895 in addition to the TV monitor (abbreviated as CRT here) 836, so that an image of the object location may be printed out, recorded/reproduced, as well as displayed.

Further, an output signal of the fuzzy inference means 838 is applied to a data base 896 to record all data of the inspection results obtained by the fuzzy inference, allowing the inspection results to be outputted together to a printer 897 for printing them out in the form of a table or graph.

Like the aforementioned fiber scope 832, the electronic endoscope 892 has the slender insert section 839 and the thick operating section 841 formed adjacent to the rear end of the insert section 839. The operating section 841 is provided with the angle knob 843, and the bendable section 845 provided adjacent to the distal end 844 of the insert section 839 can be bent. A universal cord 898 is extended from the operating section 841. When a connector 899 of the universal cord 898 is connected to the light source unit 833, illumination light is supplied to the incident end face of the light guide 847. Also, when a signal cable 886 extended from the connector 899 is connected to the CCU 835, a signal picked up by a CCD 887 provided at the distal end of the insert section 839 can be applied for further processing.

The remaining system of the seventeenth embodiment has the same arrangement as the sixteenth embodiment mentioned above. The seventeenth embodiment inputs data to the fuzzy inference means and carries out the fuzzy inference in a like manner to the sixteenth embodiment, but is different therefrom in such as keeping the inspection results in the data base 897. Accordingly, the seventeenth embodiment has a similar operating effect to that of the fifteenth or sixteenth embodiment.

The arrangement of keeping the inspection results in the data base 897 and synthetically analyzing a number of inspection results also makes it possible to gradually improve or update the membership functions representing the fuzzy rules so that the fuzzy inference will be made with higher reliability.

Further, even when the judgment indicating no necessity of blade replacement is obtained from the past information kept in the data base, the resulting inference value may be also used for inferring after how long period the blade should be replaced.

Figure 75:
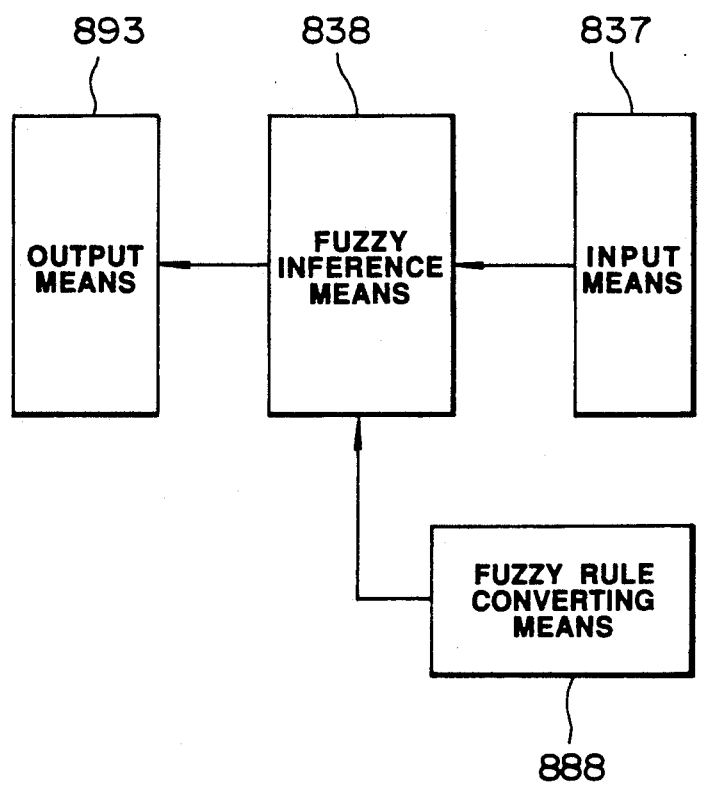
FIG. 75 is a block diagram showing part of a modification of the seventeenth embodiment provided with a conversion means for fuzzy rules.

In the seventeenth embodiment (alternatively in the fifteenth or sixteenth embodiment), for example, it is possible to provide a fuzzy rule converting means 88 which can change the fuzzy rules per inspected object used in the fuzzy inference means 838, as shown in FIG. 75.

By changing an IC card or the like, in which fuzzy rules are written, for each inspection of objects such as piping and jet engine, for example, there can be provided universality that the system can be adapted for many kinds of inspected objects.

According to the fifteenth through seventeenth embodiments, as described above, since the inspection result for each item of non-destructive inspection is inputted to the fuzzy inference means which carries out the fuzzy inference to obtain the inference result, the appropriate inference result without depending on differences between individuals can be provided from synthetic inference based on the inspection results of plural items.

Next, an eighteenth embodiment of the present invention will be described.

This embodiment is concerned with a data interpolating device in which fuzzy inference is used to infer data of a desired position from raw data.

While image data obtained by ultrasonic diagnosis or the like are data sampled at constant intervals, it is often required to infer data of a desired position from the obtained raw data by interpolation. In the past, for example, the interpolation has been performed with a numerical value operation using data of adjacent two points to determine data of an arbitrary point between those two points. Assuming that data of adjacent two points are $X_n$ and $X_{n+1}$, by way of example, data of a central point between the two points is obtained as an average value $(X_n + X_{n+1})/2$.

In the interpolation using only data of two points, however, the interpolation data fairly deviated from the actual value may be provided, particularly, when the data are changed at a large rate before and after the position to be interpolated. To avoid such a problem, it could be contemplated to obtain a change rate of data so that a closer numerical value operation may be carried out using the change rate to determine more adequate interpolation data. This raises such a problem that because the numerical value operation is very time consuming, the interpolation data cannot be obtained in real time and thus the raw data and the interpolation data cannot be displayed in real time. In view of the above, this embodiment is intended to obtain, at a high speed, the interpolation data expected to be near the actual value.

This embodiment relates to an application of the present invention to data interpolation in a ultrasonic diagnosis device.

Figure 76:
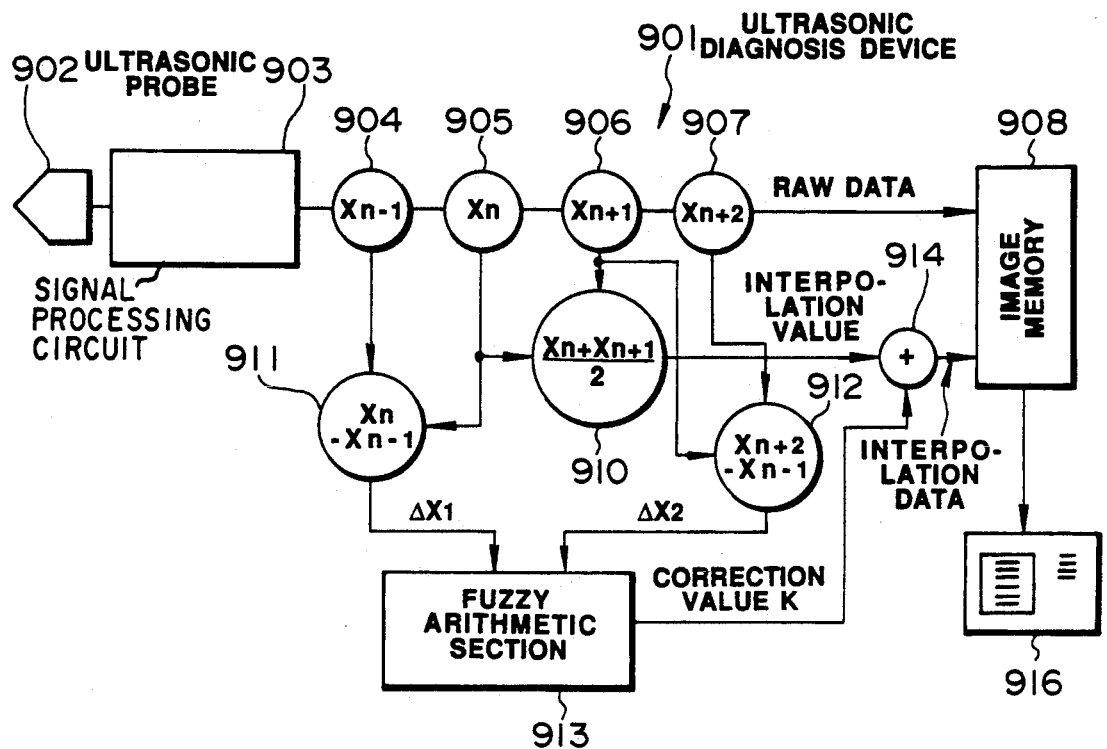

As shown in FIG. 76, a ultrasonic diagnosis device 901 comprises a ultrasonic probe 902 and a signal processing circuit 903 connected to the ultrasonic probe 902. The signal processing circuit 903 transmits ultrasonic pulses to the ultrasonic probe 902, and receives an echo signal from the ultrasonic probe 902 for subsequent signal processing such as logarithmic compression or STC. The ultrasonic probe 902 is arranged to make a linear, sector or radial scan.

Figure 77:
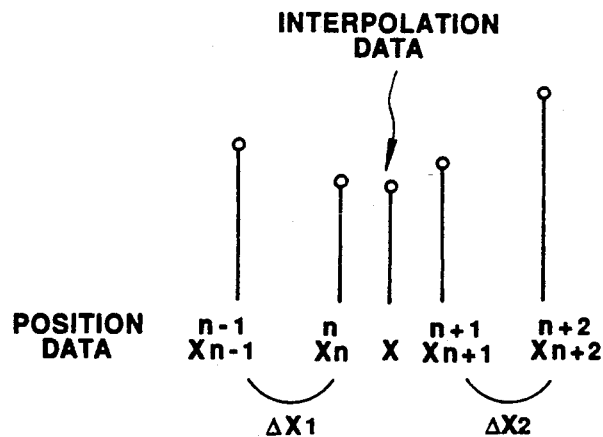

Image data from the signal processing circuit 903 are inputted to an image memory 908 via latches 904, 905, 906, 907. The latches 904, 905, 906, 907 store the image data of positions (scan lines) adjacent to each other. More specifically, assuming that image data of four adjacent points $n-1, n, n+1, n+2$ in some region are respectively $X_{n-1}, X_n, X_{n+1}, X_{n+2}$ as shown in FIG. 77, the latch 904 stores $X_{n-1}$, the latch 905 $X_n$, the latch 906 $X_{n+1}$, and the latch 906 $X_{n+2}$, respectively.

The respective data stored in the latches 905, 906 are inputted to an arithmetic circuit 910 which calculates a value of $(X_n + X_{n+1})/2$ as an interpolation value of the central point between the two points $n$ and $n+1$. The respective data stored in the latches 904, 905 are inputted to an arithmetic circuit 911 which calculates a value of $\Delta X_1 = X_n - X_{n-1}$ as a change rate (gradient) of the data between the two points $n-1$ and $n$. The respective data stored in the latches 906, 907 are inputted to an arithmetic circuit 912 which calculates a value of $\Delta X_2 = X_{n+2} - X_{n+1}$ as a change rate (gradient) of the data between the two points $n+1$ and $n$.

The change rates $\Delta X_1$, $\Delta X_2$ determined by the arithmetic circuits 911, 912 are inputted to a fuzzy arithmetic section 913 which carries out fuzzy inference to determine a correction value k used in correcting the interpolation value $(X_n + X_{n+1})/2$. The interpolation value $(X_n + X_{n+1})/2$ determined by the arithmetic circuit 910 and the correction value k determined by the fuzzy arithmetic section 913 are added to each other by an adder 914, the resulting added value being inputted as interpolation data X to the image memory 908. The image memory 908 stores the raw data and the interpolation data therein. The image data read out of the image memory 908 are inputted to a monitor 916 so that the interpolated ultrasonic information such as ultrasonic tomographic image is displayed on the monitor 916.

The fuzzy inference to be carried out in the fuzzy arithmetic section 913 will be explained below.

In this embodiment, the change rate (gradient) $\Delta X1 = Xn - Xn-1$ between the two points $n-1$ and $n$ and the change rate (gradient) $\Delta X2 = Xn+2 - Xn+1$ of the data between the two points $n+1$ and $n+2$ are expressed by the following fuzzy scale:

| large positive value | ++ |
|---|---|
| small positive value | + |
| unchanged | 0 |
| small negative value | − |
| large negative value | −− |

Here, given $0 \leq Xi \leq 1$ (where $i = \ldots, n-1, n, n+1, n+2, \ldots$), there hold inequalities below:

$$-1 \leq \Delta X1 \leq 1$$

$$-1 \leq \Delta X2 \leq 1$$

The following nine rules are adopted as fuzzy rules in this embodiment. The list below describes only part of "set to be . . ." in state of the consequent portion "the interpolation data is set to be . . . than $(Xn + Xn+1)/2$".

1. If $\Delta X1 = ++$ and $\Delta X2 = --$, then it is set to be large.
2. If $\Delta X1 = ++$ and $\Delta X2 = -$, then it is set to be somewhat large.
3. If $\Delta X1 = +$ and $\Delta X2 = -$, then it is set to be a little large.
4. If $\Delta X1 = +$ and $\Delta X2 = --$, then it is set to be somewhat large.
5. If $\Delta X1 = -$ and $\Delta X2 = ++$, then it is set to be somewhat small.
6. If $\Delta X1 = -$ and $\Delta X2 = +$, then it is set to be a little small.
7. If $\Delta X1 = --$ and $\Delta X2 = +$, then it is set to be somewhat small.
8. If $\Delta X1 = --$ and $\Delta X2 = ++$, then it is set to be small.
9. If $\Delta X1 = 0$ and $\Delta X2 = 0$, then it is not changed.

It is to be noticed that the expression "somewhat" indicates a larger degree or value than "a little".

Figure 78:
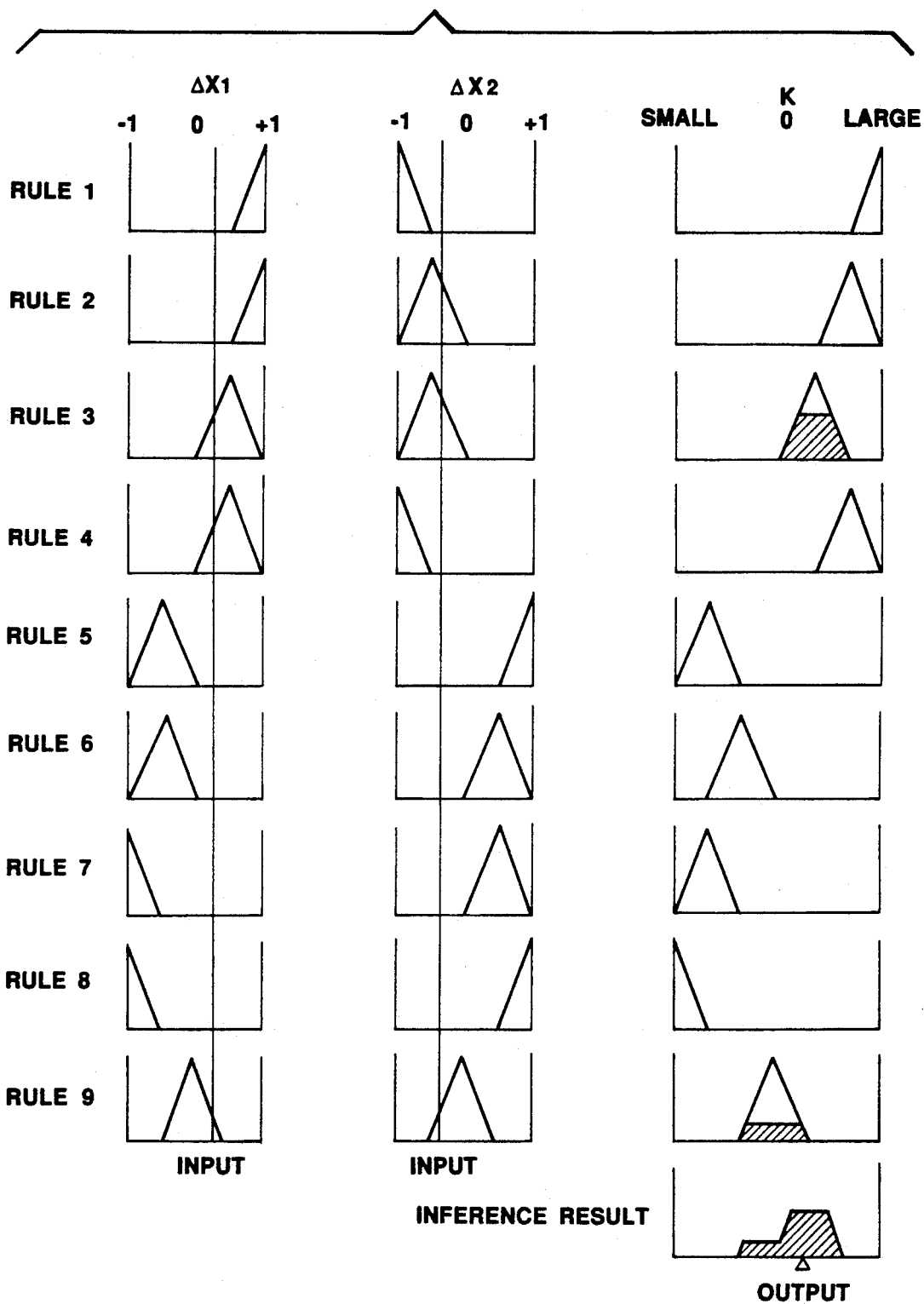

The above rules can be expressed as shown in FIG. 78 using membership functions.

The fuzzy arithmetic section 913 applies the above nine rules to the input values $\Delta X1$, $\Delta X2$ simultaneously, executes MIN operations to determine a degree of coincidence in the antecedent portion of each rule for respective inputs, and further employs the resulting degree as a weight for the consequent portion of that rule. Then, a MAX operation is executed to synthesize the consequent portions of all the rules and a centroid value of the resulting membership function, for example, is derived as an output value. The output value is provided as the correction value k used to increase or decrease the interpolation data from the value of $(Xn + Xn + 1)/2$. By way of example, when input values are given as indicated by vertical lines intersecting the membership functions of the antecedent portion for each rule in FIG. 78, the rules 3 and 9 are satisfied or applied with weights represented by respective hatched areas. There can be thus obtained an illustrated membership function giving the inference result. The above execution of the fuzzy rules and arithmetic operation of the inference result can be implemented at a high speed by using a fuzzy chip.

Figure 79A:
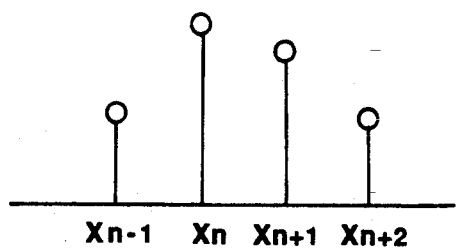
Figure 79B:
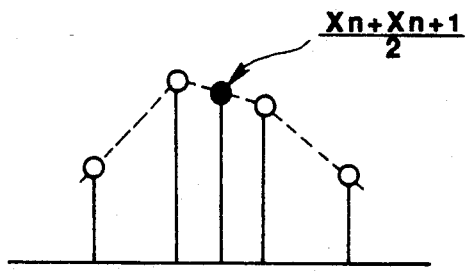
Figure 79C:
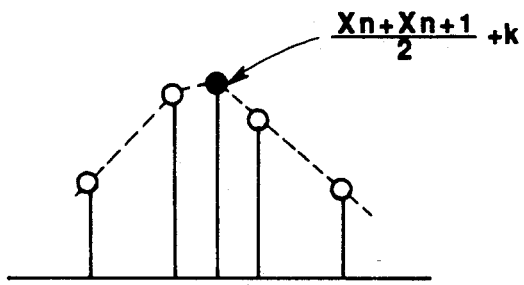

Consider now the case of determining interpolation data of the central point between the two points n and n+1 from raw data. If the interpolation data is given using $(Xn + Xn + 1)/2$ as conventionally, the value fairly deviated from the actual value may be obtained as shown in FIG. 79b. In contrast, with this embodiment of calculating the interpolation data as $(Xn + Xn + 1)/2 + k$ resulted from inputting the change rate of the raw data and adding the correction value k derived from the fuzzy inference to the conventional value, it is possible to obtain the interpolation data which is expected to be closer to the actual value.

In addition, because the fuzzy arithmetic operation can be executed at a high speed using a fuzzy chip, the interpolation data can be provided in real time and the raw data and the interpolation data can be displayed at the same time.

The present invention is not limited to the eighteenth embodiment. For instance, other than interpolation of image data, the present invention is also applicable to interpolation of various data such as interpolation of temperature data in the case of determining temperature distribution.

According to the eighteenth embodiment, as described above, since the interpolation data is obtained with the fuzzy inference based on raw data and a change rate of the raw data in the vicinity of a position for which the interpolation data is to be determined, there is provided an advantage that the interpolation data expected to be closer to the actual value can be obtained at a high speed.

Next, a nineteenth embodiment of the present invention will be described.

This embodiment is intended to realize an output control unit of an electric scalpel device in which optimum voltage is always applied to an electric scalpel using fuzzy inference to ensure safe and reliable cautery.

As shown in FIG. 80, fundamental waves (e.g., 500 KHz) outputted from an oscillator 951 are applied via a gate 952 to a variable gain amplifier (hereinafter abbreviated as VGA) 953 for amplification. An output of the VGA 953 is supplied to a primary winding of an isolation transformer 956 via an HF (RF) current sensor 954 and switch contacts 955a of a relay. Then, a high-frequency current is supplied from an isolated secondary winding of the transformer 956 to a probe 957 and a patient plate 958, thereby cauterizing a portion of a patient 959 to be treated.

An HF voltage sensor 960 for detecting high-frequency voltage VH is connected to an output terminal of the VGA 953 in such a manner as to detect the high-frequency voltage VH outputted from the VGA 953. Also, a high-frequency current AH outputted from the VGA 953 is detected by the HF current sensor 954. Both the detected high-frequency voltage VH and current AH are applied to a fuzzy engine 961 for carrying out fuzzy inference to control an output of the VGA 953.

To the secondary winding, i.e., the output terminal, of the insulation transformer 956, there are further connected an output current sensor 962 and a feedback current sensor 963 for detecting an output current (supply current) IA and a feedback current IP, respectively. The output current sensor 962 serves to detect the current IA outputted from both ends of the secondary winding, and the feedback current sensor 963 serves to detect the feedback current IP flowing from the probe 975 to the patient plate 958 via the patient 959.

The probe 957 is inserted through a channel of an electronic scope 964, and a conductor portion of the electronic scope 964, such as a braided tube around it, is connected to one terminal of the isolation transformer 956 via a lead wire 965, allowing a high-frequency leak current IS to flow through the lead wire 965.

The currents IA, IP respectively detected by the output current sensor 962 and the feedback current sensor 963 are also inputted to the fuzzy engine 961. Based on the above input information, the fuzzy engine 961 outputs amplification factor deciding output information AMPH to a defuzzy fire 967, thereby controlling an amplification factor of the VGA 953 so that the current supplied to the patient 959 via the probe 957 becomes an appropriate value. The defuzzy fire 967 outputs an HF voltage adjustment signal, as a determinative value for determining the amplification factor of the VGA 953, to an amplification factor control terminal of the VGA 953.

The switch contacts 955a of the relay are turned on/off by depressing a foot switch 971 to energize or deenergize a drive section 955b of the relay via a driver 972. The output of the driver 972 is also applied to a controller 968 so that when the foot switch 971 is depressed to be closed, a start of cautery is transmitted to the controller 968.

The fuzzy engine 961 determines impedance Z and cautery power W from the data outputted from the detection means, that is, VH, AH out of VH, AH, IA, IP, and also calculates a current feedback factor $\theta$ from IP, IA. Based on the data thus derived, the fuzzy engine 961 applies the amplification factor deciding output information AMPH, set to develop the voltage VH which is determined with the fuzzy inference so that all parameter values fall in hatched areas in FIGS. 81 and 82, to the defuzzy fire 967 which in turns applies the amplification factor HTS corresponding to AMPH, as a determinative value, to the VGA 953. With the closed loop thus established, the cautery energy supplied to the diseased area is always held at optimum voltage and thus current.

Figure 81:
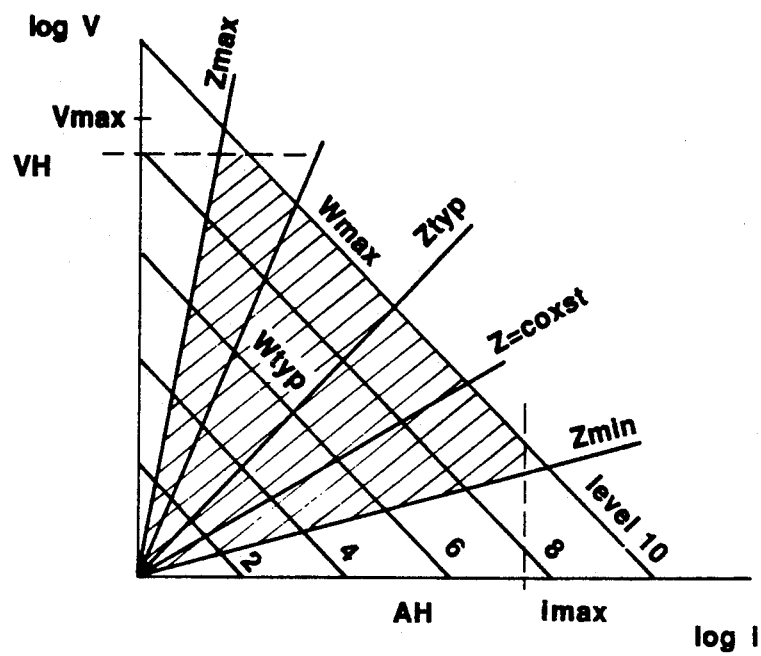

Upon the foot switch 971 being depressed, the relay contacts 955a are closed to establish an output circuit for producing the cautery voltage and, at the same time, the start of cautery is transmitted to the controller 968. Further applied to the controller 968 are a cautery mode (CUT, COAG., or BLEND) and a cautery level (Level 1-10) from mode switched on a display panel 969. In response to a cautery start signal, the controller 968 outputs the cautery level (LEV) to the fuzzy engine 961, and also outputs an output waveform corresponding to the selected cautery mode to the gate 952. Based on AH and VH, the device operates in a manner as shown in FIG. 81. More specifically, there is set an upper limit Zmax of the impedance Z derived by Z=VH/VA. The upper limit Zmax implies the fact that the probe 957 or the patient plate 958 is detached or about to detach from the patient or the diseased area, i.e., the dangerous condition. In this case, therefore, an alarm is issued and the power output is stopped.

There is also set a lower limit (Zmin) of the impedance Z. The lower limit Zmin implies such the fact that the probe 957 is contacted with a metallic portion of the scope 964, i.e., the condition where cautery cannot be performed effectively. In this case, too, an alarm is issued and the power output is stopped. An upper limit of the output power W is determined within a region sandwiched between Zmax and Zmin depending on the level (LEV) indicated by the controller 968. In other words, the region surrounded by Zmax, Zmin and W is given as a domain or value zone in which VH, AH can take practical values. The electric scalpel is to apply high-frequency energy to the diseased area for heating cells thereabout, so that those cells may be cut by transpiration in a moment or protein may be coagulated to stop bleeding. Thus, the electric scalel is also required to apply a treatment to only a restricted area as small as possible. In view of the above, it is required to treat those cells at the target location in a moment before heat will not be conducted to surrounding cells, and further desirable to apply the voltage as high as allowable in a shorter period of time. As the cautery proceeds, the impedance Z of the diseased area is increased and, upon a polyp or the like being cut, it is remarkably increased. The value of VH is increased depending on such a change rate of the impedance Z, and the power output is stopped at the completion of cutting. If blood discharges during the cautery, the impedance Z is abruptly lowered. This occasion can be coped with, for example, by changing the cautery mode to the coagulation mode.

Figure 82:
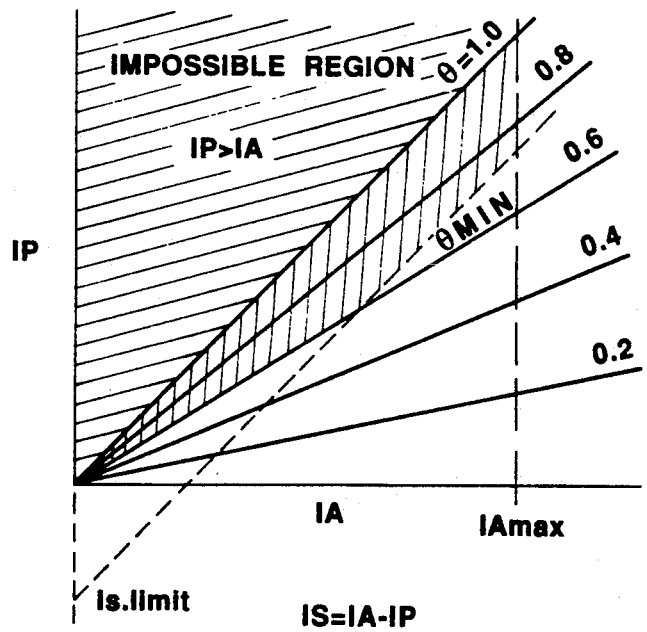

An operating point of the device is determined within an operating region shown in FIG. 82 based on IA and IP. IA is proportional to both AH and the winding ratio (n) of the isolation transformer 956. Since IA supplied from the electric scalpel device is shunted halfway through the scope 964 and the like, all the value of IA will not reach the diseased area. Therefore, IP is measured as a current actually passing through the diseased area. In other words, IP is an available component and IA−IP (=IS) is an unavailable component. Defining the ratio of the available current IP to the supply current IA as a current feedback factor ($\theta$=IP/IA), if $\theta$ is smaller than a setting value ($\theta$ min), this condition is regarded as indicating the presence of some trouble in the cautery system, whereupon an alarm is issued and the power output is stopped. Because the unavailable current IS is also a high-frequency current, there may occur an accident that some unexpected portion is burnt. Thus, even if $\theta$ is within the setting value, the absolute value of IS could reach a possibly dangerous level depending on the value of IA. Accordingly, there is an upper limit (IS limit) of IS. In FIG. 82, the region surrounded by $\theta$ min, $\theta$=1.0 and ISlimit is an appropriate region. VH is controlled to take such a value as meeting both the appropriate regions shown in FIGS. 81 and 82.

According to this embodiment, the optimum voltage can be always applied to the probe for ensuring safe and reliable cautery treatment.

It is to be noted that some of the aforementioned embodiments are optionally combined with each other to constitute further different embodiments and these modified embodiments are also involved in a scope of the present invention.

What is claimed is:

1. An insert device comprising:
   an insert section to be inserted into a tract or cavity;
   observation/treatment means provided at a distal end of said insert section for observing or treating the inside of said tract or said cavity;
   detection means for detecting a plurality of status signals related to an environmental condition of said device; and
   fuzzy control means for synthetically processing said plurality of status signals from said detection means and controlling said observation/treatment means or insert operation inserting said insert section into said tract or said cavity.

2. An insert device according to claim 1, wherein said insert section has a plurality of segments capable of being controlled to bend individually, said detection means detects bend qualities of said respective segments, and said fuzzy control means compositely determines signals corresponding to the bend quantities of at least two of said segments to be controlled on a base end side thereof and controls a bending operation of said segments to be controlled.

3. An insert device according to claim 1, wherein said cavity insert device further comprises image sensing means for converting an image of an object into an electrical signal, and said detection means detects an object signal from said image sensing means as one of said plurality of status signals.

4. An insert device according to claim 3, wherein said fuzzy control means includes means for controlling an iris diaphragm of said image sensing means.

5. A cavity insert device according to claim 3, wherein said fuzzy control means includes means for controlling an amplification means for amplifying the electrical signal from said image sensing means.

6. An insert device according to claim 3, wherein said cavity insert device includes an endoscope equipped with said image sensing means, and said fuzzy control means includes means for controlling quantities of air and water supplied to said endoscope.

7. An insert device according to claim 1, wherein said cavity insert device includes a high-frequency cautery treatment unit comprising a high-frequency cautery treatment means for cauterizing tissues by a high-frequency drive signal supplied thereto, and high-frequency drive signal supply means for supplying the high-frequency drive signal to said high-frequency cautery treatment means.

8. An insert device according to claim 7, wherein said high-frequency drive signal supply means includes a high-frequency oscillator and a variable gain amplifier including means for amplifying the high-frequency signal of said high-frequency oscillator with a gain changed depending on a control signal applied to a control terminal of said amplifier.

9. An insert device according to claim 8, further comprising voltage detecting means for detecting voltage of the high-frequency signal outputted from said variable gain amplifier, supply current detecting means for detecting a supply current of said high-frequency drive signal supplied to said high-frequency cautery treatment means via an isolation transformer for isolating said high-frequency signal, wherein said high-frequency cautery treatment means includes a cautery electrode and feedback current detecting means for detecting a feedback current that flows between said cautery electrode and a return electrode used in pair with said cautery electrode, respective outputs of said detecting means being delivered as said plurality of status signals to said fuzzy control means.

10. An insert device according to claim 1, wherein said detection means is further capable of detecting subject information of a plurality of sections in said tract and cavity at the distal end of said insertion section individually.

11. An insert device according to claim 10, wherein an observation optical system is constructed in the distal end of said insert section;

said observation means comprising an image sensing section for sensing an image in a tract and cavity from said observation optical system; and said detection means for detecting said information of a plurality of sections in said tract and cavity from said observation optical system individually.

12. An insert device according to claim 11, wherein said detection means includes a plurality of light receiving elements being different from an image sensing section of said observation means.

13. An insert device according to claim 12, wherein said insertion section includes light dividing elements dividing a luminance flux from said observation optical system in two, one light dividing element leads the flux to said image sensing section and the other light dividing element leads the flux to said plurality of light receiving elements.

14. An insert device according to claim 7, wherein said detection means receives an image signal in said tract and cavity from an image sensing section of said observation means.

15. An insert device according to claim 10, further comprising drive means for making said insert section advance and retreat in an axial direction of said insert section; and said fuzzy control means for controlling said drive means.

16. A cavity insert device comprising:
an insert section to be inserted into a cavity;
means provided at a distal end of said insert section for observing or treating the inside of said cavity and so on;
detection means for detecting a plurality of status signals related to an environmental condition of said device; and
fuzzy control means for synthetically processing said plurality of status signals according to inference rules from said detection means and controlling said observation or treatment means before starting an insert operation of said insert section, said fuzzy control means being includes means for changing inference rules used during control of said observation or treatment means.

17. A cavity insert device according to claim 16, wherein said means for changing inference rules includes selectively fitted IC cards which store different memberships therein.

18. An endoscope device comprising:
image sensing means for converting an image of an object into an electrical signal;
detection means for detecting object information from the electrical signal outputted from said image sensing means;
operational element means related to an insert or observing operation of an endoscope; and
fuzzy inference means for receiving the object information from said detection means as input signals, and synthetically processing said input signals to output a control signal to control said operational element means.

19. An endoscope system according to claim 18 wherein said endoscope has a light guide for transmitting illumination light supplied to one end face thereof from an external light source unit and emitting the illumination light from the other end face thereof.

20. An endoscope system according to claim 18, further comprising signal processing means for processing the electrical signal outputted from said image sensing means to produce a standard video signal, and display means for displaying said standard video signal.

21. An endoscope system according to claim 20 wherein said functional element means includes amplification means provided in said signal processing means for changing an amplification factor of said electric signal depending on said control signal.

22. An endoscope system according to claim 18, wherein said endoscope has a slender insert section and bending drive means for driving a bendable portion provided in said insert section to produce a bending movement.

23. An endoscope device according to claim 22, wherein said operational element means includes said bending drive means.

24. An endoscope system according to claim 18, further comprising drive signal generating means for generating a drive signal to cause said image sensing means to output said electric signal.

25. An endoscope device according to claim 24, wherein said operational element means includes a device shutter for changing time intervals of shutter openings for generating said drive signal.

26. An endoscope device according to claim 18, further comprising air and water supply means comprised of air and water supply drive means for supplying air and water, and a tube line provided in said endoscope for allowing air and water or a similar fluid supplied by said air and water supply drive means to pass therethrough.

27. An endoscope device according to claim 18, wherein said fuzzy inference means further comprises a plurality of fuzzy control sections having fuzzy rules different from each other, and switching means for selectively switching over said plurality of fuzzy control sections.

28. An endoscope device according to claim 18, wherein said operational element means includes a diaphragm provided in said light source unit for adjusting the intensity of the illumination light.

29. An endoscope device according to claim 18, wherein said operational element means includes said air and water supply drive means.

30. An endoscope device according to claim 18, wherein said endoscope device further comprises photometric means for detecting the intensity of light received by said image sensing means, and said operational element means includes said photometric means.

31. An endoscope system according to claim 18, wherein said endoscope has an elongated insertion section and advancing and retreating torsion drive means for making said elongated insert section advance, retreat, twist and drive.

32. An endoscope, system according to claim 31, wherein said operational element means includes said advancing and retreating torsion drive means.

33. An endoscope system according to claim 18, further comprising signal processing means for processing the electric signal outputted from said image sensing means to produce a standard video signal, and having recording means for recording said video signal.

34. An endoscope system comprising:
an endoscope having a slender insert section;
controlled element means provided to be controlled for setting said endoscope to a desired observing state;
information signal detecting means for producing a plurality of information signals from outside said endoscope to control said controlled element means; and
fuzzy inference means for carrying out an arithmetic operation to compositely process said plurality of information signals and producing a control signal to control said controlled element means from a result of said arithmetic operation.

35. An endoscope system according to claim 34, further comprising image sensing means to produce an image signal corresponding to an object observed during said desired observing state.

36. An endoscope system according to claim 35, wherein said endoscope has an objective optical system for focusing an optical image of said object.

37. An endoscope system according to claim 36 wherein said endoscope has a light guide for transmitting illumination light supplied to one end face thereof from an external light source unit and emitting the illumination light from the other end face thereof.

38. An endoscope device according to claim 37, wherein said endoscope system further comprises movement drive means for controlling a movement quantity, through which said insert section is moved axially of said insert section, by a signal applied to a first control input terminal, and bending drive means for controlling a drive quantity, through which a bendable portion provided in said insert section is driven to bend, by a signal applied to a second control input terminal, said controlled element means consisting of said movement drive means and said bending drive means with said control signal applied to said first and second control input terminals.

39. An endoscope device according to claim 38, wherein said endoscope device further comprises torsion drive means for controlling a torsion quantity, through which said insert section is twisted, by a signal applied to a control input terminal, and said controlled element means includes said torsion drive means with said control signal applied to said control input terminal.

40. An endoscope device according to claim 36, further comprising air and water supply means comprised of air and water supply drive means for supplying air and water, and a tube line provided in said endoscope for allowing air and water or similar fluid supplied by said air and water supply drive means to pass therethrough.

41. An endoscope device according to claim 40, further comprising suction drive means connected to said tube line for sucking said air and water or similar fluid through said tube line.

42. An endoscope device according to claim 41, wherein said controlled element means includes said air and water supply drive means and said suction drive means.

43. An endoscope device according to claim 42, wherein said information signal detecting means includes first detection means for detecting a quantity of liquid supplied by said air and water supply drive means and outputting a corresponding first signal, and second detection means for detecting a quantity of liquid sucked by said suction drive means and outputting a corresponding second signal, said first and second detecting signals being outputted to said fuzzy inference means.

44. An endoscope device according to claim 43, wherein said information signal detecting means further comprises a third detection means for detecting transparency of liquid sucked by said suction drive means and outputting a corresponding third signal to said fuzzy inference means.

45. An endoscope device according to claim 26, wherein said endoscope further comprises an actuator comprising a plurality of segments jointed to each other axially of said insert section in a bendable manner, and a bending drive member including means for bending said plurality of segments making up said actuator by a drive signal such that a bend angle of the preceding segment nearer to the distal end of said insert section is in turn transmitted to the succeeding segment, and wherein said endoscope device further comprises bend angle detecting means for detecting a bend angle of one or more said segments, and difference detecting means for determining a difference between a detected value and a target value of each bend angle detected by said bend angle detecting means, detection outputs of said bend angle detecting means and said difference detection means being outputted as said information signals to said fuzzy inference means.

46. An endoscope system according to claim 45, wherein said bending drive member is made of shape memory material having characteristics to extend/contract upon energization and heating by the drive signal.

47. An endoscope device according to claim 36, wherein said endoscope further comprises an actuator comprising a plurality of segments jointed to each other axially of said insert section in a bendable manner, and a bending drive member including means for bending said plurality of segments making up said actuator by a drive signal such that a bend angle of the preceding segment nearer to the distal end of said insert section is in turn transmitted to the succeeding segment, and wherein said endoscope device further comprises bend angle detecting means for detecting respective bend angles of plural segments on the distal end side, and difference detecting means for determining a difference between a detected value and a target value of each bend angle detected by said bend angle detecting means, detection outputs of said bend angle detecting means and said difference detecting means being outputted as said information signals to said fuzzy inference means so that the bend angle of the succeeding segment is in turn controlled depending on an output of said fuzzy inference means.

48. An endoscope system according to claim 35, wherein said image sensing means has an objective optical system for focusing an optical image of said object, and a solid state image sensing device for photoelectrically converting the optical image from said object optical system.

49. An endoscope device according to claim 48 wherein said endoscope has a light guide for transmitting illumination light supplied to one end face thereof from an external light source unit and emitting the illumination light from the other end face thereof.

50. An endoscope device according to claim 4, wherein said controlled element means includes a diaphragm provided in said light source unit for adjusting the intensity of the illumination light.

51. An endoscope system according to claim 48 further comprising signal processing means for processing the image signal outputted from said image sensing means to produce a standard video signal, and display means for displaying said standard video signal.

52. An endoscope device according to claim 51, wherein said endoscope device further comprises input means for data required in producing said plurality of information signals related to an inspected location in the object image displayed on said display means, and said information signal detecting means carries out processing to produce said plurality of information signals upon entry of the data from said input means.

53. An endoscope system according to claim 52, wherein said input means includes at least one of a keyboard, mouse and light pen.

54. An endoscope device according to claim 52, wherein said information signal detecting means includes storage means of object information including at least size information of the object, and carries out processing to read said object information out of said storage means and produce said plurality of information signals upon entry of the data from said input means.

55. An endoscope device according to claim 51, wherein said signal processing means includes image quality changing means for automatically controlling the image quality of the video signal displayed on said display means by said control signal outputted from said fuzzy inference means.

56. An endoscope system according to claim 48, wherein said endoscope has bending drive means for driving a bendable portion provided in said insert section to produce a bending movement.

57. An endoscope system according to claim 56, wherein said controlled element means includes means for controlling said bending drive means.

58. An endoscope device according to claim 48, further comprising drive signal generating means for generating a drive signal to cause said image sensing means to output said image signal.

59. An endoscope device according to claim 58, wherein said controlled element means includes a system shutter for changing time intervals of shutter openings for generating said drive signal.

60. An endoscope device according to claim 48, further comprising air and water supply means comprised of air and water supply drive means for supplying air and water, and a tube provided in said endoscope for allowing air and water or similar fluid supplied by said air and water supply drive means to pass therethrough.

61. An endoscope device according to claim 60, wherein said controlled element means includes said air and water supply drive means.

62. An endoscope system according to claim 61, wherein said storage means comprises at least one of a ROM and an optical card.

63. An endoscope device according to claim 61, wherein said endoscope includes a channel through which a treatment appliance can be inserted, and said information signal detecting means produces from said image signal said plurality of information signals to determine optical characteristics of said treatment appliance.

64. An endoscope system according to claim 48 wherein said controlled element means includes amplification means provided in said signal processing means for changing an amplification factor of said image signal depending on said control signal.

65. An endoscope device according to claim 64, wherein said information signal detecting means includes luminance detecting means for detecting luminance information from said image signal and outputting a corresponding luminance signal to said fuzzy inference means, and color detecting means for detecting a specific color related to the object from said image signal and outputting a corresponding specific color signal to said fuzzy inference means.

66. An endoscope device according to claim 64, wherein said information signal detecting means includes image quality factor detecting means for detecting information of an image quality deciding factor from said image signal and outputting a corresponding image quality factor signal, as one of said plurality of information signals, to said fuzzy inference means, the amplification factor of said amplification means being controlled by said control signal outputted from said fuzzy inference means to control the image quality.

67. An endoscope device according to claim 64, wherein said fuzzy inference means includes means for automatically controlling a luminance level of said image signal based on said plurality of information signals.

68. An endoscope system according to claim 48 wherein said endoscope system further comprises photometric means for detecting the intensity of light received by said image sensing means, and said controlled element means includes means for controlling, said photometric means.

69. An endoscope device according to claim 48, wherein said endoscope system further comprises movement drive means for controlling a movement quantity, through which said insert section is moved axially in said insert section, by a signal applied to a first control input terminal, and bending drive means for controlling a drive quantity, through which a bendable portion provided in said insert section is driven to bend, by a signal applied to a second control input terminal, said controlled element means consisting of said movement drive means and said bending drive means with said control signal applied to said first and second control input terminals.

70. An endoscope device according to claim 69, wherein said information signal detecting means includes means for respectively detecting a central position of the cavity into which the distal end of said insert section is inserted and an acceleration of the distal end of said insert section from the image signal outputted from said image sensing means.

71. An endoscope device according to claim 70, wherein said fuzzy inference means controls said controlled element means using input information adapted to infer information from said central position and said acceleration.

72. An endoscope system according to claim 70, wherein said information signal detecting means is a luminance detecting means for detecting luminance information of the light reflected in plural directions from the cavity into which the distal end of said insert section is inserted.

73. An endoscope system according to claim 72, wherein said luminance detecting means detects said luminance information from the image signal outputted from said image sensing means.

74. An endoscope system according to claim 69, wherein said fuzzy inference means controls said controlled element means using input information which infers said luminance information in plural directions.

75. An endoscope device according to claim 35, wherein said endoscope is an ultrasonic endoscope for obtaining an ultrasonic image, and said image sensing means comprises an ultrasonic oscillator made of material having a large electromechanical coupling constant.

76. An endoscope device according to claim 75, wherein said endoscope device further comprises a variable gain amplification means for amplifying the ultrasonic image signal received by said ultrasonic oscillator with a gain which is changed depending on said control signal applied to a gain control terminal, lapse time detecting means for detecting a time lapsed from emission of ultrasonic waves to reception of the ultrasonic waves, angle detecting means for detecting an approach angle of the ultrasonic waves emitted from said ultrasonic oscillator toward the object, and frequency detecting means for detecting frequency of the ultrasonic waves, at least two of detection signals of said lapse time detecting means, said angle detecting means and said frequency detecting means being outputted to said fuzzy inference means.

77. An endoscope device according to claim 75, wherein said endoscope device further comprises change rate detecting means for detecting a change rate of at least two signal data adjacent to each other in the ultrasonic image signal received by said ultrasonic oscillator, and outputting the detected change rate and at least one of said two signal data, as said plurality of information signals, to said fuzzy inference means.

78. An endoscope device according to claim 77, wherein said fuzzy inference means includes means for producing interpolation data to interpolate a value between said two signal data using the data of said change rate and said one signal data.

79. An endoscope device according to claim 35, further comprising division means for dividing information of one picture given by said image signal into plural parts and outputting at least one part of information divided by said division means.

80. An endoscope system according to claim 79, further comprising decision means for said endoscope equipped with said image signal, an output of said decision means being used to select at least one part of information outputted from said division means to said information signal detecting means.

81. An endoscope device according to claim 34, wherein said fuzzy inference means comprises a plurality of fuzzy control sections including fuzzy rules different from each other, and switching means for selectively switching over said plurality of fuzzy control sections.

82. An endoscope device according to claim 81, wherein said switching means includes decision means for determining endoscope types for switching over said fuzzy control sections depending on an output of said decision means.

83. An endoscope system according to claim 34, further comprising input means for membership functions to define fuzzy inference rules used in said fuzzy inference means.

84. An endoscope device according to claim 34, wherein said fuzzy inference means includes storage means storing inference rules to perform fuzzy inference, and a fuzzy inference section for applying the inference rules in said storage mans to said plurality of information signals inputted from said information signal detecting means, thereby deriving a reference result.

85. An endoscope device according to claim 34, wherein said controlled element means is controlled by said control signal so that said endoscope is introduced up to a position where said endoscope can observe a location of the object to be observed during said desired observing state.

86. An endoscope device according to claim 34, wherein said controlled element means is controlled by said control signal so that said endoscope is set to a desired state for observing the location of the object to be observed, under a condition where said endoscope has been set to the position where said endoscope can observe the location of the object to be observed.

87. An endoscope device comprising:
   an endoscope comprising;
      a slender insert section, and
      image sensing means to produce an image signal corresponding to an image of an object;
   detection means for detecting a plurality of items of object information from the image signal outputted from said image sensing means;
   fuzzy inference means for carrying out an arithmetic operation to compositely infer said plurality of items of object information and producing a control signal from a result of said arithmetic operation; and
   controlled element means controlled by said control signal to set said endoscope to a desired state for observation and inspection.

* * * * *